(12) United States Patent
Cazaux et al.

(10) Patent No.: US 8,865,408 B2
(45) Date of Patent: Oct. 21, 2014

(54) SIGNATURE FOR THE DIAGNOSIS OF CANCER AGGRESSIVENESS AND GENETIC INSTABILITY

(75) Inventors: Christophe Cazaux, Plaisance du Touch (FR); Jean-Sébastien Hoffmann, Toulouse (FR); Jean-Christophe Bourdon, Dundee (GB); Alice Machado Da Silva, Belo Horizonte (BR); Henri Roche, Pibrac (FR)

(73) Assignees: Centre National de la Recherche Scientifique (CNRS), Paris (FR); Universite Paul Sabatier Toulouse III, Toulouse (FR); Institut Claudius Regaud, Toulouse (FR)

( * ) Notice: Subject to any disclaimer, the term of this patent is extended or adjusted under 35 U.S.C. 154(b) by 375 days.

(21) Appl. No.: 13/110,749

(22) Filed: May 18, 2011

(65) Prior Publication Data

US 2012/0021935 A1    Jan. 26, 2012

Related U.S. Application Data

(63) Continuation-in-part of application No. PCT/EP2010/067401, filed on Nov. 12, 2010.

(30) Foreign Application Priority Data

Nov. 13, 2009 (EP) ..................................... 09306096

(51) Int. Cl.
| | | |
|---|---|---|
| *C12Q 1/68* | (2006.01) | |
| *C07H 21/00* | (2006.01) | |
| *C40B 40/08* | (2006.01) | |
| *G01N 33/574* | (2006.01) | |

(52) U.S. Cl.
CPC ........ *C12Q 1/6886* (2013.01); *C12Q 2600/118* (2013.01); *C12Q 2600/158* (2013.01); *C12Q 2600/156* (2013.01); *C12Q 2600/136* (2013.01); *C12Q 2600/112* (2013.01); *C12Q 2600/106* (2013.01)
USPC ......... 435/6.12; 435/6.1; 435/6.11; 435/6.14; 435/7.1

(58) Field of Classification Search
CPC ........... C12Q 1/6886; C12Q 2600/112; C12Q 2600/118; C12Q 2600/158; C12Q 2600/166
USPC .......................... 435/6.1, 6.11, 6.12, 6.14, 7.1
See application file for complete search history.

(56) References Cited

FOREIGN PATENT DOCUMENTS

| | | | |
|---|---|---|---|
| WO | WO 2004/080976 A1 | 9/2004 | |
| WO | WO 2005/053662 A1 | 6/2005 | |
| WO | WO 2007/001684 A2 | 1/2007 | |
| WO | WO 2008/077165 A1 | 7/2008 | |
| WO | WO 2008/082856 A1 | 7/2008 | |
| WO | WO 2009/046205 A1 | 4/2009 | |

OTHER PUBLICATIONS

Hurtado del Pozo et al.; IPO8 and FBXL10: New Reference Genes for Gene Expression Studies in Human Adipose Tissue; Obesity; vol. 18, No. 5, pp. 897-903; published May 2010.*
Bartkova et al., "DNA damage response as a candidate anti-cancer barrier in early human tumorigenesis", Nature, vol. 434, Apr. 14, 2005, pp. 864-870.
Bergoglio et al., "Deregulated DNA Polymerase β Induces Chromosome Instability and Tumorigenesis", Cancer Research, vol. 62, Jun. 15, 2002, pp. 3511-3514.
Bergoglio et al., "Localisation of human DNA polymerase κ to replication foci", Journal of Cell Science, vol. 115, No. 23, 2002, pp. 4413-4418.
Chirgwin et al., "Isolation of Biologically Active Ribonucleic Acid from Sources Enriched in Ribonuclease" Biochemistry, vol. 18, No. 24, 1979, pp. 5294-5299.
Corpet, "Multiple sequence alignment with hierarchical clustering", Nucleic Acids Research, vol. 16, No. 22, 1988, pp. 10881-10890.
Eisenberg et al., "Human housekeeping genes are compact", Trends in Genetics, vol. 19, No. 7, Jul. 2003, pp. 362-365.
Gorgoulis et al., "Activation of the DNA damage checkpoint and genomic instability in human precancerous lesions", Nature, vol. 434, Apr. 14, 2005, pp. 907-913.
Greenlee, "Cancer Statistics, 2000", Cancer Journal for Clinicians, vol. 50, No. 1, Jan./Feb. 2000, pp. 7-33.
Higgins et al., "Overexpression of POLQ Confers a Poor Prognosis in Early Breast Cancer Patients", Oncotarget, vol. 1, No. 3, pp. 175-184 (UKPMC Funders Group, Author Manuscript, 16 pages), Jul. 1, 2010.
Huang et al., "Pharmacogenetics and pharmacogenomics of anticancer agents", Cancer Journal for Clinicians, vol. 59, No. 1, Jan./Feb. 2009, pp. 42-55.
Huen et al., "The DNA damage response pathways: at the crossroad of protein modifications", Cell Research, vol. 18, No. 1, Jan. 2008, pp. 8-16, (Published online Dec. 18, 2007).
International Search Report for International Application No. PCT/EP2010/067401 dated Dec. 20, 2010.

(Continued)

*Primary Examiner* — James Ketter
*Assistant Examiner* — Antonio Galisteo Gonzalez
(74) *Attorney, Agent, or Firm* — Birch, Stewart, Kolasch & Birch, LLP

(57) ABSTRACT

The present invention relates to a method for diagnosing aggressiveness and/or genetic instability of a cancer in a patient from a cancer sample of the patient. The method includes measuring in vitro the expression level of the POLQ gene and the expression level of a control gene in the patient cancer sample, calculating an expression level ratio of the expression level of POLQ to the expression of the control gene in the patient cancer sample, comparing the expression level ratio to a corresponding threshold value, and diagnosing cancer aggressiveness and genetic instability if the POLQ expression level ratio is superior to a corresponding threshold value. Dedicated microarrays and kits are also described, as well as a method of selecting a suitable treatment.

Figure 1:
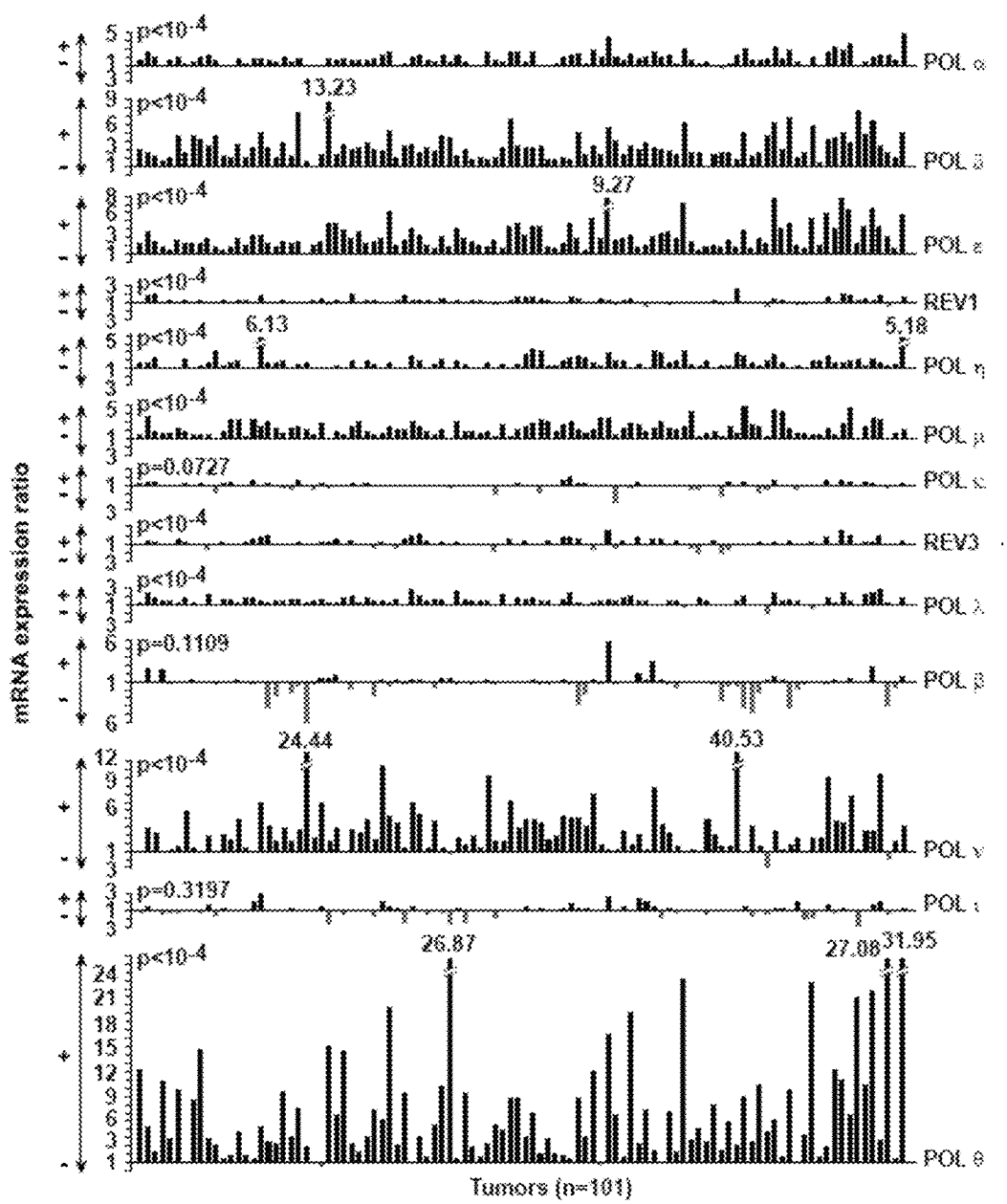

10 Claims, 16 Drawing Sheets
(7 of 16 Drawing Sheet(s) Filed in Color)

(56) References Cited

OTHER PUBLICATIONS

Jagannathan et al., "Base excision repair in nucleosome substrates", Chromosome Research, vol. 14, 2006, pp. 27-37.

Jemal et al., "Cancer Statistics, 2009", Cancer Journal for Clinicians, vol. 59, No. 4, 2009, Jul./Aug. 2009, pp. 225-249, (Published online May 27, 2009).

Kawamura et al., "DNA Polymerase θ is Preferentially Expressed in Lymphoid Tissues and Upregulated in Human Cancers", International Journal of Cancer, vol. 109, 2004, pp. 9-16, XP002568122.

Lemée et al., "DNA polymerase θ up-regulation is associated with poor survival in breast cancer, perturbs DNA replication, and promotes genetic instability", Proceedings of the National Academy of Sciences, vol. 107, No. 30, Jul. 27, 2010, pp. 13390-13395.

Lenz, "Prognostic/Predictive Molecular Markers in Colorectal Cancer", Gastrointestinal Cancer Research, vol. 1, Iss. 4, Sup. 2, Jul./Aug. 2007, pp. S29-S32.

Marini et al., "POLN, a Nuclear PolA Family DNA Polymerase Homologous to the DNA Cross-link Sensitivity Protein Mus308, The Journal of Biological Chemistry, vol. 278, No. 34, Aug. 22, 2003, pp. 32014-32019.

Masuda et al., "DNA polymerase θ contributes to the generation of C/G mutations during somatic hypermutation of Ig genes", Proceedings of the National Academy of Sciences, vol. 102, No. 39, Sep. 27, 2005, pp. 13986-13991.

Petitjean et al., "Impact of Mutant p53 Functional Properties on TP53 Mutation Patterns and Tumor Phenotype: Lessons from Recent Developments in the IARC TP53 Database", Human Mutation, vol. 28, No. 6, 2007, pp. 622-629, (Published online Feb. 20, 2007).

Pillaire et al., "Upregulation of Error-Prone DNA Polymerases β and κ Slows Down Fork Progression Without Activating the Replication Checkpoint", Cell Cycle, vol. 6, Iss. 4, Feb. 15, 2007, pp. 471-477.

Rao et al., "Endogenous γ-H2AX-ATM-Chk2 Checkpoint Activation in Bloom's Syndrome Helicase-Deficient Cells Is Related to DNA Replication Arrested Forks", Mol Cancer Res, vol. 5, No. 7, Jul. 2007, pp. 713-724.

Roché et al., "Sequential Adjuvant Epirubicin-Based and Docetaxel Chemotherapy for Node-Positive Breast Cancer Patients: The FNCLCC PACS 01 Trial", Journal of Clinical Oncology, vol. 24, No. 36, Dec. 20, 2006, pp. 5664-5671, (Published online Nov. 20, 2006).

Seki et al., "High-efficiency bypass of DNA damage by human DNA polymerase Q", The EMBO Journal, vol. 23, No. 22, 2004, pp. 4484-4494, (Published online Oct. 21, 2004).

Seki et al., "POLQ (Pol θ), a DNA polymerase and DNA-dependent ATPase in human cells", Nucleic Acids Research, vol. 31, No. 21, 2003, pp. 6117-6126.

Walther et al., "Genetic prognostic and predictive markers in colorectal cancer", Nature Reviews, Cancer, vol. 9, Jul. 2009, pp. 489-499, (Published online Jun. 18, 2009).

Wang et al., Mutational Analysis of Thirty-two Double-Strand DNA Break Repair Genes in Breast and Pancreatic Cancers, Cancer Research, vol. 68, No. 4, Feb. 15, 2008, pp. 971-975, XP002568121.

Yoshimura et al., "Vertebrate POLQ and POLβ Cooperate in Base Excision Repair of Oxidative DNA Damage", Mol Cell., vol. 24, No. 1, pp. 115-125, Oct. 6, 2006, (NIH Public Access Author Manuscript, 21 pages).

Zan et al., "The translesion DNA polymerase θ plays a dominant role in immunoglobulin gene somatic hypermutation", The EMBO Journal, vol. 24, No. 21, 2005, pp. 3757-3769, (Published online Oct. 13, 2005).

\* cited by examiner

SEQUENCE LISTING

<160> NUMBER OF SEQ ID NOS: 19

<210> SEQ ID NO 1
<211> LENGTH: 25
<212> TYPE: DNA
<213> ORGANISM: Artificial Sequence
<220> FEATURE:
<223> OTHER INFORMATION: IPO8 primer

<400> SEQUENCE: 1 agggaattg atcagtgcat tccac                                  25

<210> SEQ ID NO 2
<211> LENGTH: 25
<212> TYPE: DNA
<213> ORGANISM: Artificial Sequence
<220> FEATURE:
<223> OTHER INFORMATION: HMBS primer

<400> SEQUENCE: 2
gcggctgcaa cggcggaaga aaaca                                  25

<210> SEQ ID NO 3
<211> LENGTH: 25
<212> TYPE: DNA
<213> ORGANISM: Artificial Sequence
<220> FEATURE:
<223> OTHER INFORMATION: POLA primer

<400> SEQUENCE: 3
tacaaccaac caggtgtggt atttc                                  25

<210> SEQ ID NO 4
<211> LENGTH: 25
<212> TYPE: DNA
<213> ORGANISM: Artificial Sequence
<220> FEATURE:
<223> OTHER INFORMATION: POLD1 primer

<400> SEQUENCE: 4
ctgtttgaag cgggatggat ggcaa                                  25

<210> SEQ ID NO 5
<211> LENGTH: 25
<212> TYPE: DNA
<213> ORGANISM: Artificial Sequence
<220> FEATURE:
<223> OTHER INFORMATION: POLE primer

<400> SEQUENCE: 5
ctttgaagag gtgtgtgatg agatt                                  25

<210> SEQ ID NO 6
<211> LENGTH: 25
<212> TYPE: DNA
<213> ORGANISM: Artificial Sequence
<220> FEATURE:
<223> OTHER INFORMATION: REV1L primer

<400> SEQUENCE: 6
gggaaacatg gggtgggtat atggc                                  25

<210> SEQ ID NO 7
<211> LENGTH: 25
<212> TYPE: DNA
<213> ORGANISM: Artificial Sequence

```
<220> FEATURE:
<223> OTHER INFORMATION: POLH primer

<400> SEQUENCE: 7
tcacacaata aggtcctggc aaaac                                            25

<210> SEQ ID NO 8
<211> LENGTH: 25
<212> TYPE: DNA
<213> ORGANISM: Artificial Sequence
<220> FEATURE:
<223> OTHER INFORMATION: POLM primer

<400> SEQUENCE: 8
gcagaaagcg gggctccagc accac                                            25

<210> SEQ ID NO 9
<211> LENGTH: 25
<212> TYPE: DNA
<213> ORGANISM: Artificial Sequence
<220> FEATURE:
<223> OTHER INFORMATION: POLK primer

<400> SEQUENCE: 9
gccacgaagg ggtccagatt ttatg                                            25

<210> SEQ ID NO 10
<211> LENGTH: 25
<212> TYPE: DNA
<213> ORGANISM: Artificial Sequence
<220> FEATURE:
<223> OTHER INFORMATION: REV3L primer

<400> SEQUENCE: 10
aaaagcccag ggagattggt ggacg                                            25

<210> SEQ ID NO 11
<211> LENGTH: 25
<212> TYPE: DNA
<213> ORGANISM: Artificial Sequence
<220> FEATURE:
<223> OTHER INFORMATION: POLL primer

<400> SEQUENCE: 11
gattgagcag acagtccaga aagca                                            25

<210> SEQ ID NO 12
<211> LENGTH: 25
<212> TYPE: DNA
<213> ORGANISM: Artificial Sequence
<220> FEATURE:
<223> OTHER INFORMATION: POLB primer

<400> SEQUENCE: 12
gagttagtgg cattggtcca tctgc                                            25

<210> SEQ ID NO 13
<211> LENGTH: 25
<212> TYPE: DNA
<213> ORGANISM: Artificial Sequence
<220> FEATURE:
<223> OTHER INFORMATION: POLN primer

<400> SEQUENCE: 13
tggagcaggg aaggagcggc tggct                                            25
```

```
<210> SEQ ID NO 14
<211> LENGTH: 25
<212> TYPE: DNA
<213> ORGANISM: Artificial Sequence
<220> FEATURE:
<223> OTHER INFORMATION: POLI primer

<400> SEQUENCE: 14
ccagctcgca gggagttcat gatca                                              25

<210> SEQ ID NO 15
<211> LENGTH: 25
<212> TYPE: DNA
<213> ORGANISM: Artificial Sequence
<220> FEATURE:
<223> OTHER INFORMATION: POLQ primer

<400> SEQUENCE: 15
gcctttccca ggtggttcaa tactg                                              25

<210> SEQ ID NO 16
<211> LENGTH: 27
<212> TYPE: DNA
<213> ORGANISM: Artificial Sequence
<220> FEATURE:
<223> OTHER INFORMATION: Gi1 Primer

<400> SEQUENCE: 16
tgatgctgtc cccggacgat attgaac                                            27

<210> SEQ ID NO 17
<211> LENGTH: 22
<212> TYPE: DNA
<213> ORGANISM: Artificial Sequence
<220> FEATURE:
<223> OTHER INFORMATION: Rev10 Primer

<400> SEQUENCE: 17
cttcccagcc tgggcatcct tg                                                 22

<210> SEQ ID NO 18
<211> LENGTH: 21
<212> TYPE: DNA
<213> ORGANISM: Artificial Sequence
<220> FEATURE:
<223> OTHER INFORMATION: Rev9 Primer

<400> SEQUENCE: 18
cttctttggc tggggagagg a                                                  21

<210> SEQ ID NO 19
<211> LENGTH: 23
<212> TYPE: DNA
<213> ORGANISM: Artificial Sequence
<220> FEATURE:
<223> OTHER INFORMATION: MP9ER Primer

<400> SEQUENCE: 19
ctcccaggac aggcacaaac acg                                                23
```

SIGNATURE FOR THE DIAGNOSIS OF CANCER AGGRESSIVENESS AND GENETIC INSTABILITY

CROSS REFERENCE TO RELATED APPLICATIONS

This application is a Continuation-In-Part of PCT International Application No. PCT/EP2010/067401 filed on Nov. 12, 2010, which claims the benefit of Patent Application No. 09306096.0, filed in European Patent Office on Nov. 13, 2009. The entire contents of all of the above applications is hereby incorporated by reference into the present application.

FIELD OF THE INVENTION

The present invention is in the field of cancer management, including diagnosis of aggressiveness and genetic instability of said breast cancer, and selection of an appropriate treatment. The invention is based on the finding that overexpression of POLQ is highly related to aggressiveness of a tumor, and thus to survival of the patient. The same overexpression is also correlated to genetic instability, which may then be used to kill tumor cells. Radiotherapy, for instance, is more efficacious on DNA which is already damaged. Likewise, DNA repair inhibitors may prevent repair of DNA breaks, thus leading to tumor cell death.

BACKGROUND ART

Cancer is a multi-faceted disease in which a group of cells display uncontrolled growth, invasion that intrudes upon and destroys adjacent tissues, and sometimes metastasis, or spreading to other locations in the body via lymph or blood. These three malignant properties of cancers differentiate them from benign tumors, which do not invade or metastasize.

There are a number of methods currently used to treat each type of cancer, including surgery, radiotherapy, and chemotherapy. Successful cancer therapy is directed to the primary tumor and to any metastases, whether clinically apparent or microscopic.

The selection of an appropriate treatment is crucial for the patient. It is essential to know when to use immediately a heavy and aggressive treatment protocol in order to prevent extension of an aggressive cancer. In contrast, performing a heavy and aggressive treatment when it is not necessitated by the tumor carried by the patient is also disadvantageous for the patient. Indeed, heavy and aggressive treatments always lead to adverse toxicities that may significantly affect the patient's quality of life. In addition, such heavy and aggressive treatments are usually very costly, and should thus be performed only when it is necessary.

Currently, treatment selection for solid tumors is based on tumor staging, which is usually performed using the Tumor/Node/Metastasis (TNM) test from the American Joint Committee on Cancer (AJCC). The TNM system assigns a number based on three categories. "T" denotes the tumor size, "N" the degree of lymphatic node involvement, and "M" the degree of metastasis. The broader stage of a cancer is usually quoted as a number I, II, III, IV derived from the TNM value grouped by prognosis; a higher number indicates a more advanced cancer and likely a worse outcome.

It is commonly acknowledged that, while this test and staging system provides some valuable information concerning the stage at which solid cancer has been diagnosed in the patient, it is imprecise and insufficient. In particular, it fails to identify the earliest stages of tumor progression. In addition, the TNM test does not give information on the tumor aggressiveness and its usefulness for prognosis is thus limited. Finally, it is limited to solid tumors. Liquid tumors on the other hand are mostly characterized by the identification of cytogenetic alterations.

Several protein and genetic markers have been described in an attempt to refine prognostic information. In particular, gene expression analysis has allowed the identification of multi-gene prognostic signatures. However, the information gathered in different studies have often proven confusing (see e.g. Lenz, *Gastrointest Cancer Res*, 1(4 Suppl 2): S29-32, 2007; Walther et al., *Nat Rev Cancer*, 9(7): 489-99, 2009). Overlap between different signatures for the same cancer, for example, can be poor. The robustness of multi-gene signatures is also questionable because they essentially concern cell cycle- or proliferation-associated genes and therefore add nothing to standard clinico-pathological staging. In addition, each signature is limited to a specific type of cancer. None of these markers is thus in routine clinical use.

There is a real need for better prognosis tests of cancer, not only to improve patient global survival, but also to improve their quality of life and to keep aggressive and costly chemotherapies for patients who will really benefit from them. In particular, there is a need for a single-gene prognosis marker which can be used reliably for the prognosis of as many types of cancers as possible.

In normal cell proliferation, DNA replication is performed by 3 DNA polymerases known as replicating polymerases (POLA, POLD and POLE). However, 10 other DNA polymerases have been identified in human cells, which are known as specialized polymerases and which functions are still largely unknown. These specialized polymerases appear to have been maintained through evolution because of their ability to process despite of DNA damage. It also appears that these polymerases are very mutagenic and that their activity is tightly controlled.

POLQ (also known as POL theta or POLθ) is one of these specialized DNA polymerases, and contains a helicase domain in its N-terminal portion and a polymerase domain in its C-terminus. Although the function of this particular specialized DNA polymerase is still largely unknown, it appears to be involved in maintenance of genome stability and in DNA repair (Seki et al., *EMBO J*, 23: 4484-4494, 2004; Masuda et al., *Proc. Natl. Acad. Sci. U.S.A.*, 102: 13986-13991, 2005, Yoshimura et al., *Mol. Cell*, 24: 115-125, 2006), but also in the licensing and initiation of DNA replication, probably by facilitating the firing of the replication origins (unpublished data). POLQ expression has been analyzed in various tumors (Kawamura et al., *Int J Cancer*, 109: 9-16, 2004).

The inventors analyzed the variation of expression of the POLQ gene in tumor versus normal tissues and compared these data with disease progression and clinical features. They showed that POL Q was significantly overexpressed in tumor tissues. In addition, they demonstrated that POLQ deregulated expression contributed actively to tumor progression. Indeed, POLQ overexpression leads to genetic instability and notably DNA damage.

DESCRIPTION OF THE INVENTION

The present inventors have shown that POLQ is overexpressed in various different cancers and this overexpression gives information about the patient prognosis. For example, POLQ was found to be overexpressed in breast tumors, as well as in lung cancers. This overexpression was associated to the patient survival, whatever the survival term examined (overall survival, relapse-free survival, disease-free survival). Remarkably, the statistical link between POLQ and patient survival is independent of the tumor stage and of the treatment.

The present invention thus provides a method for diagnosing the aggressiveness of a cancer in a patient. According to the method of the invention, elevated expression levels of the POLQ gene indicate aggressiveness of said cancer.

Therefore, the present invention provides a method for diagnosing aggressiveness of a cancer in a patient from a cancer sample of said patient, comprising:
  a) measuring in vitro the expression level of the POLQ gene and the expression level of a control gene in said patient cancer sample,
  b) calculating for said POLQ gene an expression level ratio of the expression level of POLQ to the expression of the said control gene in said patient cancer sample,
  c) comparing the said POLQ expression level ratio to a corresponding threshold value, and
  d) diagnosing cancer aggressiveness if the said POLQ expression level ratio is superior to its corresponding threshold value.

In particular, in one embodiment, the method of the invention may be used for prognosing the survival of a patient with a high number of metastatic lymph nodes. In this embodiment, a high level of POLQ expression in a patient with a high number of metastatic lymph nodes indicates aggressiveness of the tumor, and results in poor survival prognosis, whereas low level of POLQ expression in a patient with a high number of invaded lymph nodes is associated to a much better diagnosis. A low number of metastatic lymph nodes may be defined, for example, as a invaded lymph node count equal to 1 or less, while a high number of metastatic lymph nodes may be defined as a invaded lymph node count equal to 2 or more.

In another embodiment, the method of the invention may be used for prognosing the survival of a patient which has a tumor expressing a p53$^{wt}$ cDNA (the sequence does not contain any mutations by reference to sequence NC 000017-9 from GenBank). In this embodiment, a high level of POLQ expression in a patient with a tumor expressing a p53$^{wt}$ cDNA indicates aggressiveness of the tumor, and results in poor survival prognosis, whereas low level of POLQ expression in a patient with a tumor expressing a p53$^{wt}$ cDNA is associated to a much better diagnosis. Indeed, the inventors have shown that a low level of POLQ expression in a patient with a tumor expressing a p53$^{wt}$ cDNA is associated with a probability of survival of 98%. In another aspect, the method of the invention allows for the detection of cancer cells displaying genetic instability, i.e. DNA damage or "replicative stress" caused by a perturbation of origin firing. Deregulated expression of POLQ leads to increased mitotic abnormalities, such as chromatid breaks, chromosomal end-to-end fusions, dicentric chromosomes, and other abnormalities, thus triggering constitutive activation of the γH2AX-ATL-CHK2 DNA damage checkpoint. Thus POLQ overexpression leads to DNA damage and chromosome instability.

Therefore, the present invention provides a method for diagnosing genetic instability in a cancer in a patient from a cancer sample of said patient, comprising:
  a) measuring in vitro the expression level of the POLQ gene and the expression level of a control gene in said patient cancer sample,
  b) calculating for said POLQ gene an expression level ratio of the expression level of POLQ to the expression of the said control gene in said patient cancer sample,
  c) comparing the said POLQ expression level ratio to a corresponding threshold value, and
  d) diagnosing cancer genetic instability or replication stress if the said POLQ expression level ratio is superior to its corresponding threshold value.

It is understood that both methods can be combined. Therefore, in a further aspect, the invention relates to a method for diagnosing the aggressiveness of a cancer in a patient and for the detection of cancer cells displaying genetic instability. The method of the invention thus presents the advantage of allowing the detection of a genetic event associated with both a bad survival prognosis and genetic instability. As used herein, the terms "cancer" and "cancerous" refer to or describe the physiological condition in mammals that is typically characterized by unregulated cell growth. The terms "cancer" and "cancerous" as used herein are meant to encompass all stages of the disease. Thus, a "cancer" as used herein may include both benign and malignant tumors. Examples of cancer include but are not limited to, carcinoma, lymphoma, blastoma, sarcoma, and leukemia or lymphoid malignancies. More particular examples of such cancers include, but not limited to, squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer and gastrointestinal stromal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, superficial spreading melanoma, lentigo maligna melanoma, acral lentiginous melanomas, nodular melanomas, multiple myeloma and B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); hairy cell leukemia; chronic myeloblastic leukemia; and post-transplant lymphoproliferative disorder (PTLD), as well as abnormal vascular proliferation associated with phakomatoses, edema (such as that associated with brain tumors), Meigs' syndrome, brain, as well as head and neck cancer, and associated metastases.

In a particular embodiment, cancers that can be prognosed using the method of the invention include any type of cancer except colon cancer. In another embodiment, the methods of the invention can be used with any combination of 2, 3, 4 or more of the cancers listed above.

In a preferred embodiment, the methods of the invention are used to prognose a solid cancer. In a more preferred embodiment, the said solid cancer is lung cancer. In another more preferred embodiment, the said solid cancer is breast cancer.

As used herein, the term "POLQ" refers to the human gene encoding the DNA polymerase theta (Entrez Gene ID number: 10721; mRNA sequence reference: NM_199420.3; protein sequence reference: NP_955452.3). In addition, the invention encompasses all the isoforms of the said POLQ gene. Isoform, as used herein, refers to all the different forms of the POLQ gene and may be produced by mutations, or may arise from the same gene by alternative splicing. A large number of isoforms are caused by single nucleotide polymorphisms or SNPs, small genetic differences between alleles of the same gene. These occur at specific individual nucleotide positions within a gene. Also included within this definition is the situation where different versions of messenger RNA are created from the same gene by employing different promoters, which causes transcription to skip certain exons. Thus, it is understood that the methods of the invention are not restricted to POLQ per se, but also encompass one or several POLQ isoforms. According to methods of the invention, the level of the expression of the POLQ gene and/or one or several of its isoforms is measured, and ratios of expression are calculated.

According to the present invention, "aggressiveness" of a cancer is intended to mean the propensity of said cancer to invade the neighboring tissues and to generate metastases and the rapidity with which said invasions may appear. Aggressiveness of the cancer is obviously correlated to survival, and the above method may be used for prognosing survival of the patient, in which case diagnosing of aggressiveness results in a bad survival prognosis and diagnosis of the absence of aggressiveness results in a good survival prognosis.

As used herein, "genetic instability" of a cancer is intended to mean the propensity of tumor cells of said cancer to suffer from DNA damage or "replication stress". Genetic instability is the hallmark of cancer in which DNA damage are more frequent. By "DNA damage", it is herein meant injury to DNA that affects the normal function of the DNA by causing covalent modification of the DNA, DNA breaks, or causing it to deviate from its normal double-helical conformation. DNA damage includes structural distortions which interfere with replication and transcription, as well as point mutations which can disrupt base pairs and can change the DNA sequence. In general, when a cell incurs DNA damage, the cell cycle is arrested at one of three checkpoints (G1/S, intra-S or G2/M). The cell cycle arrest can lead to the activation of DNA repair processes (in the case of relatively minor DNA damage), or result in the induction of apoptosis (in the case of catastrophic DNA damage).

DNA damage can be caused spontaneously by endogenous processes such as oxidation of bases and generation of DNA strand interruptions by reactive oxygen and free radicals produced from normal metabolism, methylation of bases, depurination, depyrimidination, mismatch of bases by DNA polymerases during DNA replication, etc. DNA damage can also be caused by environmental insults such as radiation (e.g., ultraviolet radiation, x-rays, gamma rays, ionizing radiation), natural toxins (e.g., plant toxins), synthetic toxins, drugs (e.g., cancer chemotherapy, radiation therapy), alkylating agents, etc. DNA damage can lead to or result from a variety of disorders, including hereditary genetic disorders and disorders as a result of exposure to environmental insults. DNA damage can also occur as a result of smoking (smoke including genotoxic aromatic compounds), leading to for example, heart disease, or as a result of therapies for other diseases, such as cancers (including lung cancer).

The above methods are performed using a cancer sample of the patient to be tested. In some cases, the methods according to the invention may further comprise a preliminary step of taking a cancer sample from the patient. By a "cancer sample", it is referred to a tumor tissue sample. Even in a cancerous patient, the tissue which is the site of the tumor still comprises non tumor healthy tissue. The "cancer sample" should thus be limited to tumor tissue taken from the patient. Said "cancer sample" may be a biopsy sample or a sample taken from a surgical resection therapy.

In addition, the methods according to the invention may comprise another preliminary step, between the taking of the sample from the patient and steps a) as defined above, corresponding to the transformation of the cancer sample (and optionally of the healthy tissue sample) into a mRNA (or corresponding cDNA) sample or into a protein sample, which is then ready to use for in vitro measuring of genes expression levels in step a). Preparation or extraction of mRNA (as well as retrotranscription into cDNA) or proteins from a tissue sample is only routine procedure well known to those skilled in the art.

Once a ready-to-use cancer mRNA (or corresponding cDNA) or protein sample is available, the measure of POLQ gene expression levels may be performed, depending on the type of transformation and the available ready-to-use sample, either at the mRNA (i.e. based on the mRNA content of the sample) or at the protein level (i.e. based on the protein content of the sample). In some embodiments, the expression levels of some of the genes may be measured at the mRNA level, while the expression levels of other genes are measured at the protein level. In this case, part of the cancer sample taken from the patient has been transformed into an mRNA (or corresponding cDNA) sample and another part has been transformed into a protein sample. In other embodiments, the expression levels of all tested genes are measured either at the mRNA or at the protein level.

When expression levels are measured at the mRNA level, it may be notably performed using well known technologies such as quantitative PCR or nucleic acid microarray technologies (including cDNA and oligonucleotide microarrays). These technologies are now used routinely by those skilled in the art and thus do not need to be detailed here. Examples of embodiments using quantitative PCR are described in the experimental section. Alternatively, any known or future technology permitting to assess genes expression levels based on mRNA contents may be used. For instance, tissue microarrays coupled to fluorescent in situ hybridization may be used. Tissue microarrays (also known as TMAs) consist of paraffin blocks in which up to 1000 separate tissue cores are assembled in array fashion to allow multiplex histological analysis. In the tissue microarray technique, a hollow needle is used to remove tissue cores as small as 0.6 mm in diameter from regions of interest in paraffin-embedded tissues such as clinical biopsies or tumor samples. These tissue cores are then inserted in a recipient paraffin block in a precisely spaced, array pattern. Sections from this block are cut using a microtome, mounted on a microscope slide and then analyzed by any method of standard histological analysis. Each microarray block can be cut into 100-500 sections, which can be subjected to independent tests. Tests commonly employed in tissue microarray include immunohistochemistry, and fluorescent in situ hybridization. For analysis at the mRNA level, tissue microarray technology may be coupled to fluorescent in situ hybridization.

When expression levels are measured at the protein level, it may be notably performed using specific antibodies, in particular using well known technologies such as western blot, ELISA or ELISPOT, antibodies microarrays, or tissue microarrays coupled to immunohistochemistry.

The comparison of the expression levels of the measured genes in said patient's cancer sample is made by calculating an expression level ratio of the expression level of the POLQ gene to the expression level of a control gene in said patient's cancer sample, and by comparing the obtained expression level ratio to a corresponding threshold value. Said control gene, according to the present invention, is a gene which is expressed in all cell types. More specifically, the control gene according to the invention is a gene which is expressed in all the cells constituting the tissue which is the site of the tumor. In another aspect, the expression level of the control gene is not affected by the state of the cell, i.e. the control gene is expressed to the same level in a healthy cell and in a tumor cell. In a specific embodiment, the control gene is a housekeeping gene. A housekeeping gene is a gene expressed in all cell types, which provides a basic function needed for sustenance of all cell types. A list of human housekeeping genes may be found in Eisenberg et al. (*Trends in Genetics* 19: 362-365, 2003). A preferred housekeeping gene according to the invention is a gene selected in the group consisting of B2M, TFRC, YWHAZ, RPLO, 18S, GUSB, UBC, TBP, GAPDH, PPIA, POLR2A, ACTB, PGK1, HPRT1, IPO8 and HMBS. A further preferred housekeeping gene according to the invention is selected from the group consisting of IPO8, HMBS, GUSB, and UBC. Even more preferably, a housekeeping gene according to the invention is IPO8 or HMBS.

According to the present invention, a "threshold value" is intended to mean a value that permits to discriminate samples in which the expression level ratio of the gene of interest corresponds to an expression level of said gene of interest in the patient's cancer sample that is low or high. In particular, if a gene expression level ratio is inferior or equal to the threshold value, then the expression level of this gene in the patient's cancer sample is considered low, whereas if a gene expression level ratio is superior to the threshold value, then the expression level of this gene in the patient's cancer sample is considered high. For each gene, and depending on the method used for measuring the expression level of the genes, the optimal threshold value may vary. However, it may be easily determined by a skilled artisan based on the analysis of several control cancer samples in which the expression level (low or high) is known for this particular gene, and on the comparison thereof with the expression of a control gene, e.g. a housekeeping gene. In particular, the inventors determined that a unique threshold value of 15.8 is particularly useful. The inventors have shown that the patient survival is significantly decreased for expression level ratios above this value. This unique threshold value of 15.8 is specifically useful when the expression level of all genes is measured at the mRNA level using quantitative PCR.

The present invention further relates to a microarray dedicated to the implementation of the methods according to the invention, comprising at most 500, preferably at most 300, at most 200, more preferably at most 150, at most 100, even more preferably at most 75, at most 50, at most 40, at most 30, at most 20, at most 10 distinct probes, at least 1 of which specifically binds to POLQ mRNA (or corresponding cDNA) or protein.

In a preferred embodiment, said microarray is a nucleic acid microarray, comprising at most 500, preferably at most 300, at most 200, more preferably at most 150, at most 100, even more preferably at most 75, at most 50, at most 40, at most 30, at most 20, at most 10 distinct probes (thus excluding for instance pangenomic microarrays), at least 1 of which specifically hybridizes to POLQ mRNA (or corresponding cDNA). Said microarray may also contain at least one probe which specifically hybridizes to a housekeeping gene in addition to the probe specifically hybridizing to POLQ. In one embodiment, said housekeeping gene is selected in the group consisting of B2M, TFRC, YWHAZ, RPLO, 18S, GUSB, UBC, TBP, GAPDH, PPIA, POLR2A, ACTB, PGK1, HPRT1, IPO8 and HMBS. More preferentially, the housekeeping gene is selected from the group consisting of the IPO8, HMBS, GUSB, and UBC genes. Even more preferentially, the housekeeping gene is IPO8 or HBMS. According to the invention, a "nucleic microarray" consists of different nucleic acid probes that are attached to a substrate, which can be a microchip, a glass slide or a microsphere-sized bead. A microchip may be constituted of polymers, plastics, resins, polysaccharides, silica or silica-based materials, carbon, metals, inorganic glasses, or nitrocellulose. Probes can be nucleic acids such as cDNAs ("cDNA microarray") or oligonucleotides ("oligonucleotide microarray", the oligonucleotides being about 25 to about 60 base pairs or less in length).

Alternatively, in another embodiment, said microarray may be an antibodies microarray, comprising at most 500, preferably at most 300, at most 200, more preferably at most 150, at most 100, even more preferably at most 75, at most 50, at most 40, at most 30, at most 20, at most 10 distinct antibodies, at least 1 of which specifically bind to POLQ protein. Said microarray may also contain at least one antibody which specifically binds to a housekeeping protein, in addition to the antibody specifically binding to the POLQ protein. In one embodiment, said housekeeping protein is selected in the group consisting of the B2M, TFRC, YWHAZ, RPLO, 18S, GUSB, UBC, TBP, GAPDH, PPIA, POLR2A, ACTB, PGK1, HPRT1, IPO8 and HMBS proteins. In a preferred embodiment, said housekeeping protein is selected from the group consisting of the IPO8, HMBS, GUSB, and UBC proteins. In a more preferred embodiment, the housekeeping protein is the IPO8 or HBMS protein.

Alternatively to nucleic acid or antibody microarray technology, quantitative PCR may be used and amplification primers specific for the genes to be tested are thus also very useful for performing the methods according to the invention. The present invention thus further relates to a kit for diagnosing aggressiveness and genetic instability of a cancer in a patient from a cancer sample of said patient, comprising a dedicated microarray as described above or amplification primers specific for POLQ. Here also, when the kit comprises amplification primers, while said kit may comprise amplification primers specific for other genes, said kit preferably comprises at most 100, at most 75, 50, at most 40, at most 30, preferably at most 25, at most 20, at most 15, more preferably at most 10, at most 8, at most 6, even more preferably at most 5, at most 4, at most 3 or even 2 or one or even zero couples of amplification primers specific for other genes than POLQ. For example, said kit may comprise at least a couple of amplification primers for at least one housekeeping gene in addition to the primers for POLQ. In one embodiment, said housekeeping gene is selected in the group consisting of B2M, TFRC, YWHAZ, RPLO, 18S, GUSB, UBC, TBP, GAPDH, PPIA, POLR2A, ACTB, PGK1, HPRT1, IPO8 and HMBS. In a preferred embodiment, said housekeeping gene is selected from the group consisting of the IPO8, HMBS, GUSB, and UBC genes. In a more preferred embodiment, the housekeeping gene is IPO8 or HBMS.

As mentioned above, the ability of prognosing cancer evolution, which is linked to its aggressiveness, is very important for selecting a suitable treatment, since heavy and costly treatments with potentially severe adverse effects should be used, in addition to traditional surgical treatment, each time they are necessary, but only when they are necessary. The present invention thus also concerns a method for choosing a suitable treatment of cancer in a patient, comprising:
a) diagnosing or not aggressiveness of said cancer in said patient using the method according to the invention as described above, and
b) adding adjuvant radiotherapy or chemotherapy to surgical treatment if said cancer is diagnosed as aggressive in step a).

In addition to its prognostic value concerning aggressiveness of cancer, the inventors also found that the same test based on the analysis of the expression levels of POLQ also allows diagnosing the presence or absence of genetic instability, thus resulting in the above described method for diagnosing genetic instability. In particular, the present inventors have shown that deregulated expression of POLQ is associated with an increased frequency of DNA breaks. In one preferred embodiment, the method of the invention is thus used to diagnose DNA breaks.

Such genetic instability, and notably the increased frequency of DNA breaks, may have consequences concerning the selection of an adjuvant therapy. In particular, while genetic instability may favor tumor cells mutations and thus deregulation of proliferation and adhesion, the presence of DNA damage might also be used against tumor cells. Indeed, for continued proliferation, those DNA breaks have to be repaired, and cells with a high number of DNA damage are usually prone to cell death. As a result, while radiotherapy may not be efficient in all circumstances, its efficiency on tumor cells that already present an increased frequency of DNA breaks may be improved. For example, radiotherapy may be highly efficient against the POLQ-overexpressing tumor cells identified by the method of the invention, because these cells contain high levels of DNA breakage and chromosomal instability. In the same manner, the use of DNA repair inhibitors might permit to freeze DNA breaks and lead to tumor cells death.

Indeed, the inventors have shown that the inhibition of DNA repair leads to a decreased viability of POLQ-overexpressing cells. As shown in the experimental examples, POLQ-overexpressing cells show increased sensitivity to DNA repair inhibitors. More generally, the inventors have shown that the inhibition the DNA damage checkpoint (DDC) or DNA metabolism leads to a decreased viability of POLQ-overexpressing cells. For example, cells affected in the Chk2 kinase activity are unable to detect the POLQ overexpression-induced DNA lesions and/or stop the cell cycle in response to the said lesions. Likewise, POLQ-overexpressing cells show increased sensitivity to DDC or nucleotide metabolism inhibition.

The present invention thus also concerns a method for prognosing the efficiency of radiotherapy or DNA repair inhibitors in the treatment of cancer in a patient, comprising:
 a) diagnosing or not genetic instability in said cancer in said patient using the method according to the invention as described above, and
 b) prognosing efficiency of radiotherapy or DNA repair or DNA damage checkpoint or DNA replication licensing/initiation inhibitors if genetic instability has been diagnosed in step a).

According to the invention, a "DNA repair inhibitor" is intended to mean a molecule that is able to inhibit repair of DNA breaks, in particular double stranded DNA breaks. While this expression should not be understood as limitative, examples of DNA repair inhibitors include inhibitors of DNA repair protein PARP (see e.g. WO 2004080976, WO 2005/053662, WO 2009/046205), inhibitors of histone deacetylase, such as those described in PCT application WO 2008/082856, and inhibitors of DNA polymerase β (see WO2007001684). A "DDC inhibitor" is a molecule which is capable of blocking the activity of any of the proteins involved in the DNA damage checkpoint. Examples of such proteins include ATM/ATR, Chk2 and Chk1. A "DNA replication licensing/initiation inhibitor". is a molecule capable of blocking the activity of any of the proteins involved in DNA replication licensing, such as Cdt1, Cdc6, Mcm1-7, and other known to the skilled person. Nucleotide metabolism inhibitors", as used herein, include all compounds which result in an imbalance of the nucleotide pools, because said nucleotide metabolism inhibitors are e.g. nucleotide analogues (ex: 6TG) or because they inhibit nucleotide biosynthesis enzymes (ex: HU).

In another embodiment, the present invention thus also covers a method for isolating new compounds capable of inhibiting DNA repair, DNA damage signaling or nucleotide metabolism, said method comprising the following steps:
 a) contacting a compound with a cell overexpressing POLQ or with a cell which does not overexpress POLQ, and
 b) assaying whether the compound affects the viability of the POLQ-overexpressing cell more than the viability of the cell not overexpressing POLQ.

The cell overexpressing POLQ can be any type of cell wherein the expression of POLQ is deregulated, whereas the cell which does not overexpress POLQ is a cell in which the regulation of the POLQ expression is maintained. For example, the said cell overexpressing POLQ can be obtained by transfection of a host cell with a backbone vector carrying the POLQ gene or cDNA under the control of a strong ubiquitous promoter. In this case, said cell is advantageously the said host cell transfected with the same backbone vector, wherein said vector does not contain the POLQ insert.

In yet another aspect, the invention also relates to the use of one or more DNA repair, DNA damage signaling or nucleotide metabolism inhibitors for the preparation of a medicament intended for the treatment of cancer in patients whose tumor over-expresses POLQ. According to the present invention, a gene is considered as "overexpressed" in a cancer sample if the ratio of the expression level of said gene to the expression level of a control gene in said cancer sample is superior to a threshold value as defined above. In a particular embodiment, said threshold value may be 15.8.

The present invention also relates to a method for treating a patient suffering from a cancer overexpressing POLQ, comprising subjecting said patient to radiotherapy and/or administering to said patient an effective amount of one or more DNA repair inhibitors.

FIGURES LEGENDS

The patent or application file contains at least one color drawing. Copies of this patent or patent application publication with color drawing will be provided by the USPTO upon request and payment of the necessary fee.

FIG. 1. Relative expression of DNA polymerase genes in breast tumors from set 1 (France, n=105). mRNA expression ratios for tumor (T) and normal (N) breast samples (T/N) were calculated (expression levels were previously normalized in relation to control genes). T/N>1 and <1 indicate higher and lower expression levels in tumors compared to pooled normal tissues, respectively. The p-values from the bilateral exact binomial test are given uncorrected; the significance level is evaluated using the Benjamini 2001 procedure for an overall FDR of 0.05. The patient samples indicated by the x axis are classified in the same order for every panel. + and − stand for higher and lower expression in the tumor (T) compared to the normal (N) tissues, respectively. For graph representation T/N values lower than 1 were transformed into the inverse N/T values.

Figure 2:
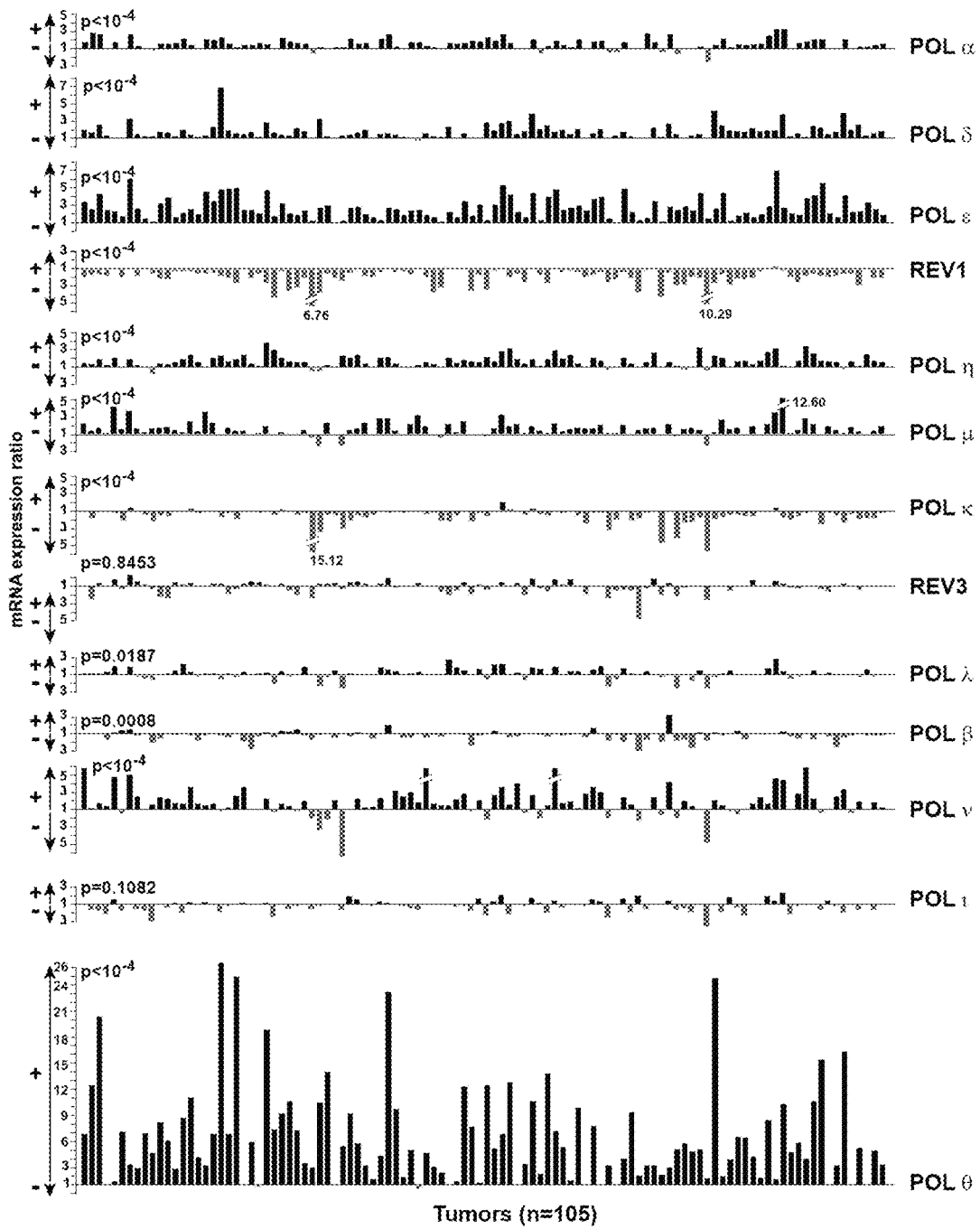

FIG. 2. Relative expression of DNA polymerase genes in breast tumors from set 2 (France, n=101). mRNA expression ratios for tumor (T) and normal (N) breast samples (T/N) were calculated (expression levels were previously normalized in relation to control genes). T/N>1 and <1 indicate higher and lower expression levels in tumors compared to pooled normal tissues, respectively. The p-values from the bilateral exact binomial test are given uncorrected; the significance level is evaluated using the Benjamini 2001 procedure for an overall FDR of 0.05. The patient samples indicated by the x axis are classified in the same order for every panel. + and − stand for higher and lower expression in the tumor (T) compared to the normal (N) tissues, respectively. For graph representation T/N values lower than 1 were transformed into the inverse N/T values.

Figure 3:
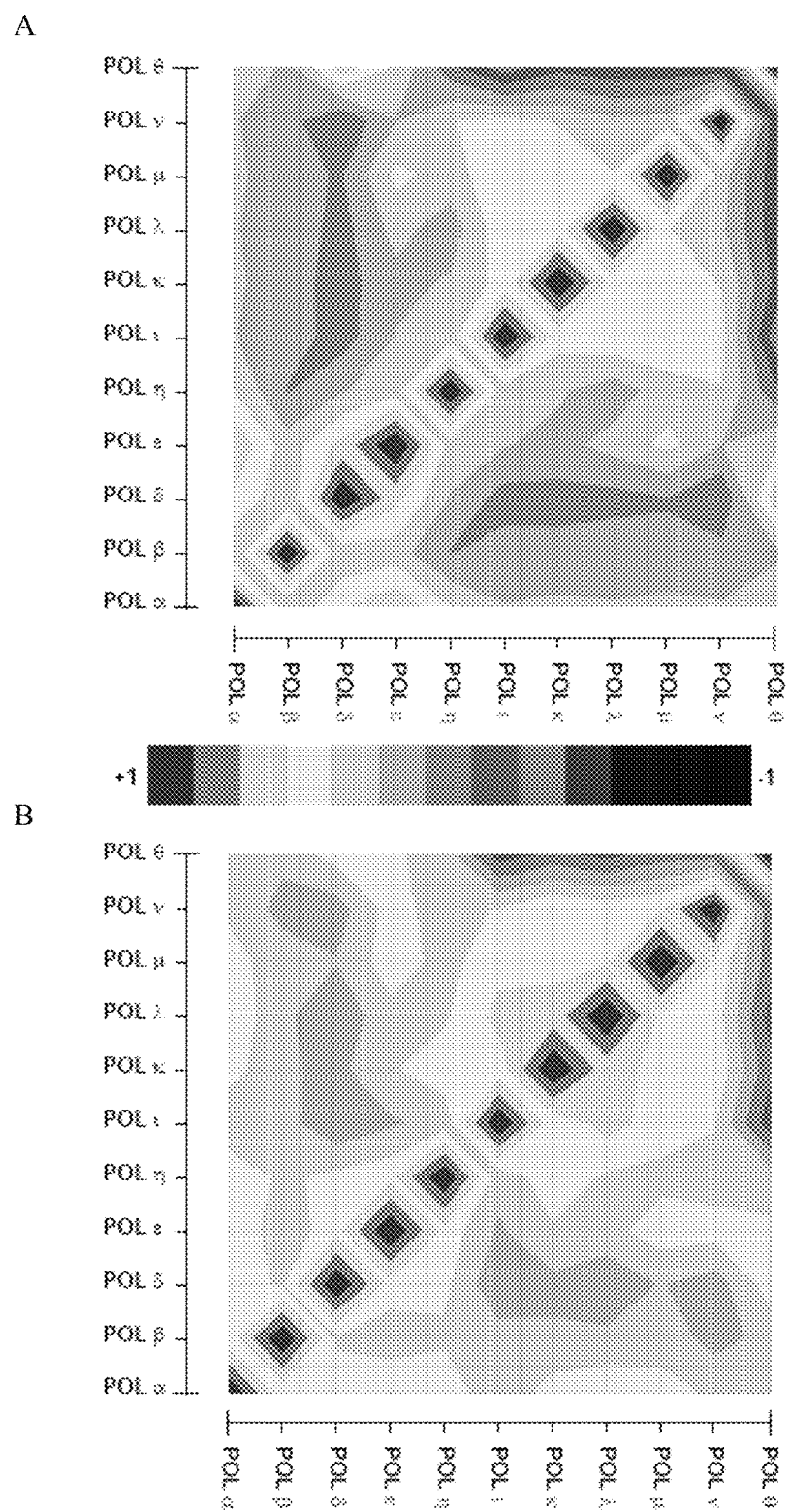

FIG. 3. Gene to gene comparison of relative gene expression in tumors. Graphical display of all pair wise correlations between the expression of the DNA polymerases in French breast tumors (Non parametric Spearman's correlation; (A) set 1 (n=105); (B) set 2 (n=101)). The closer to 1 the Spearman rho coefficient is (illustrated by a red or yellow zone at the intersection of horizontal and vertical axis), the greater the association between the expression of the two genes considered. Conversely, rho values lower than 1 (illustrated by a green zone) indicates that the expressions under comparison are independent from each other.

Figure 4:
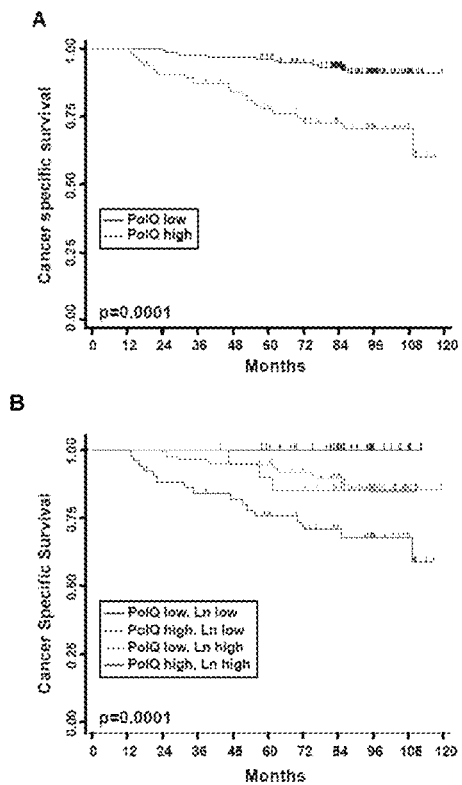

FIG. 4. Effect of POLQ gene expression level on cancer-specific survival of patients. (A) Kaplan-Meier survival of breast cancer patients, according to level of DNA POLQ expression in the primary tumor. Patients from the French cohort (n=203 instead of 206, 3 samples without POLQ determination being discarded). p values taken from each log-rank test are indicated. (B) Kaplan-Meier survival of pair wise comparison between POLQ gene expression in the primary breast tumor and the number of positive lymph nodes. Patients from the French cohort (n=203)). Log-rank chi-square (×2) and p values are given. Pq stands for POLQ and Ln for positive lymph node.

Figure 5:
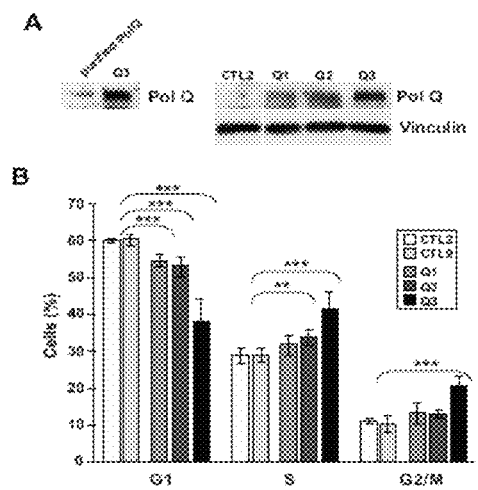

FIG. 5. Cell homeostasis of POLQ over-expressing clones (A) Validation of clones stably over-expressing POLQ. Cell extracts (100 µg) from control cells stably transfected with an empty vector (CTL2) as well as from clones stably transfected with POLQ cDNA (Q1, Q2 and Q3) were separated on 5% SDS-PAGE, electro-transferred to PVDF membranes and analyzed by immunoblotting with affinity-purified antibodies anti-POLQ (15) and anti-vinculin as an internal control of loading. Purified POLQ (50 ng) is used as a control of size; (B) Consequences on the cell cycle. The number of cells in each phase of the cell cycle was determined by flow cytometry after DNA staining by propidium iodide. At least 3 independent experiments were analyzed. The mean and standard error were determined and p-values were calculated by Student's t-test.

Figure 6:
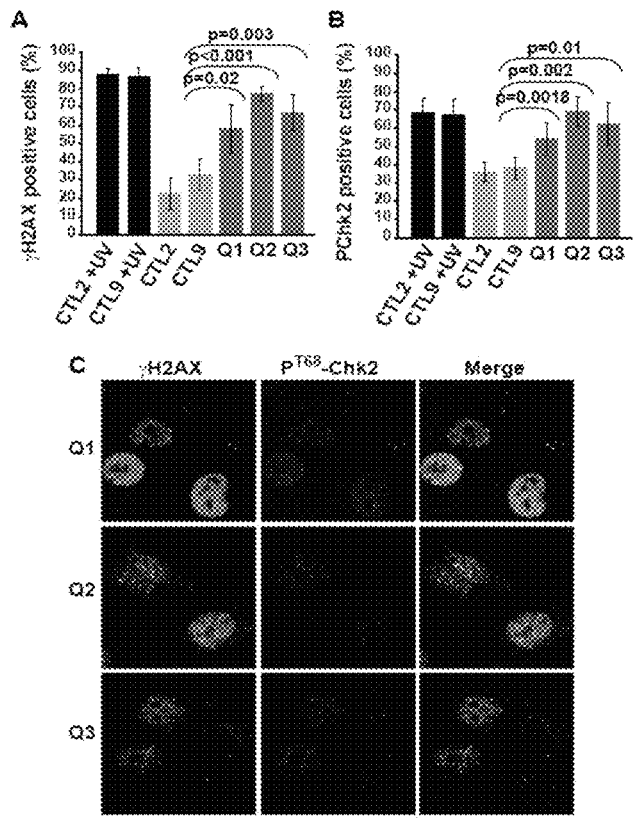

FIG. 6. ATM-CHK2 DNA damage checkpoint in POLQ over-expressing clones Quantification of the average number of cells positive to γ-H2AX (A) and PT68-CHK2 (B) staining Control (CTL) clones treated with UV (10 J·m-2) were used as positive controls. For quantification, a minimum of 100 cells were analyzed in at least 3 independent experiments. The mean and standard error were determined and p-values were calculated by Student's t-test; (C) Representative confocal microscopy images of cells over-expressing POLQ (Q1, Q2, Q3).

Figure 7:
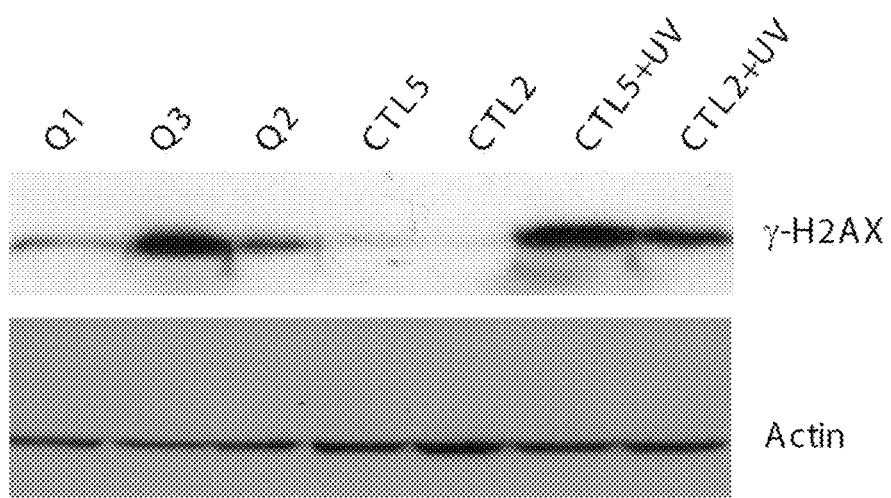

FIG. 7. γ-H2AX detection. 250,000 sub-confluent cells were harvested then sonicated. Total protein extract were resolved by electrophoresis on a 15% SDS polyacrylamide gel. The gel was transferred to a Hybond-P membrane (Amersham, Arlington Heights, Ill.), which was probed with monoclonal anti-H2AX antibody (Upstate, Lake Placid, N.Y.) overnight at 4° C. Horseradish peroxidase-goat anti-mouse antibody was used as the secondary antibody (Sigma, St. Louis, Mo.). The membrane was then incubated with enhanced chemiluminescence reagent (Amersham). Equivalent amounts of loaded extracts were assessed by immunoblotting the membrane with an anti-actin antibody.

Figure 8:
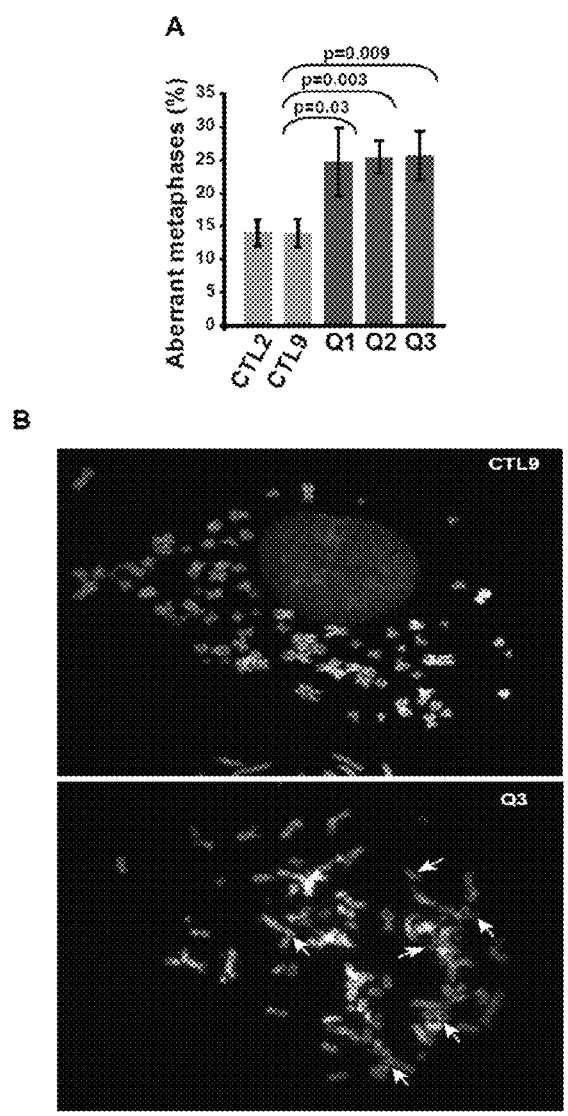

FIG. 8. DNA breaks and chromosomal abnormalities in POLQ over-expressing clones (A) Quantification of aberrant metaphases in control clones (CTL2 and CTL9) and in clones over-expressing POLQ (Q1, Q2 and Q3). Cells were collected 3 hours after colcemid treatment and metaphase spreads were prepared. For quantification, a minimum of 100 metaphases were analyzed in 3 independent experiments. The mean and standard error were determined and p-values were calculated by Student's t-test; (B) Representative microscopy images of metaphase spreads from CTL9 and Q3 clones. Arrows indicate chromosomal abnormalities.

Figure 9:
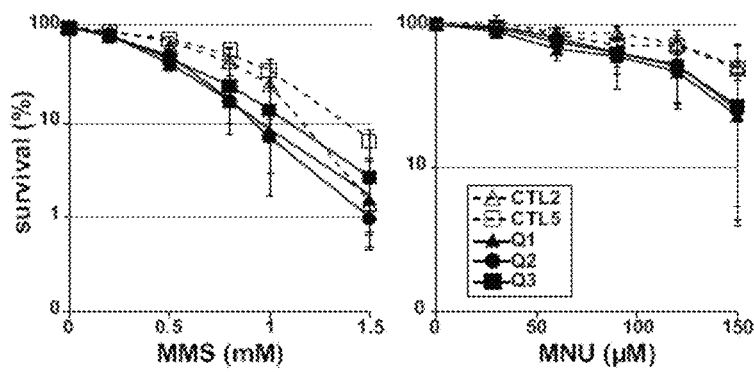

FIG. 9. Sensitivity to alkylating agents. Drug sensitivity was determined by clonogenic assay. Sensitivity of POLQ overexpressing (Q1, Q2, Q3) and isogenic control (CTL2, CTL5) cells to methyl methanesulfonate (MMS) and N-methyl-N-nitrosourea (MNU). Survival is expressed as the relative plating efficiency of treated cells to the controls. The doses of MMS and MNU are displayed on the x axis in a linear scale, while the fractions of surviving colonies are on the y axis in a logarithmic scale. Results are the mean+/−SD of at least three separate experiments performed in duplicate.

Figure 10:
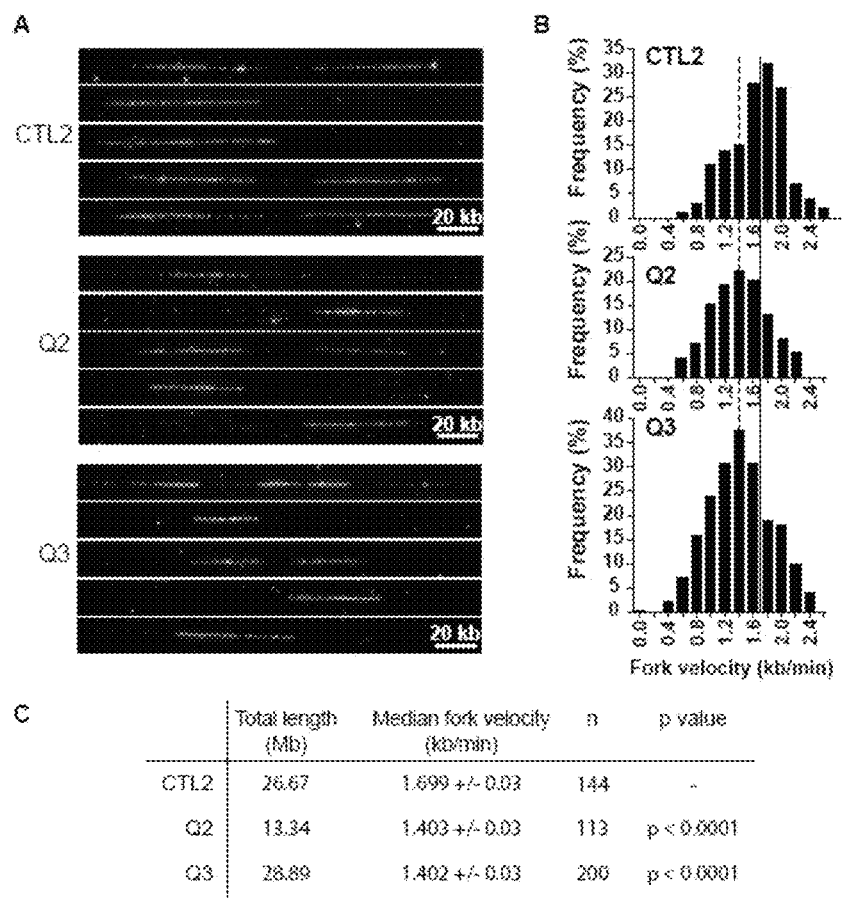

FIG. 10. DNA replication fork velocity in cells over-expressing POLQ (A) Representative image of a combed and immunostained DNA fiber in control cells or cells over-expressing POLQ; (B) Histograms showing replication fork velocity distribution in a control clone (CTL2) and in two clones over-expressing POLQ (Q2 and Q3); (C) Total length is the sum in Mb of all DNA fibers that were studied for each clone; "n" is the number of tracks of IdU and CldU scored in each clone. The median value of the population is given in kb/min. The uncertainty of median replication fork velocity is given in units of median absolute deviation. Mann-Whitney test was applied to compare Q2 and Q3 data sets with the control of the experiment, CTL2.

Figure 11:
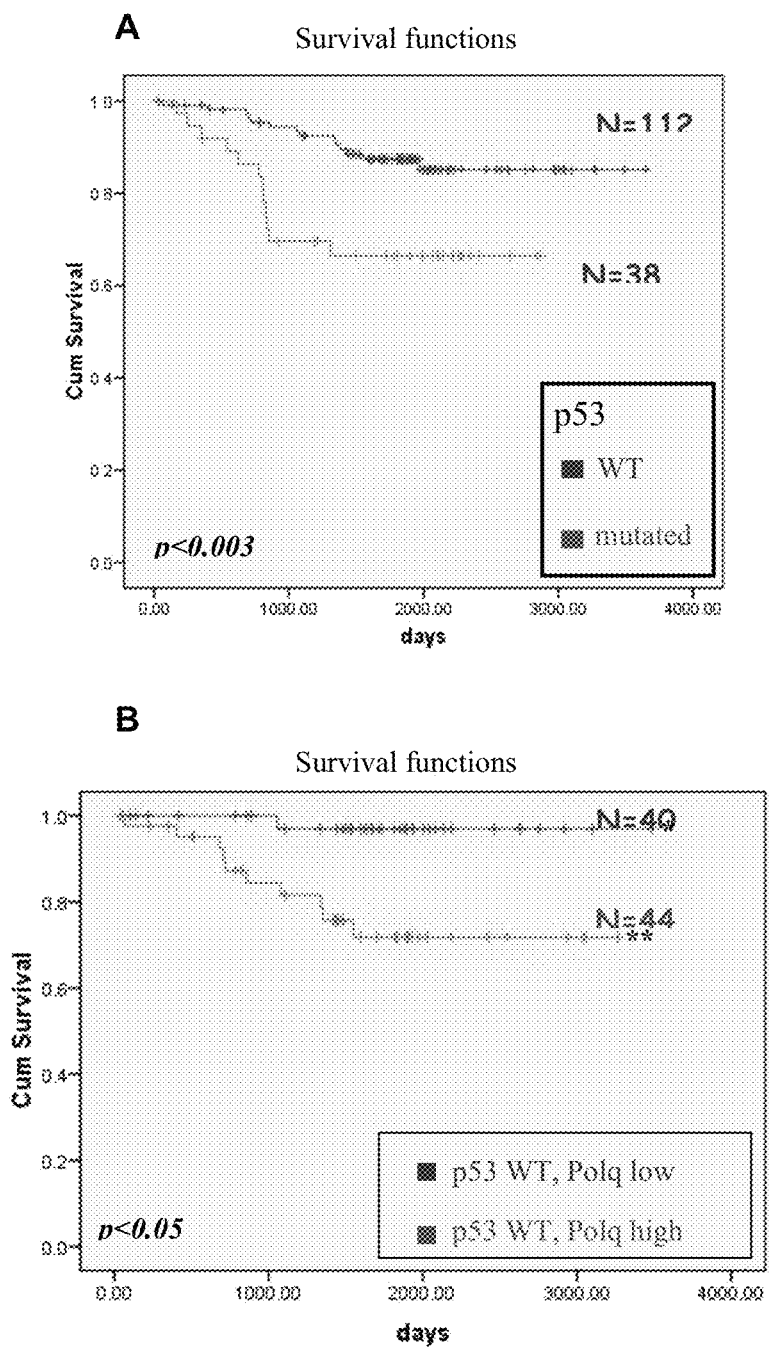

FIG. 11. Effect of POLQ gene expression level on p53-specific survival of patients. (A) Kaplan-Meier survival of breast cancer patients (n=150), according to the status of the p53 gene (wild-type vs mutated cDNA sequence). To compare these survival curves, the log-rank test was used. This test calculates a p-value testing the null hypothesis that the survival curves are identical in the two populations. p value taken from the log-rank test is indicated. (B) Kaplan-Meier survival of breast cancer patients with p53$^{wt}$ tumors (n=84) according to the level of expression of POLQ. To compare these survival curves, the log-rank test was used. This test calculates a p-value testing the null hypothesis that the survival curves are identical in the two populations. The p value is given.

Figure 12:
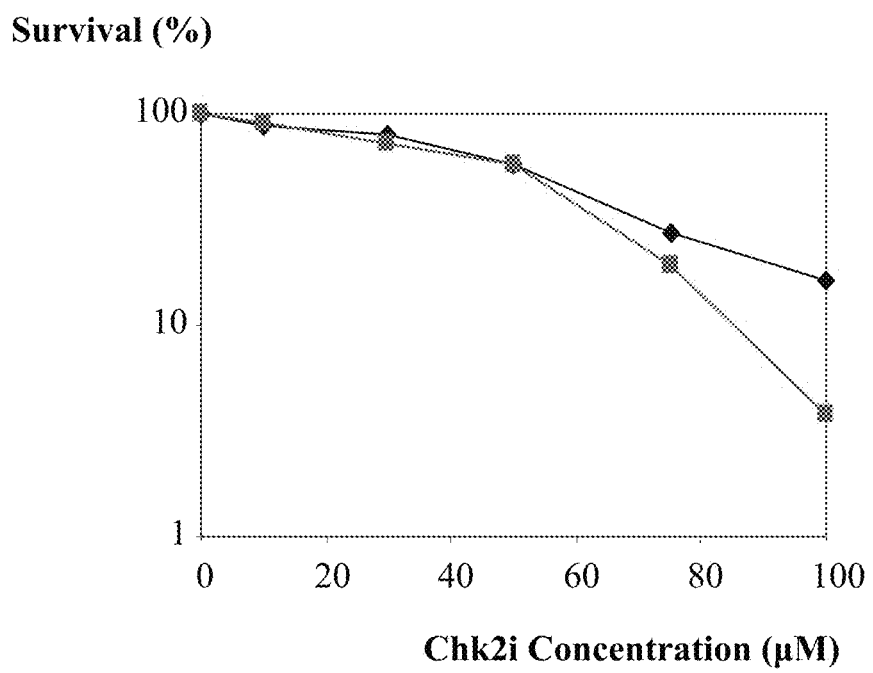
Figure 12:
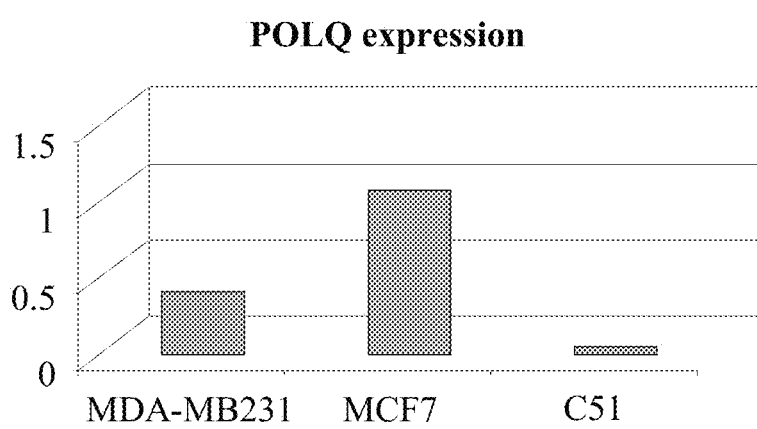

FIG. 12. Effect of POLQ gene expression level on sensitivity to a Chk2 inhibitor. (A) MCF7 cells show a higher sensitivity to Chk2 inhibitor II Hydrate (Sigma RefC3742) than MDA-MB231 cells. Survival is determined in a clonogenic assay. MCF7: squares; MDA-MB231: diamonds (B) POLQ expression is higher in MCF7 than in MDA-MB231. Gene expression levels are assayed by RT-PCR. C51 is a normal breast cell line.

Figure 13:
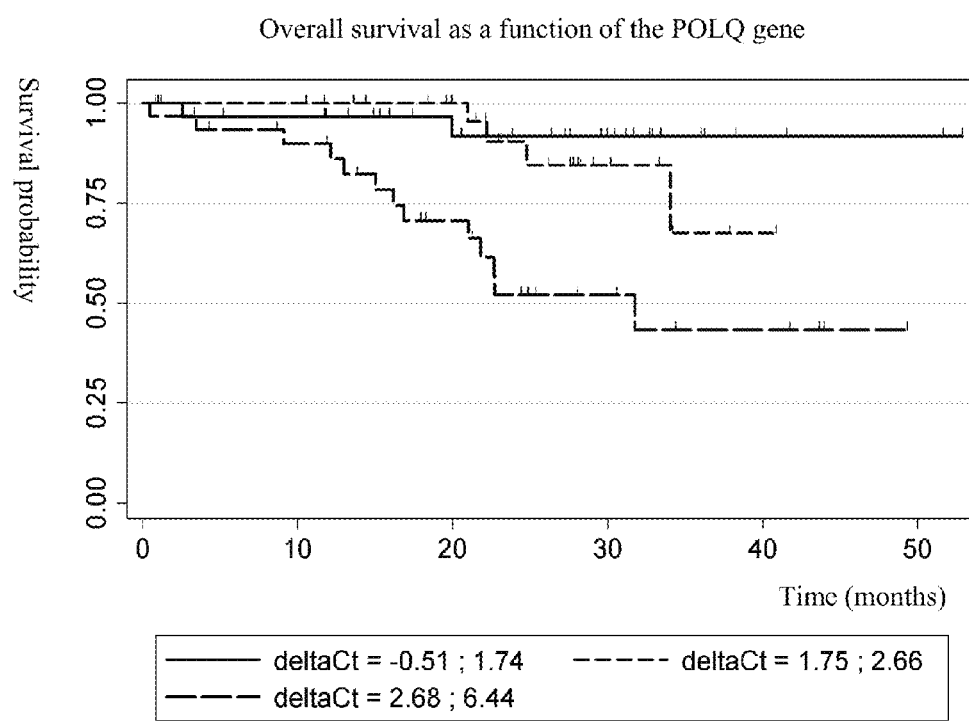
Figure 13:
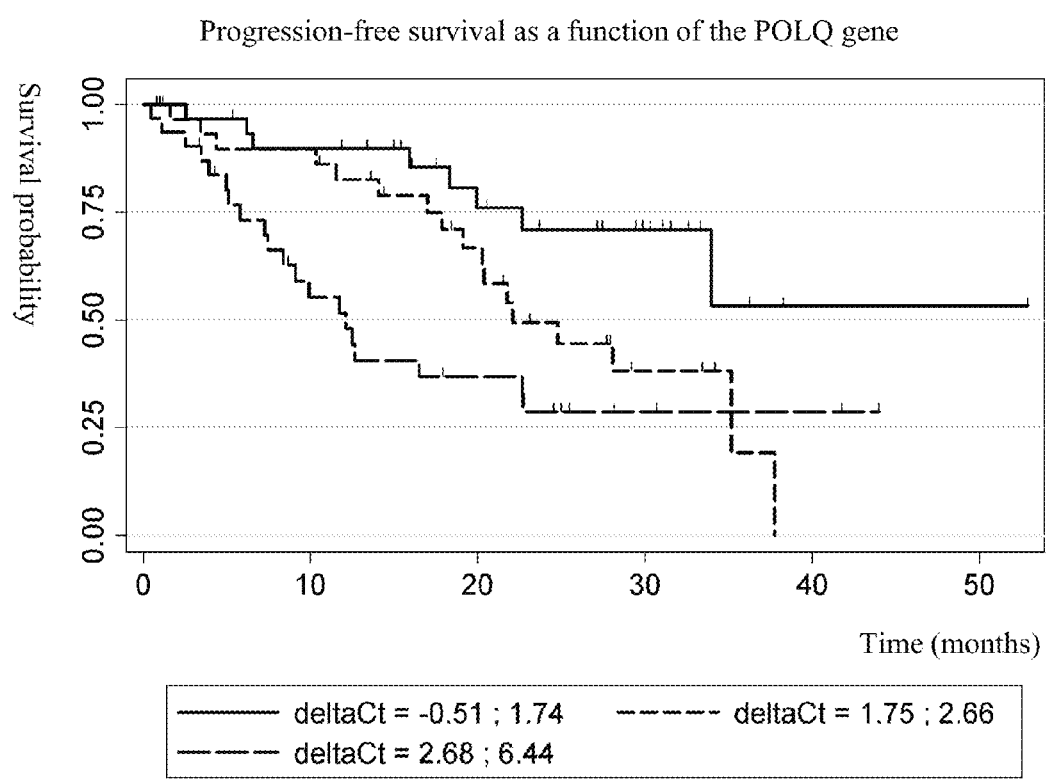
Figure 13:
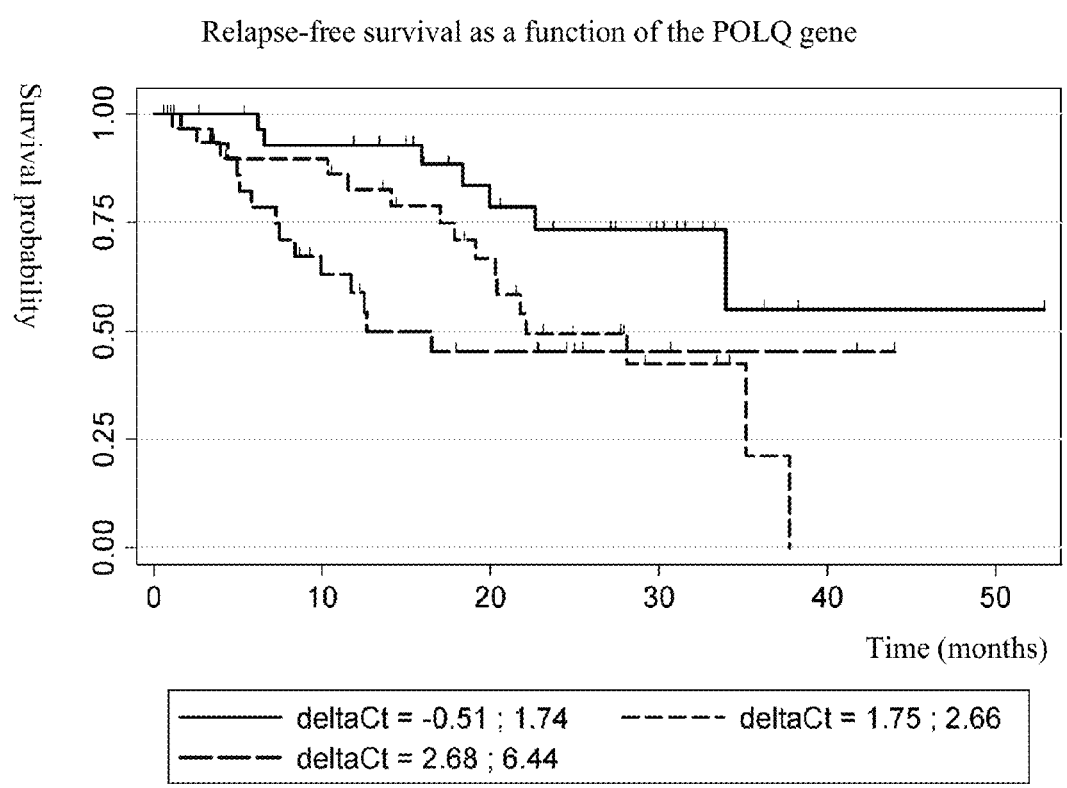

FIG. 13. Effect of POLQ gene expression level on lung cancer-specific survival of patients. (A) Kaplan-Meier overall survival of pulmonary adenocarcinoma patients, according to level of DNA POLQ expression in the primary tumor compared to adjacent normal tissue. Patients: n=93; p values taken from each log-rank test are indicated. (B) Kaplan-Meier progression-free survival of pulmonary adenocarcinoma patients, according to level of DNA POLQ expression in the primary tumor compared to adjacent normal tissue. Patients:

n=93; p values taken from each log-rank test are indicated. (C) Kaplan-Meier relapse-free survival of pulmonary adenocarcinoma patients, according to level of DNA POLQ expression in the primary tumor compared to adjacent normal tissue. Patients: n=93; p values taken from each log-rank test are indicated.

Figure 14:
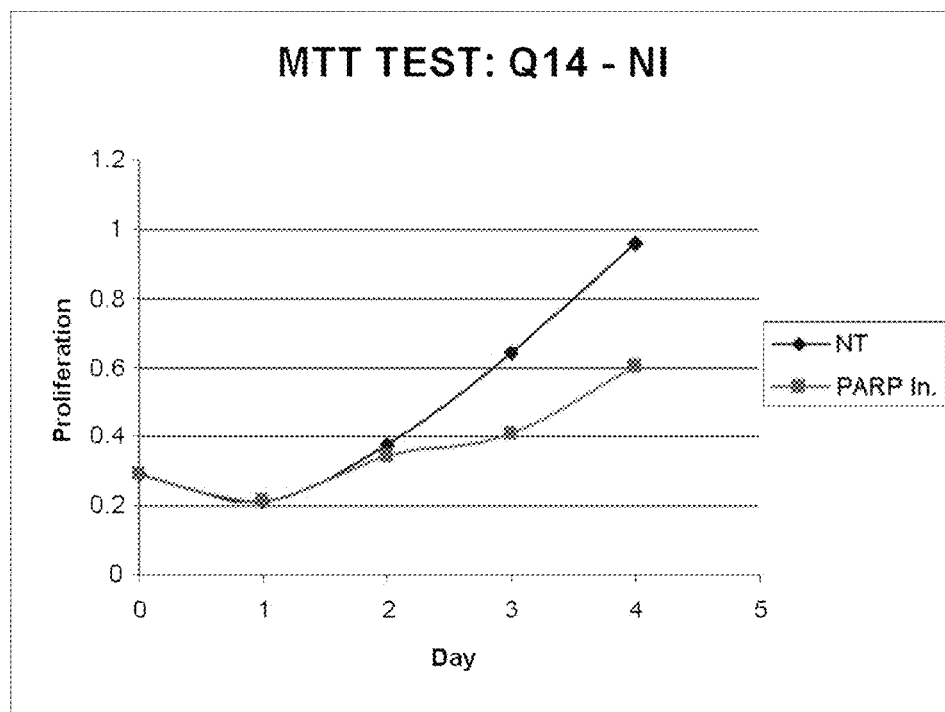
Figure 14:
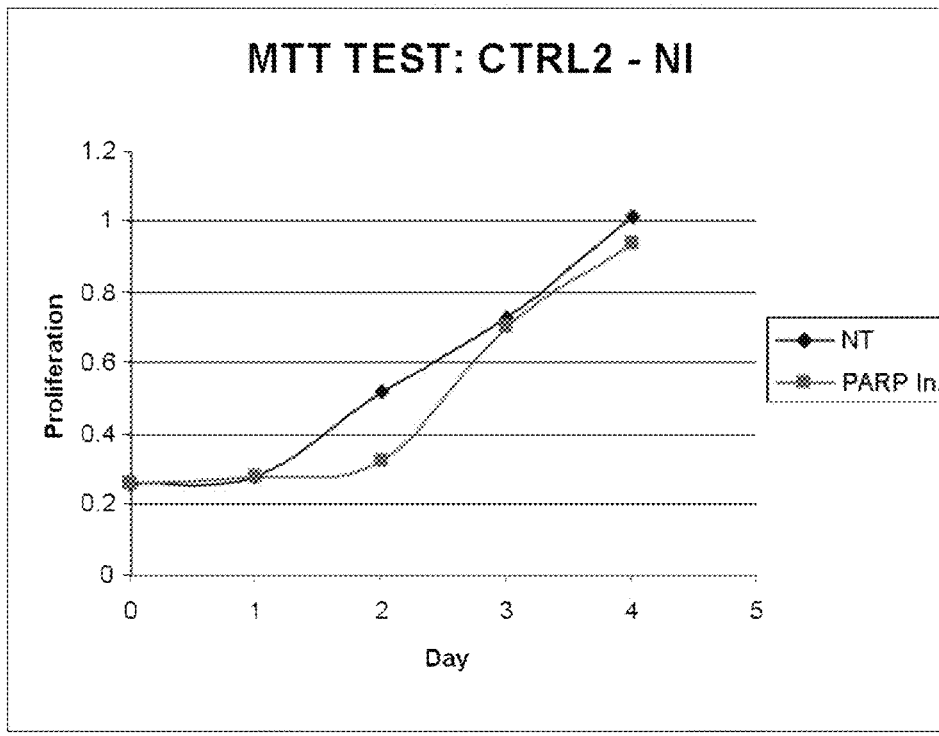
Figure 14:
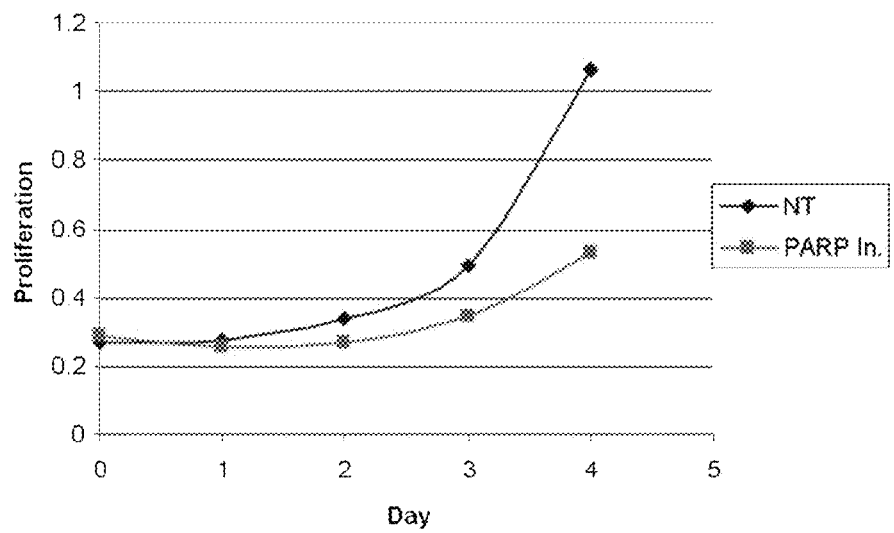
Figure 14:
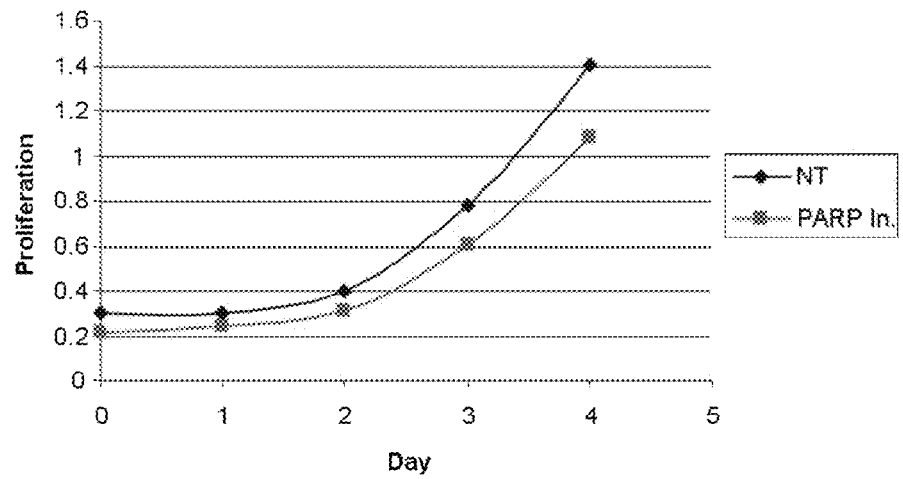

FIG. 14. Effect of POLQ gene overexpression on MRC5 cell sensitivity to DNA repair inhibitors Cultures of lung MRC5 fibroblasts transfected with a pcDNA POLQ-carrying vector (A) or with the corresponding naked vector (C) were treated with a sub-efficient dose of a PARP inhibitor, and cellular proliferation was monitored. Cultures of MRC5 cells transfected with a POLQ-carrying vector (B) or with the corresponding naked vector (D) were irradiated at sub-lethal doses (4 Gy), and cellular proliferation was monitored in the presence of PARP inhibitor.

Figure 15:
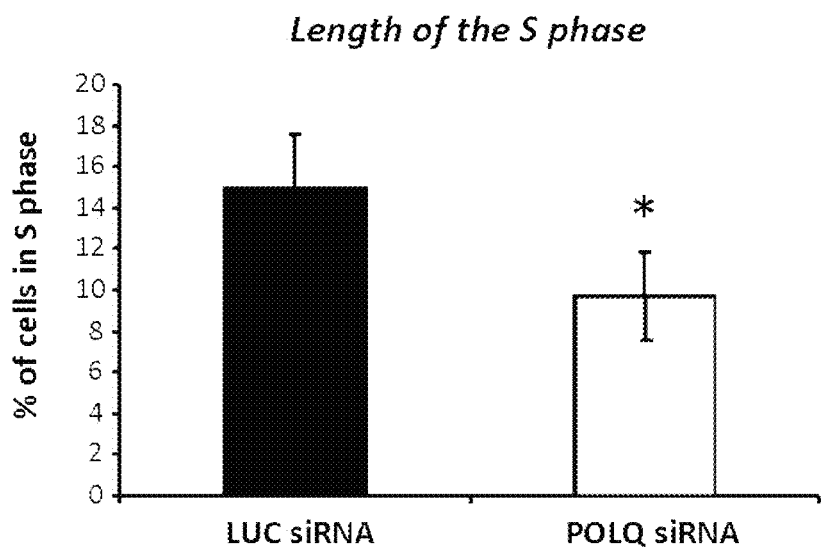
Figure 15:
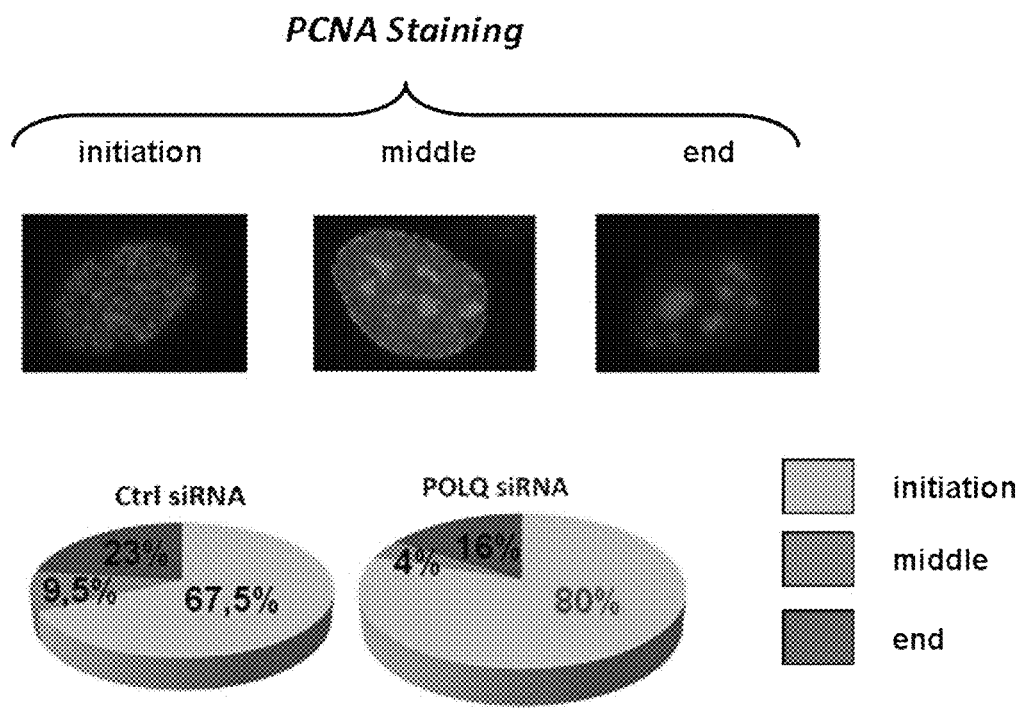
Figure 15:
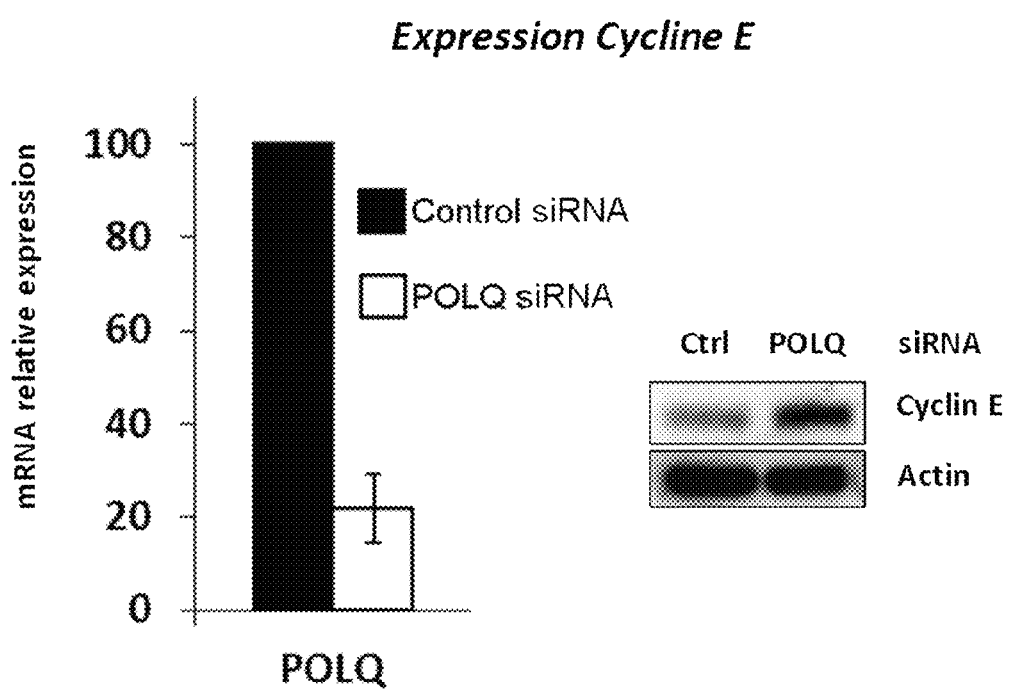

FIG. 15. Effect of POLQ depletion on DNA replication in MRC5 fibroblasts The effect of POLQ depletion on S phase was assessed in MRC5 cells transfected with POLQ siRNA, and compared to a LUC siRNA control (Ctrl): (A) Quantification of the average number of cells in S phase 8 hours after a thymidine chase; (B) Quantification of the average number of cells positive to PCNA staining; (C) Quantification of the cyclin E mRNA levels relative to the actin transcripts.

EXAMPLES

1. Material and Methods

1.1. Breast Cancer 1.1.1. Study Design, Patients and Tumor Samples, Differential Gene Expression Patients included consisted of a subset of patients from an adjuvant multicentric phase III clinical trial (PACS01 trial). The results of this clinical trial have been published elsewhere (Roché et al. *J Clin Oncol* 24: 5664-5671, 2006). Tumor samples from this cohort (n=206) were divided into two sets for genotyping (n=101 and n=105). Normal breast tissues were obtained at the Claudius Regaud Institute (Toulouse, France) and taken from the surgical specimen, at more than 3 cm from the breast cancer. Characteristics of patients and tumors from the cohort are described in Table 1.

TABLE 1

Baseline characteristics of patients and tumors

| | French cohort | | | |
|---|---|---|---|---|
| | Set 1 (n = 101) | | Set 2 (n = 105) | |
| Characteristics | n. of patients | % | n. of patients | % |
| Age (years) | | | | |
| Median | 49 | | 50.8 | |
| Range | 29-64 | | 31-64 | |
| Premenopausal | 70 | 69.31 | 58 | 55.24 |
| Surgery | | | | |
| Local excision | 60 | 59.41 | 54 | 51.43 |
| Mastectomy | 41 | 40.59 | 51 | 48.57 |
| Pathologic tumor size (mm) | | | | |
| Median | 23 | | 25 | |
| Range | 6-70 | | 10-150 | |
| Histological type | | | | |
| Ductal carcinoma | 82 | 81.19 | 80 | 76.19 |
| Lobular carcinoma | 12 | 11.88 | 11 | 10.48 |
| Other | 7 | 6.96 | 14 | 13.33 |
| Grade | | | | |
| I | 22 | 21.78 | 9 | 8.57 |
| II | 34 | 33.66 | 39 | 37.14 |
| III | 42 | 41.58 | 54 | 51.43 |
| Not graded | 2 | 1.98 | 2 | 1.9 |
| Missing | 1 | 0.99 | 1 | 0.95 |
| Number of positive nodes | | | | |
| ≤1 | 43 | 42.57 | 30 | 28.57 |
| >1 | 58 | 57.42 | 75 | 71.42 |
| Estrogen receptors | | | | |
| Positive | 68 | 67.33 | 74 | |
| Negative | 30 | 29.7 | 29 | |
| Missing | 3 | 2.97 | 2 | |
| Progesterone receptors | | | | |
| Positive | 42 | 41.58 | 41 | 39.05 |
| Negative | 56 | 55.45 | 62 | 59.05 |
| Missing | 3 | 2.97 | 2 | 1.9 |
| HER2 | | | | |
| Positive | 16 | 15.84 | 13 | 12.38 |
| Negative | 66 | 65.35 | 87 | 82.86 |
| Missing | 19 | 18.81 | 5 | 4.76 |
| Treatment | | | | |
| FEC (only) | 49 | 48.51 | 57 | 54.29 |
| FEC + TXT (only) | 52 | 51.49 | 48 | 45.71 |
| Other | 0 | 0 | 0 | 0 |
| Tamoxifen | 57 | 56.43 | 67 | 63.8 |

All the tumor tissue samples were surgically collected and immediately snap-frozen in liquid nitrogen and stored until RNA extraction. French tumor RNA was prepared on the same platform (IPSOGEN, Marseille, France) by the CsCl-cushion technique as described (Chirgwin J. et al: *Biochemistry* 18:5294-5299, 1979). During the extraction process, all tumor samples were controlled for sufficient tumoral cellularity (i.e. >50% tumor cells) by performing Hematoxylin and Eosin staining RNA extraction from 7 normal breast tissues was performed on thirty 10 µm-thick sections of the frozen tissue. This method allowed morphological control of the tissue processed for RNA extraction. Slides for each sample were stained with haematoxylin-eosin slides and analyzed by a pathologist. Each normal breast sample was reviewed in order to (i) ascertain the absence of any neoplastic lesion; (ii) quantify the percentage of normal epithelial, fibrous and adipous components. The quality and the quantity of all French RNA samples were assessed using the Agilent BioAnalyzer 2100 and only RNA presenting a suitable ratio 28S/18S (≥1.5) was selected for analysis.

For the French cohort, total RNA was reverse transcribed using the High-Capacity cDNA Archive Kit (Applied Biosystems). The level of transcripts was measured in triplicates by using the TaqMan low density array (Applied Biosystems). All studied genes were amplified in triplicate from tumor and normal samples using the TaqMan Universal PCR Master Mix and the TaqMan Low Density Array technology (Applied Biosystems). PCR amplifications were performed with lated variances related to set 1/n=101 and set 2/n=105 were the same (0.0033 for set 1 and 0.0031 for set 2, the T test p value being of 0.6510, data not shown).

TABLE 2

DNA context sequences and AB references

| SEQ ID NO. | Assay ID | Context Sequence | Gene Symbol | RefSeq | Localization |
|---|---|---|---|---|---|
| 1 | Hs00183533_m1 | AGGGGAATTGATCAGTGCATTCCAC | IPO8 | NM_006390.2 | exon 20-21 |
| 2 | Hs00609297_m1 | GCGGCTGCAACGGCGGAAGAAAACA | HMBS | NM_000190.3 | exon 1-2 |
| 3 | Hs00213524_m1 | TACAACCAACCAGGTGTGGTATTTC | POLA | NM_016937.1 | exon 30-32 |
| 4 | Hs00172491_m1 | CTGTTTGAAGCGGGATGGATGGCAA | POLD1 | NM_002691.1 | exon 1-2 |
| 5 | Hs00173030_m1 | CTTTGAAGAGGTGTGTGATGAGATT | POLE | NM_006231.2 | exon 16-17 |
| 6 | Hs00249411_m1 | GGGAAACATGGGGTGGGTATATGGC | REV1L | NM_016316.1 | exon 2-3 |
| 7 | Hs00197814_m1 | TCACACAATAAGGTCCTGGCAAAAC | POLH | NM_006502.1 | exon 5-6 |
| 8 | Hs00958495_m1 | GCAGAAAGCGGGCTCCAGCACCAC | POLM | NM_013284.1 | exon 6-7 |
| 9 | Hs00211963_m1 | TCCACGAAGGGGTCCAGATTTTATG | POLK | NM_016218.1 | exon 2-3 |
| 10 | Hs00161301_m1 | AAAAGCCCAGGGAGATTGGTGGACG | REV3L | NM_002912.1 | exon 13-14 |
| 11 | Hs00203191_m1 | GATTGAGCAGACAGTCCAGAAAGCA | POLL | NM_013274.2 | exon 7-8 |
| 12 | Hs00160263_m1 | GAGTTAGTGGCATTGGTCCATCTGC | POLB | NM_002690.1 | exon 5-6 |
| 13 | Hs00394916_m1 | TGGAGCAGGGAAGGAGCGGCTGGCT | POLN | NM_181808.1 | exon 18-19 |
| 14 | Hs00200488_m1 | CCAGCTCGCAGGGAGTTCATGATCA | POLI | NM_007195.1 | exon 1-2 |
| 15 | Hs00198196_m1 | GCCTTTCCCAGGTGGTTCAATACTG | POLQ | NM_006596.3 | exon 26-27 | the TaqMan Low Density Array technology and either the 7900HT fast real time PCR system (Toulouse, batch 1). For the French cohort, we normalized gene expression between samples by using two controls (HMBS, IPO8), which were amplified from each cDNA. These two control genes were selected by using the Genorm program as the most stable among 16 tested (B2M, TFRC, YWHAZ, RPLO, 18S, GUSB, UBC, TBP, GAPDH, PPIA, POLR2A, ACTB, PGK1, HPRT1, IPO8, HMBS) on the TaqMan Low Density Human Endogenous Control Array (Applied Biosystems). The primer DNA context sequences as well as the Applied Biosystems references used for analysis of each DNA polymerase and control genes are listed (Table 2). To analyze the variation of expression, T/N ratios between normalized values were calculated where T and N correspond respectively to tumor value and median of normal values. Otherwise, for analyses regarding POLQ expression and patient survival, IPO8 was chosen as a normalizer as it was the most stable gene out of the three chosen control genes. Indeed the calcu- 1.1.2. Statistical Analysis In the French cohort, the major parameters of analysis when comparing the expressions in cancer tissues were the individual T/N ratios normalized to expression of the controls HMBS and IPO8. Otherwise, in the analyses of POLQ expression in relation to survival, T/N ratios for POLQ were normalized to IPO8 only. Correlations between genes were assessed with a non parametric Spearman's correlation (Spearman's rho). Besides these analyses, the expression data were transformed into binomial data (more or less than 1): thus we could use binomial exact tests to evaluate the significance of gene over- and under-expression defined as unbalanced groups around 1. Relative quantities of POLQ mRNA levels were transformed into binomial data. In the French cohort all tumors with expression levels below or equal to 0.063 were defined as low expression. This cut off was defined in relation to survival in order to identify two statistically different populations of patients. Said cut off corresponds to a ratio of POLQ mRNA levels of 15.8. A low number of metastatic lymph nodes was defined as a lymph node counts equal to 1 or less, distinct from patients with 2 or more metastatic axillary nodes. The cancer specific survival was defined as the interval between the date of breast surgery and date of death or last-follow-up news (censored data). Patients dead from another cause are considered as a censored observation. Survival rates were estimated according to the Kaplan-Meier method and the log rank test was used to assess the differences between the groups. Cox's proportional hazards regression model using a backward selection procedure and likelihood ratio test was used to investigate the impact of prognostic factors on cancer specific survival. All variables associated with p<0.05 on univariate analysis were included in the initial model. All p-values were two sided. For all statistical tests, differences were considered significant at the 5% level.

1.1.3. Subcloning of POLQ

The human POLQ cDNA was transferred into the vector pcDNA 3.1 (Invitrogen) in two steps. First the pFast Bac HTC POLQ containing POLQ cDNA (Seki et al. *Nucleic Acids Res.* 31:6117-6126, 2003) was digested with RsrII and XhoI to give the N-terminal part of POLQ cDNA (1.2 kb). This product was subsequently inserted into pcDNA 3.1 (Invitrogen), previously digested with EcoRV and XhoI. The C-terminal part of POLQ cDNA (6.7 kb) was then isolated by digestion of the pFast Bac HTC POLQ with XhoI and SacII and inserted in the pcDNA 3.1 vector already containing the N-terminal part of POLQ cDNA after digestion of this vector with XhoI. The entire sequence of the POLQ cDNA was then confirmed.

1.1.4. Cell Engineering

MRC5-SV cells (ATCC) were grown and transfected as described (Pillaire et al. *Cell Cycle* 6: 471-7, 2007). POLQ overexpression was immuno-detected as published (Seki et al. *Nucleic Acids Res* 31: 6117-6126, 2003), using purified protein as a size control.

Cell cycle analysis studies were performed as also published (Bergoglio et al. *J Cell Science* 115: 4413-4418, 2002). Cell cycle analysis and cytotoxicity studies were performed as previously published (Bergoglio et al. *J Cell Science* 115: 4413-4418, 2002). Treatment was 1 h at 37° C. for methyl methanesulfonate (MMS) and continuous for N-methyl-N-nitrosourea (MNU) Immunodetection of γ-H2AX and PT68-CHK2 was carried out according to Rao et al. (Rao et al. *Mol Cancer Res* 5:713-24, 2007). For each clone, a minimum of 100 metaphases were analyzed in 3 independent experiments (Bergoglio et al. *Cancer Res* 62: 3511-3514, 2002).

1.1.5. DNA Combing and Statistical Analysis

Experiments were performed as previously described (Pillaire et al. *Cell Cycle* 6: 471-477, 2007). Basically, replicated DNA is first labeled with two consecutive pulses of halogenated nucleosides, iododeoxyuridine (IdU) and chlorodeoxyuridine (CldU) for 20 min each, and then isolated and stretched as recently described (Pillaire et al. *Cell Cycle* 6: 471-477, 2007). Newly replicated regions ("replication tracks") in the stretched DNA molecules can then be visualized and measured by immunostaining with antibodies that are specific to CldU or IdU. In the present case, cells were successively labeled for 20 minutes with 100 μM IdU and CldU (Sigma-Aldrich).

1.1.6. Sequencing of p53 and Analysis of Mutations

Exons 4 to 9 of p53 were amplified in a semi-nested PCR reaction carried out according to the manufacturer's recommendations: 2 ul of cDNA was added to a mix containing 45 μl, of PCR supermix (Invitrogen) and primers Gil (5'TGA TGC TGT CCC CGG ACG ATA TTG AAC3')(SEQ ID NO: 16) and Rev10 (5'CTT CCC AGC CTG GGC ATC CTT G3') (SEQ ID NO: 17). 1 ul of this PCR product was then added to a second PCR reaction with primers Gil and Rev9 (5'CTT CTT TGG CTG GGG AGA GGA3') (SEQ ID NO: 18). The amplification reaction consisted of one cycle of 94° C. for 3 min, followed by 35 cycles of 94° C. for 30 sec, 60° C. for 45 sec and 72° C. for 1 min30 sec and a final step of 72° C. for 8 min.

Amplified products were purified from 1% agarose gels with QIAquick Gel Extraction Kit (Qiagen) and submitted for sequencing at Ninewells hospital DNA analysis facility (Abi 3730 Genetic Analyser) using the primers Gil and MP9ER (5'CTC CCA GGA CAG GCA CAA ACA CG3') (SEQ ID NO: 19). Sequences obtained were aligned to p53 sequence NC 000017-9 from GenBank using the program Multalin (Multiple sequence alignment with hierarchical clustering) (Corpet F; *Nucleic Acids Res* 16(22): 10881-90, 1988). Mutations were confirmed by re-amplifying the sample and re-sequencing. Only exons 4 to 8 were analysed (from nucleotide 11407 to 14067 on sequence NC 000017-9) Mutations were further validated using the Mutation validation tools from the p53 IARC database (http://www-p53.iarc.fr/MutationValidationCriteria.asp) (Petitjean et al. *Hum Mutat.* 28(6):622-9, 2007) Sequences were then classified according to the type of mutation they contained: WT or Silent (0), Missense (1) and Nonsense (2).

1.2. Lung Cancer 1.2.1. Study Design, Patients and Tumor Samples, Differential Gene Expression Ninety-three patients carrying a pulmonary adenocarcinoma of stage I to IIIA were selected at the Centre Hospitalier Universitaire Rangueil-Larrey of Toulouse (France) between 2006 and 2010. Criteria assessed for inclusion of patients in the study were the availability of frozen tumoral and adjacent, non-tumoral tissues, and the possibility of obtaining RNA samples of a very high quality. Exclusion criteria were non-adenocarcinomous histology, a tumor of stage IIIB or IV, or a percentage of tumor cells of less than 70%.

The tumor stage was determined on the basis of clinical and anatomopathological data using the TNM system. Analysis of the tumor morphology by the anatomopathologists was performed according to the World Health Organization classification of 2004 (Travis, William D; Brambilla, Elisabeth; Muller-Hermelink, H Konrad et al., eds, Pathology and Genetics of Tumours of the Lung, Pleura, Thymus and Heart, World Health Organization Classification of Tumours, Lyon: IARC Press, 2004). Only the tumors containing above 70% of tumoral cells were retained for the present analysis.

All the tumor tissue samples were surgically collected and immediately snap-frozen in liquid nitrogen and stored until RNA extraction. Tumor RNA was prepared using the RNeasy Mini Kit (Qiagen) according to the manufacturer instructions. During the extraction process, all tumor samples were controlled for sufficient tumoral cellularity (i.e. >70% tumor cells) by performing haematoxylin-eosin staining on sixty 10 μm-thick or five 300 μm-thick sections of the frozen tissue. Likewise, slides for each normal sample were stained with haematoxylin-eosin slides and analyzed by a pathologist. Each normal sample was reviewed in order to (i) ascertain the absence of any neoplastic lesion; (ii) quantify the percentage of normal epithelial, fibrous and adipous components. The quality and the quantity of all French RNA samples were assessed using the Agilent BioAnalyzer 2100 and only RNA displaying a suitable ratio 28S/18S (≥1.7) and a suitable RNA integrity number (RIN≥7) was selected for analysis.

Total RNA was reverse transcribed using the High-Capacity cDNA Archive Kit (Applied Biosystems). The level of transcripts was measured in triplicates by using the TaqMan low density array (Applied Biosystems). All studied genes were amplified in triplicate from tumor and normal samples using the TaqMan Universal PCR Master Mix and the TaqMan Low Density Array technology (Applied Biosystems). PCR amplifications were performed with the TaqMan Low Density Array technology and either the 7900HT fast real time PCR system. Gene expression was normalized between samples by using four controls (GUSB, HMBS, IPO8, and UBC), which were amplified from each cDNA. These four control genes were selected by using the GeNorm program as the most stable among 16 tested (B2M, TFRC, YWHAZ, RPLO, 18S, GUSB, UBC, TBP, GAPDH, PPIA, POLR2A, ACTB, PGK1, HPRT1, IPO8, HMBS) on the TaqMan Low Density Human Endogenous Control Array (Applied Biosystems).

The primer DNA context sequences as well as the Applied Biosystems references used for analysis of each tested and control genes were selected on the Applied Biosystem web site (products.appliedbiosystems.com). The cDNA was amplified in presence of the different probes diluted 100-fold and of the TaqMan® Preamp Master Mix (Early Access) reagent (Applied Biosystems) for 14 cycles in the StepOne real-time PCR system (Applied Biosystems). Pre-amplification products were then diluted 5-fold. Pre-amplified cDNA were then resuspended in DNA Binding Sample Loading Reagent buffer (Applied Biosystems) in presence of Master Mix (Applied Biosystems). Meanwhile, each probe is diluted to 1/100 in Assay Loading Reagent buffer (Applied Biosystems). Amplification is performed on a Fluidigm Biomark™. The preamplified cDNAs and the probes are separately loaded onto 96.96 Dynamic Array (Fluidigm). Detection of real-time PCR reaction is performed on the Biomark Reader (Fluidigm).

Parameter of analysis were as suggested by the manufacturer (quality threshold=0.65; baseline correction=linear; Ct threshold method=auto global). Fluidigm PCR data were generated as monoplicates; they were then analyzed with the GenEx software (genex.gene-quantification.info/, MultiD), with the following protocol: &) normalization of the data with respect to the household genes identified by TLDA (GUSB, IPO8, UBC, HMBS): Ct in the tissue-mean of the Ct of the 4 household genes in the same tissue, 2) normalization of tumor tissue with respect to adjacent non-tumor tissue: number of RNA copies=2^Ct. Tumor tissue can be compared to the adjacent non-tumor tissue with the ratio: Nrel=2^CtNormal/2^CtTumor=2^(CtNormal−CtTumor). A gene is overexpressed if Nrel>1, a gene is under-expressed if Nrel<1, 3/binomial transformation: in order to obtain a normal distribution allowing the performance of statistical tests: Log 2(Nrel)=Log 2(2^CtNormal/2^CtTumor)=Ct Normal−Ct Tumor. A gene is overexpressed if CtHealthy−CtTumor>0, a gene is underexpressed if CtHealthy−CtTumoral<0.

1.2.2. Statistical Analysis

As a first step, for each of the studied genes, the probability of observing more than 50% of the patients overexpressing or underexpressing the said gene (threshold: Nrel>2 for overexpression and Nres<1/2 for underexpression) was assessed by a binomial test. The significance level was 0.05 and the procedure of Benjamini and Yekutieli was used to assess for the multiplicity of tests. Correlations between genes were assessed with a non parametric Spearman's correlation (Spearman's rho). Expression levels (classified in 3 categories according to the terciles of the Nrel distribution) were compared in relation to the treatment (surgery only, surgery-chemotherapy-radiotherapy, or surgery-chemotherapy), to the tumor grade (N or TNM), of the tumor differentiation (poorly-, moderately-, or well-differentiated), of the presence of emboli, and of the smoking habits by chi-square or Fisher's exact test. Survival of the patients in relation to the expression levels (in 3 categories) was evaluated by the Kaplan Meier method and compared by log-Rank test. Survival in relation to the expression levels of the genes was analysed in multivariate with a Cox model.

1.2.3. Subcloning of POLQ

The human POLQ cDNA was transferred into the vector pcDNA 3.1 (Invitrogen) in two steps. First the pFast Bac HTC POLQ containing POLQ cDNA (Seki et al. *Nucleic Acids Res.* 31:6117-6126, 2003) was digested with RsrII and XhoI to give the N-terminal part of POLQ cDNA (1.2 kb). This product was subsequently inserted into pcDNA 3.1 (Invitrogen), previously digested with EcoRV and XhoI. The C-terminal part of POLQ cDNA (6.7 kb) was then isolated by digestion of the pFast Bac HTC POLQ with XhoI and SacII and inserted in the pcDNA 3.1 vector already containing the N-terminal part of POLQ cDNA after digestion of this vector with XhoI. The entire sequence of the POLQ cDNA was then confirmed.

1.2.4. Cell Engineering

MRC5-SV cells (ATCC) were grown and transfected as described (Pillaire et al. *Cell Cycle* 6: 471-7, 2007). Cell cycle analysis studies were performed as also published (Bergoglio et al. *J Cell Science* 115: 4413-4418, 2002). Cell cycle analysis and cytotoxicity studies were performed as previously published (Bergoglio et al. *J Cell Science* 115: 4413-4418, 2002). Cells were collected 3 hours after colcemid treatment and metaphase spreads were prepared. For each clone, a minimum of 100 metaphases were analyzed in 3 independent experiments; p-values were calculated by Student's t-test (Bergoglio et al. *Cancer Res* 62: 3511-3514, 2002).

2. Results 2.1. Breast Cancer 2.1.1. POLQ is the DNA Polymerase Gene Most Up-Regulated in Breast Tumors.

Real-time PCR was performed to generate gene expression profiles from a series of breast carcinomas (n=101, Table 1). Relative expression levels of DNA polymerases for each tumor, normalized to the median expression level of 7 non-tumor breast tissues, are shown in FIG. 1. The data clearly indicates that the POLQ gene is more highly expressed in tumor tissues of almost all patients compared to normal tissues, probably because the expression in non-tumor tissues is exceptionally low (Table 3). Among all the polymerase genes analyzed, for the replicative (POLA, POLD and POLE) or specialized (POLH, POLL, POLM, POLN, POLK, POLB, POLI, POLZ/REV3L and REV1) enzymes, POLQ showed the highest level of relative T/N expression. The expression of POLQ was up-regulated by 3 to 26-fold in tumor samples compared to normal tissues. In 70 out of 101 tumors (69.3%) POLQ expression was up-regulated by 5-fold or greater.

TABLE 3

Ct values in tumor and normal tissues for each DNA polymerase gene, as derived from Q-PCR analysis

| SET1 | POLA1 | POLD1 | POLE | REV1 | POLH | POLM | POLK | REV3L |
|---|---|---|---|---|---|---|---|---|
| Tumors | | | | | | | | |
| PACS01-BEG-BR001 | 26.89 | 26.95 | 26.50 | 26.96 | 26.83 | 27.76 | 25.42 | 26.55 |

TABLE 3-continued

Ct values in tumor and normal tissues for each DNA polymerase gene, as derived from Q-PCR analysis

| | | | | | | | | |
|---|---|---|---|---|---|---|---|---|
| PACS01-AVA-BR-003 | 26.94 | 27.93 | 26.56 | 26.79 | 27.47 | 27.32 | 25.93 | 26.94 |
| PACS01-AVA-BR004 | 27.09 | 27.93 | 26.95 | 26.43 | 26.90 | 27.93 | 25.67 | 26.77 |
| PACS01-AVA-BR-005 | 27.87 | 27.96 | 26.93 | 27.30 | 27.82 | 27.73 | 25.99 | 27.41 |
| PACS01-AVA-BR006 | 27.29 | 27.91 | 27.46 | 26.96 | 27.82 | 28.06 | 26.10 | 26.93 |
| PACS01-AVA-BR009 | 27.22 | 27.07 | 26.90 | 27.82 | 27.89 | 27.91 | 26.81 | 26.63 |
| PACS01-BEG-BR002 | 27.64 | 27.63 | 26.93 | 26.90 | 26.88 | 27.94 | 25.74 | 26.83 |
| PACS01-CJP-BR108 | 27.30 | 26.59 | 26.72 | 27.58 | 27.88 | 28.03 | 26.06 | 26.94 |
| PACS01-CJP-BR109 | 26.92 | 26.92 | 26.93 | 26.98 | 27.58 | 28.25 | 25.82 | 27.32 |
| PACS01-CJP-BR110 | 26.62 | 26.95 | 26.41 | 26.89 | 26.96 | 27.97 | 25.83 | 27.88 |
| PACS01-CJP-BR111 | 26.98 | 26.55 | 26.92 | 27.22 | 26.05 | 28.71 | 26.96 | 26.69 |
| PACS01-CJP-BR112 | 27.92 | 27.85 | 27.47 | 27.07 | 27.59 | 27.97 | 25.86 | 26.81 |
| PACS01-CJP-BR114 | 27.63 | 27.68 | 26.90 | 26.80 | 26.91 | 26.83 | 25.20 | 26.66 |
| PACS01-CJP-BR115 | 26.89 | 26.97 | 26.42 | 26.88 | 26.89 | 26.94 | 25.68 | 27.01 |
| PACS01-CJP-BR116 | 27.50 | 27.75 | 26.89 | 26.73 | 27.61 | 28.31 | 25.89 | 26.58 |
| PACS01-CJP-BR117 | 26.91 | 27.12 | 26.20 | 26.91 | 27.90 | 26.89 | 25.18 | 26.18 |
| PACS01-FBA-BR092 | 27.65 | 27.12 | 26.88 | 26.89 | 25.92 | 27.97 | 26.60 | 26.75 |
| PACS01-FBA-BR094 | 26.95 | 26.96 | 26.67 | 26.79 | 26.89 | 26.92 | 25.44 | 25.85 |
| PACS01-FBA-BR097 | 27.23 | 27.72 | 26.92 | 26.91 | 26.86 | 27.33 | 25.86 | 26.78 |
| PACS01-FBA-BR101 | 26.83 | 26.93 | 26.59 | 26.89 | 26.85 | 27.86 | 26.62 | 26.92 |
| PACS01-FBA-BR103 | 27.40 | 27.84 | 26.93 | 27.27 | 27.83 | 27.67 | 26.93 | 27.14 |
| PACS01-FBA-BR105 | 26.67 | 25.60 | 26.29 | 26.70 | 26.91 | 27.06 | 24.79 | 26.23 |
| PACS01-FBA-BR106 | 27.90 | 27.95 | 27.91 | 26.84 | 26.93 | 27.43 | 25.80 | 26.82 |
| PACS01-HCL-BR119 | 27.93 | 27.87 | 26.91 | 26.81 | 27.76 | 27.48 | 25.87 | 26.87 |
| PACS01-HCL-BR122 | 26.94 | 25.16 | 25.78 | 27.88 | 27.94 | 28.70 | 26.51 | 26.65 |
| PACS01-HCL-BR123 | 26.68 | 27.02 | 25.30 | 26.27 | 26.89 | 27.32 | 25.90 | 25.79 |

TABLE 3-continued

Ct values in tumor and normal tissues for each DNA polymerase gene, as derived from Q-PCR analysis

| | | | | | | | | |
|---|---|---|---|---|---|---|---|---|
| PACS01-HCL-BR126 | 26.94 | 26.88 | 25.90 | 26.91 | 27.83 | 27.93 | 25.89 | 26.87 |
| PACS01-HCL-BR127 | 27.63 | 27.75 | 26.89 | 26.64 | 27.36 | 27.86 | 26.15 | 26.88 |
| PACS01-HTE-BR154 | 27.01 | 26.92 | 25.90 | 26.74 | 27.56 | 26.89 | 25.80 | 26.58 |
| PACS01-IGR-BR132 | 27.21 | 26.97 | 26.85 | 26.78 | 26.92 | 27.81 | 25.65 | 26.86 |
| PACS01-IGR-BR133 | 26.92 | 27.18 | 26.57 | 26.81 | 27.18 | 27.98 | 25.87 | 27.83 |
| PACS01-IGR-BR135 | 25.75 | 26.36 | 25.49 | 26.71 | 26.88 | 26.95 | 24.85 | 25.59 |
| PACS01-IGR-BR138 | 25.94 | 25.96 | 24.91 | 26.86 | 26.47 | 26.87 | 25.47 | 26.88 |
| PACS01-IGR-BR139 | 27.83 | 27.83 | 26.92 | 26.90 | 27.88 | 27.64 | 25.91 | 27.78 |
| PACS01-IGR-BR141 | 27.92 | 27.40 | 26.90 | 26.55 | 27.80 | 27.94 | 26.56 | 26.55 |
| PACS01-IGR-BR142 | 27.84 | 27.96 | 26.94 | 27.68 | 27.47 | 28.02 | 26.93 | 26.94 |
| PACS01-IGR-BR143 | 26.81 | 27.44 | 26.31 | 26.77 | 26.88 | 27.46 | 25.88 | 25.87 |
| PACS01-IGR-BR144 | 27.19 | 27.25 | 26.96 | 26.93 | 27.90 | 27.85 | 26.34 | 26.58 |
| PACS01-IGR-BR145 | 26.97 | 26.99 | 26.86 | 26.84 | 26.84 | 27.76 | 25.82 | 26.88 |
| PACS01-IGR-BR146 | 26.97 | 26.88 | 26.59 | 26.85 | 26.89 | 27.86 | 26.07 | 26.91 |
| PACS01-IGR-BR147 | 28.26 | 27.59 | 27.95 | 27.89 | 28.65 | 29.84 | 27.42 | 28.18 |
| PACS01-IGR-BR148 | 27.66 | 28.60 | 26.96 | 27.89 | 27.86 | 28.06 | 26.69 | 27.59 |
| PACS01-IGR-BR149 | 27.87 | 27.90 | 27.03 | 27.94 | 27.72 | 28.40 | 26.95 | 27.79 |
| PACS01-IGR-BR150 | 27.91 | 27.90 | 26.63 | 26.93 | 27.87 | 27.81 | 25.92 | 26.90 |
| PACS01-IGR-BR151 | 27.88 | 27.74 | 26.92 | 26.85 | 27.85 | 27.91 | 26.16 | 27.42 |
| PACS01-IGR-BR152 | 25.41 | 26.86 | 25.95 | 25.94 | 25.92 | 26.70 | 24.64 | 25.87 |
| PACS01-IGR-BR153 | 26.90 | 27.43 | 26.20 | 27.41 | 27.23 | 27.90 | 26.84 | 27.84 |
| PACS01-JGO-BR011 | 27.95 | 27.88 | 27.84 | 27.92 | 27.83 | 27.94 | 26.81 | 27.86 |
| PACS01-JGO-BR015 | 26.95 | 26.62 | 26.39 | 27.26 | 28.37 | 28.85 | 26.91 | 26.81 |
| PACS01T-FBE-BR259 | 26.84 | 27.43 | 26.18 | 26.83 | 27.61 | 27.93 | 25.88 | 27.78 |
| PACS01T-HCL-BR307 | 27.80 | 27.61 | 26.74 | 26.87 | 26.88 | 27.84 | 26.67 | 26.95 |

TABLE 3-continued

Ct values in tumor and normal tissues for each DNA polymerase gene, as derived from Q-PCR analysis

| | | | | | | | | |
|---|---|---|---|---|---|---|---|---|
| PACS01T-HCL-BR306 | 27.44 | 28.08 | 26.81 | 27.36 | 27.01 | 28.06 | 26.91 | 27.69 |
| PACS01T-HCL-BR309 | 28.74 | 27.92 | 26.80 | 27.51 | 27.09 | 27.86 | 27.95 | 27.87 |
| PACS01T-HCL-BR310 | 27.84 | 27.93 | 26.94 | 26.79 | 27.25 | 27.06 | 25.81 | 26.41 |
| PACS01T-HCL-BR313 | 27.97 | 28.35 | 27.52 | 27.86 | 27.85 | 28.08 | 26.80 | 27.85 |
| PACS01T-HCL-BR314 | 26.91 | 27.79 | 26.79 | 26.94 | 26.83 | 27.31 | 25.20 | 26.10 |
| PACS01T-HCL-BR317 | 27.55 | 28.76 | 26.60 | 27.32 | 27.40 | 27.89 | 25.80 | 26.88 |
| PACS01T-HCL-BR318 | 26.92 | 26.89 | 26.85 | 26.92 | 26.91 | 27.92 | 25.91 | 26.65 |
| PACS01T-HCL-BR319 | 27.56 | 27.61 | 27.44 | 27.09 | 26.66 | 27.86 | 25.55 | 26.88 |
| PACS01T-HTE-BR256 | 26.12 | 26.86 | 25.35 | 26.85 | 26.72 | 27.43 | 25.85 | 27.82 |
| PACS01T-IGR-BR260 | 27.35 | 28.10 | 27.00 | 27.17 | 27.93 | 27.48 | 26.78 | 27.80 |
| PACS01T-IGR-BR261 | 26.73 | 27.35 | 25.84 | 27.86 | 27.29 | 27.87 | 26.80 | 26.58 |
| PACS01T-IGR-BR262 | 26.93 | 26.86 | 26.57 | 27.89 | 26.92 | 28.19 | 27.82 | 27.87 |
| PACS01T-IGR-BR265 | 27.60 | 27.97 | 26.88 | 27.21 | 27.32 | 27.87 | 26.31 | 26.85 |
| PACS01T-IGR-BR266 | 26.92 | 27.39 | 26.63 | 26.92 | 27.91 | 27.56 | 26.81 | 27.26 |
| PACS01T-IGR-BR267 | 27.64 | 27.84 | 27.65 | 27.90 | 27.76 | 27.93 | 26.07 | 26.71 |
| PACS01T-IGR-BR268 | 26.95 | 27.00 | 26.94 | 27.97 | 27.86 | 27.88 | 26.24 | 27.53 |
| PACS01T-IGR-BR270 | 26.90 | 27.65 | 26.86 | 27.64 | 26.69 | 27.92 | 26.55 | 26.74 |
| PACS01T-IGR_BR272 | 27.54 | 27.89 | 26.82 | 27.85 | 26.94 | 27.74 | 26.96 | 26.88 |
| PACS01T-IGR-BR273 | 26.72 | 27.31 | 26.04 | 27.87 | 26.91 | 27.41 | 26.22 | 27.39 |
| PACS01T-IGR-BR274 | 27.96 | 27.82 | 26.81 | 27.49 | 27.25 | 27.98 | 26.68 | 26.82 |
| PACS01T-IGR-BR275 | 26.95 | 26.90 | 25.90 | 27.84 | 26.91 | 28.08 | 26.71 | 27.91 |
| PACS01T-IGR-BR277 | 27.11 | 27.43 | 26.65 | 27.60 | 27.17 | 26.60 | 26.84 | 27.79 |
| PACS01T-IGR-BR278 | 27.87 | 27.82 | 27.76 | 27.92 | 27.66 | 28.63 | 27.07 | 28.68 |
| PACS01T-IGR-BR280 | 27.27 | 28.94 | 27.05 | 27.17 | 26.92 | 27.87 | 25.79 | 26.85 |
| PACS01T-IGR-BR282 | 27.81 | 27.66 | 26.99 | 26.90 | 27.86 | 27.86 | 26.37 | 26.62 |
| PACS01T-IGR-BR283 | 28.94 | 27.98 | 27.59 | 28.26 | 27.94 | 28.72 | 27.85 | 28.85 |

TABLE 3-continued

Ct values in tumor and normal tissues for each DNA polymerase gene, as derived from Q-PCR analysis

| | | | | | | | | |
|---|---|---|---|---|---|---|---|---|
| PACS01T-IGR-BR284 | 27.93 | 27.92 | 27.03 | 27.80 | 27.86 | 27.86 | 25.74 | 28.46 |
| PACS01T-IGR-BR286 | 27.54 | 28.82 | 27.89 | 26.69 | 27.19 | 28.76 | 26.81 | 27.77 |
| PACS01T-IGR-BR288 | 26.81 | 27.05 | 26.56 | 27.95 | 26.96 | 26.91 | 25.90 | 27.90 |
| PACS01T-IGR-BR289 | 26.91 | 27.41 | 26.93 | 27.48 | 26.80 | 27.06 | 25.80 | 26.66 |
| PACS01T-IGR-BR290 | 27.49 | 27.83 | 26.86 | 27.87 | 27.83 | 27.74 | 27.46 | 26.94 |
| PACS01T-IGR-BR291 | 26.96 | 26.71 | 26.86 | 28.02 | 26.89 | 28.40 | 26.88 | 26.89 |
| PACS01T-BEG-BR294 | 27.46 | 27.50 | 26.34 | 27.95 | 27.62 | 27.81 | 26.43 | 27.87 |
| PACS01T-IPC-BR-298 | 27.96 | 28.16 | 26.93 | 27.82 | 27.93 | 27.58 | 26.83 | 27.86 |
| PACS01T-IPC-BR299 | 26.80 | 26.50 | 26.22 | 27.90 | 27.91 | 27.88 | 26.68 | 26.81 |
| PACS01T-IPC-BR300 | 27.28 | 27.83 | 26.91 | 27.74 | 27.47 | 27.94 | 26.87 | 26.86 |
| PACS01T-IPC-BR301 | 27.67 | 27.44 | 27.21 | 27.81 | 27.74 | 27.87 | 26.20 | 26.73 |
| PACS01T-IPC-BR303 | 26.50 | 25.99 | 25.28 | 26.95 | 26.59 | 27.75 | 25.68 | 26.25 |
| PACS01T-IPC-BR304 | 27.89 | 28.29 | 26.88 | 27.42 | 26.93 | 28.13 | 26.41 | 26.87 |
| PACS01T-IPC-BR305 | 26.88 | 27.12 | 25.85 | 26.89 | 26.91 | 27.85 | 25.59 | 26.43 |
| PACS01T-PPA-BR237 | 26.09 | 26.57 | 25.82 | 26.95 | 26.88 | 27.89 | 25.85 | 26.85 |
| PACS01T-PPA-BR241 | 27.11 | 27.27 | 25.85 | 26.87 | 27.78 | 27.94 | 25.89 | 26.42 |
| PACS01T-PPA-BR243 | 26.02 | 26.95 | 25.36 | 26.26 | 26.92 | 26.53 | 25.42 | 25.98 |
| PACS01T-PPA-BR244 | 27.91 | 26.06 | 26.88 | 26.89 | 26.89 | 29.18 | 26.44 | 27.03 |
| PACS01T-PPA-BR246 | 27.81 | 27.09 | 26.44 | 27.14 | 27.90 | 27.93 | 25.92 | 27.22 |
| PACS01T-PPA-BR249 | 26.92 | 26.30 | 25.41 | 26.89 | 26.79 | 26.99 | 25.65 | 26.77 |
| PACS01T-PPA-BR250 | 27.71 | 28.06 | 26.92 | 27.27 | 27.95 | 27.99 | 26.80 | 26.92 |
| PACS01T-PPA-BR251 | 26.23 | 26.90 | 25.86 | 27.51 | 26.83 | 27.89 | 25.97 | 26.95 |
| PACS01T-PPA-BR253 | 26.90 | 27.59 | 26.85 | 26.74 | 26.96 | 27.71 | 25.62 | 26.79 |
| PACS01T-PPA-BR254 | 25.97 | 26.89 | 25.84 | 26.78 | 25.89 | 27.92 | 25.92 | 26.85 |
| Normal tissues | | | | | | | | |
| C51 | 26.87 | 26.56 | 25.23 | 27.36 | 26.61 | 27.07 | 25.70 | 26.98 |
| PORL1 | 29.11 | 29.88 | 29.73 | 28.88 | 29.48 | 30.40 | 26.91 | 28.56 |

TABLE 3-continued

Ct values in tumor and normal tissues for each DNA polymerase gene, as derived from Q-PCR analysis

| | | | | | | | |
|---|---|---|---|---|---|---|---|
| GARL2 | 29.64 | 30.86 | 29.76 | 28.85 | 29.67 | 30.38 | 27.72 | 28.75 |
| MISL3 | 28.94 | 29.75 | 28.89 | 27.93 | 28.88 | 30.00 | 26.83 | 27.69 |
| TROL4 | 28.82 | 29.76 | 28.59 | 28.03 | 28.91 | 29.63 | 26.82 | 27.90 |
| GERL5 | 28.85 | 29.94 | 28.94 | 27.96 | 28.73 | 29.74 | 27.21 | 27.69 |

| SET1 | POLL | POLB | POLN | POLI | POLQ | IPO8 | HMBS |
|---|---|---|---|---|---|---|---|
| Tumors | | | | | | | |
| PACS01-BEG-BR001 | 27.88 | 27.33 | 30.85 | 28.36 | 28.89 | 25.44 | 27.30 |
| PACS01-AVA-BR-003 | 27.60 | 26.42 | 29.79 | 27.85 | 30.82 | 25.94 | 27.53 |
| PACS01-AVA-BR004 | 27.85 | 27.89 | 29.81 | 28.01 | 31.75 | 25.66 | 27.94 |
| PACS01-AVA-BR-005 | 27.87 | 25.93 | 31.59 | 28.74 | 29.21 | 25.90 | 26.95 |
| PACS01-AVA-BR006 | 27.91 | 27.93 | 30.99 | 28.79 | 30.82 | 26.33 | 28.61 |
| PACS01-AVA-BR009 | 28.49 | 27.93 | 30.84 | 28.99 | 29.85 | 26.71 | 28.34 |
| PACS01-BEG-BR002 | 27.75 | 27.78 | 28.87 | 27.97 | 32.64 | 25.92 | 27.88 |
| PACS01-CJP-BR108 | 28.09 | 27.00 | 30.66 | 27.92 | 29.62 | 25.81 | 28.50 |
| PACS01-CJP-BR109 | 28.37 | 27.83 | 31.87 | 28.87 | 29.01 | 26.11 | 28.94 |
| PACS01-CJP-BR110 | 27.15 | 27.33 | 29.71 | 27.12 | 30.68 | 25.88 | 28.69 |
| PACS01-CJP-BR111 | 28.78 | 27.89 | 30.95 | 28.91 | 30.96 | 26.15 | 26.88 |
| PACS01-CJP-BR112 | 27.95 | 27.34 | 29.87 | 27.91 | 32.17 | 26.30 | 28.40 |
| PACS01-CJP-BR114 | 27.54 | 27.11 | 29.79 | 27.90 | 31.63 | 26.05 | 27.94 |
| PACS01-CJP-BR115 | 27.94 | 26.93 | 28.97 | 28.02 | 30.45 | 25.78 | 28.01 |
| PACS01-CJP-BR116 | 27.52 | 27.57 | 30.63 | 28.02 | 31.77 | 25.92 | 27.90 |
| PACS01-CJP-BR117 | 27.52 | 27.88 | 30.96 | 26.92 | 31.95 | 25.93 | 29.15 |
| PACS01-FBA-BR092 | 28.49 | 27.79 | 29.15 | 27.00 | 30.94 | 26.82 | 28.88 |
| PACS01-FBA-BR094 | 27.95 | 29.30 | 29.12 | 27.72 | 30.76 | 25.58 | 27.91 |
| PACS01-FBA-BR097 | 27.82 | 28.79 | 29.96 | 27.94 | 30.83 | 25.86 | 27.83 |
| PACS01-FBA-BR101 | 27.83 | 27.49 | 29.32 | 28.25 | 29.47 | 25.83 | 26.88 |
| PACS01-FBA-BR103 | 27.84 | 28.77 | 30.20 | 27.90 | 30.86 | 26.28 | 27.86 |
| PACS01-FBA-BR105 | 27.35 | 27.80 | 29.03 | 27.84 | 29.44 | 25.16 | 27.85 |

TABLE 3-continued

Ct values in tumor and normal tissues for each DNA polymerase gene, as derived from Q-PCR analysis

| | | | | | | | |
|---|---|---|---|---|---|---|---|
| PACS01-FBA-BR106 | 27.97 | 29.80 | 26.59 | 27.80 | 31.05 | 25.87 | 27.90 |
| PACS01-HCL-BR119 | 27.94 | 26.93 | 28.78 | 27.73 | 33.69 | 26.43 | 28.84 |
| PACS01-HCL-BR122 | 27.97 | 26.81 | 30.03 | 29.59 | 28.84 | 25.83 | 27.42 |
| PACS01-HCL-BR123 | 27.56 | 25.89 | 28.88 | 27.91 | 29.51 | 25.37 | 28.04 |
| PACS01-HCL-BR126 | 27.39 | 27.03 | 31.26 | 28.76 | 28.79 | 25.95 | 27.78 |
| PACS01-HCL-BR127 | 27.95 | 28.84 | 29.86 | 28.94 | 31.50 | 26.83 | 28.87 |
| PACS01-HTE-BR154 | 27.87 | 26.92 | 29.39 | 27.89 | 31.30 | 25.73 | 28.32 |
| PACS01-IGR-BR132 | 27.52 | 27.56 | 29.01 | 27.93 | 30.69 | 25.90 | 28.50 |
| PACS01-IGR-BR133 | 27.91 | 28.80 | 29.89 | 28.94 | 29.80 | 25.94 | 27.89 |
| PACS01-IGR-BR135 | 26.91 | 25.94 | 26.86 | 25.98 | 29.18 | 24.96 | 27.00 |
| PACS01-IGR-BR138 | 27.57 | 27.55 | 28.41 | 26.95 | 27.96 | 25.65 | 26.93 |
| PACS01-IGR-BR139 | 27.73 | 26.89 | 29.13 | 27.63 | 31.06 | 25.87 | 26.91 |
| PACS01-IGR-BR141 | 28.86 | 28.26 | 30.93 | 29.80 | 29.85 | 25.94 | 28.57 |
| PACS01-IGR-BR142 | 27.92 | 27.98 | 29.47 | 28.37 | 33.91 | 26.81 | 28.84 |
| PACS01-IGR-BR143 | 27.42 | 27.06 | 28.89 | 27.89 | 30.71 | 25.93 | 27.68 |
| PACS01-IGR-BR144 | 27.92 | 27.61 | 30.84 | 28.93 | 31.94 | 26.23 | 28.88 |
| PACS01-IGR-BR145 | 27.42 | 27.89 | 28.73 | 28.01 | 29.92 | 25.90 | 27.68 |
| PACS01-IGR-BR146 | 27.90 | 26.90 | 30.83 | 28.80 | 29.60 | 26.27 | 27.93 |
| PACS01-IGR-BR147 | 29.66 | 27.69 | 32.85 | 30.56 | 28.89 | 27.01 | 27.65 |
| PACS01-IGR-BR148 | 28.10 | 28.94 | 30.88 | 28.63 | 33.06 | 26.94 | 29.39 |
| PACS01-IGR-BR149 | 28.39 | 27.93 | 30.96 | 30.11 | 30.12 | 26.62 | 27.94 |
| PACS01-IGR-BR150 | 27.89 | 27.95 | 29.80 | 28.50 | 31.21 | 26.08 | 27.77 |
| PACS01-IGR-BR151 | 27.80 | 27.22 | 30.73 | 27.82 | 31.85 | 25.91 | 27.93 |
| PACS01-IGR-BR152 | 26.83 | 25.83 | 26.87 | 27.31 | 29.86 | 24.69 | 27.45 |
| PACS01-IGR-BR153 | 28.56 | 27.66 | 29.84 | 28.89 | 29.96 | 25.94 | 27.96 |

TABLE 3-continued

Ct values in tumor and normal tissues for each DNA polymerase gene, as derived from Q-PCR analysis

| | | | | | | | |
|---|---|---|---|---|---|---|---|
| PACS01-JGO-BR011 | 28.01 | 27.83 | 30.78 | 28.61 | 31.13 | 26.89 | 28.89 |
| PACS01-JGO-BR015 | 28.94 | 27.89 | 28.97 | 28.78 | 30.10 | 26.92 | 27.56 |
| PACS01T-FBE-BR259 | 27.94 | 27.94 | 29.75 | 28.83 | 29.99 | 25.87 | 28.09 |
| PACS01T-HCL-BR307 | 28.18 | 28.26 | 29.46 | 27.84 | 31.12 | 25.81 | 28.31 |
| PACS01T-HCL-BR306 | 28.53 | 27.98 | 29.93 | 28.91 | 30.86 | 26.78 | 28.80 |
| PACS01T-HCL-BR309 | 28.70 | 28.74 | 30.00 | 28.55 | 32.52 | 26.74 | 28.91 |
| PACS01T-HCL-BR310 | 27.86 | 27.90 | 29.94 | 27.76 | 30.75 | 25.77 | 28.60 |
| PACS01T-HCL-BR313 | 28.87 | 28.01 | 30.18 | 28.88 | 31.95 | 26.93 | 29.00 |
| PACS01T-HCL-BR314 | 27.78 | 26.96 | 28.93 | 27.75 | 31.77 | 25.96 | 27.67 |
| PACS01T-HCL-BR317 | 27.97 | 28.70 | 29.80 | 27.94 | 32.96 | 26.56 | 28.88 |
| PACS01T-HCL-BR318 | 28.51 | 29.70 | 29.34 | 27.93 | 29.96 | 25.91 | 28.86 |
| PACS01T-HCL-BR319 | 28.88 | 28.77 | 29.25 | 27.68 | 30.73 | 25.92 | 27.95 |
| PACS01T-HTE-BR256 | 27.83 | 26.61 | 28.08 | 27.69 | 28.93 | 25.41 | 27.85 |
| PACS01T-IGR-BR260 | 28.41 | 28.51 | 30.87 | 28.76 | 33.78 | 26.24 | 28.93 |
| PACS01T-IGR-BR261 | 28.76 | 25.74 | 31.81 | 27.60 | 29.70 | 26.97 | 27.90 |
| PACS01T-IGR-BR262 | 27.96 | 27.87 | 31.02 | 27.87 | 30.00 | 26.19 | 26.92 |
| PACS01T-IGR-BR265 | 27.93 | 27.93 | 29.89 | 27.82 | 32.28 | 25.92 | 27.97 |
| PACS01T-IGR-BR266 | 27.73 | 27.81 | 30.76 | 28.75 | 28.85 | 26.64 | 27.79 |
| PACS01T-IGR-BR267 | 28.48 | 26.91 | 30.28 | 27.39 | 31.57 | 26.48 | 28.42 |
| PACS01T-IGR-BR268 | 27.92 | 26.90 | 30.90 | 27.02 | 29.90 | 25.96 | 27.87 |
| PACS01T-IGR-BR270 | 28.70 | 26.00 | 28.66 | 27.88 | 31.89 | 25.86 | 27.84 |
| PACS01T-IGR_BR272 | 28.94 | 27.61 | 29.83 | 29.78 | | 26.45 | 28.85 |
| PACS01T-IGR-BR273 | 27.89 | 27.91 | 29.53 | 27.63 | 29.86 | 25.91 | 27.89 |
| PACS01T-IGR-BR274 | 28.18 | 28.57 | 30.83 | 28.97 | 31.87 | 26.22 | 28.85 |
| PACS01T-IGR-BR275 | 29.84 | 27.85 | 31.87 | 29.24 | 28.92 | 26.84 | 27.17 |
| PACS01T-IGR-BR277 | 28.60 | 27.81 | 30.83 | 27.97 | 30.82 | 25.90 | 27.91 |

TABLE 3-continued

Ct values in tumor and normal tissues for each DNA polymerase gene, as derived from Q-PCR analysis

| | | | | | | | |
|---|---|---|---|---|---|---|---|
| PACS01T-IGR-BR278 | 27.91 | 27.90 | 31.87 | 28.86 | 30.74 | 26.58 | 27.83 |
| PACS01T-IGR-BR280 | 27.85 | 27.78 | 29.02 | 28.84 | 30.94 | 25.94 | 27.94 |
| PACS01T-IGR-BR282 | 28.58 | 27.94 | 29.81 | 28.44 | 29.84 | 25.87 | 27.72 |
| PACS01T-IGR-BR283 | 28.90 | 29.65 | 31.04 | 28.92 | 31.84 | 26.85 | 28.94 |
| PACS01T-IGR-BR284 | 28.93 | 28.56 | 30.94 | 28.71 | 30.60 | 26.93 | 26.99 |
| PACS01T-IGR-BR286 | 28.67 | 28.94 | 26.87 | 28.89 | 31.93 | 26.60 | 28.88 |
| PACS01T-IGR-BR288 | 27.92 | 29.95 | 31.97 | 27.94 | 30.09 | 25.90 | 27.95 |
| PACS01T-IGR-BR289 | 28.50 | 29.43 | 29.08 | 28.79 | 30.67 | 25.94 | 27.94 |
| PACS01T-IGR-BR290 | 28.86 | 29.02 | 30.97 | 28.63 | 29.78 | 25.89 | 28.54 |
| PACS01T-IGR-BR291 | 29.74 | 27.06 | 33.02 | 28.95 | 30.54 | 25.88 | 26.89 |
| PACS01T-BEG-BR294 | 28.48 | 27.90 | 30.73 | 28.89 | 31.39 | 26.91 | 28.63 |
| PACS01T-IPC-BR-298 | 28.92 | 27.92 | 31.90 | 28.63 | 32.88 | 26.83 | 28.86 |
| PACS01T-IPC-BR299 | 28.16 | 29.90 | 30.72 | 28.88 | 29.88 | 26.63 | 27.04 |
| PACS01T-IPC-BR300 | 27.88 | 28.39 | 29.89 | 26.96 | 32.52 | 25.92 | 27.82 |
| PACS01T-IPC-BR301 | 28.77 | 27.90 | 31.04 | 29.24 | 30.62 | 25.85 | 27.34 |
| PACS01T-IPC-BR303 | 28.89 | 26.94 | 29.55 | 28.83 | 27.95 | 25.26 | 26.71 |
| PACS01T-IPC-BR304 | 28.61 | 27.45 | 29.90 | 27.84 | 31.90 | 25.95 | 27.86 |
| PACS01T-IPC-BR305 | 27.90 | 28.27 | 28.37 | 27.60 | 31.53 | 25.93 | 28.93 |
| PACS01T-PPA-BR237 | 27.89 | 26.84 | 28.95 | 28.59 | 28.99 | 25.65 | 27.94 |
| PACS01T-PPA-BR241 | 27.91 | 27.95 | 29.88 | 28.43 | 30.06 | 26.89 | 27.86 |
| PACS01T-PPA-BR243 | 27.87 | 26.67 | 28.36 | 27.96 | 30.00 | 25.88 | 28.75 |
| PACS01T-PPA-BR244 | 28.99 | 27.36 | 30.99 | 29.84 | 28.49 | 26.23 | 27.91 |
| PACS01T-PPA-BR246 | 27.87 | 27.91 | 29.98 | 28.43 | 29.89 | 25.93 | 28.80 |
| PACS01T-PPA-BR249 | 27.25 | 25.92 | 29.61 | 27.48 | 28.43 | 25.45 | 27.82 |
| PACS01T-PPA-BR250 | 27.94 | 28.27 | 28.93 | 28.02 | 31.83 | 25.94 | 28.86 |

TABLE 3-continued

Ct values in tumor and normal tissues for each DNA polymerase gene, as derived from Q-PCR analysis

| | | | | | | | |
|---|---|---|---|---|---|---|---|
| PACS01T-PPA-BR251 | 27.53 | 28.86 | 31.89 | 28.32 | 27.47 | 24.80 | 27.78 |
| PACS01T-PPA-BR253 | 27.92 | 27.95 | 29.83 | 27.93 | 31.77 | 25.21 | 28.92 |
| PACS01T-PPA-BR254 | 27.87 | 26.91 | 29.62 | 27.94 | 28.12 | 25.96 | 27.95 |
| Normal tissues | | | | | | | |
| C51 | 27.74 | 27.93 | 29.93 | 27.80 | 29.45 | 25.32 | 27.21 |
| PORL1 | 29.88 | 28.53 | 32.88 | 29.88 | 33.97 | 27.57 | 29.79 |
| GARL2 | 30.01 | 28.90 | 33.60 | 29.35 | 35.02 | 27.93 | 30.37 |
| MISL3 | 28.93 | 27.81 | 32.89 | 28.89 | 32.87 | 26.84 | 28.89 |
| TROL4 | 29.84 | 27.89 | 31.67 | 28.57 | 33.81 | 27.02 | 29.32 |
| GERL5 | 29.58 | 28.67 | 31.88 | 28.86 | 33.63 | 26.99 | 29.11 |

| SET2 | POLA1 | POLD1 | POLE | REV1 | POLH | POLM | POLK | REV3L/POLZ |
|---|---|---|---|---|---|---|---|---|
| Tumors | | | | | | | | |
| PACS01-AVA-BR007 | 27.81 | 27.89 | 26.89 | 27.88 | 27.90 | 27.68 | 26.53 | 27.88 |
| PACS01-AVA-BR008 | 26.82 | 27.77 | 26.93 | 27.35 | 27.75 | 28.01 | 26.93 | 28.81 |
| PACS01-FBA-BR085 | 26.60 | 26.89 | 25.93 | 27.02 | 26.97 | 27.44 | 25.88 | 26.63 |
| PACS01-FBA-BR087 | 27.87 | 27.58 | 26.51 | 26.90 | 27.33 | 27.77 | 25.74 | 26.91 |
| PACS01-FBA-BR089 | 27.92 | 28.85 | 27.50 | 26.78 | 27.50 | 26.87 | 26.84 | 26.96 |
| PACS01-FBA-BR091 | 27.96 | 27.90 | 26.88 | 26.91 | 27.77 | 27.24 | 26.53 | 27.37 |
| PACS01-FLE-BR024 | 27.26 | 27.19 | 26.07 | 26.91 | 27.54 | 26.98 | 25.86 | 26.58 |
| PACS01-FLE-BR025 | 26.93 | 27.00 | 25.97 | 26.51 | 26.88 | 26.82 | 25.07 | 25.83 |
| PACS01-FLE-BR027 | 26.93 | 26.94 | 26.53 | 25.47 | 26.81 | 26.90 | 25.37 | 25.90 |
| PACS01-FLE-BR028 | 27.46 | 26.89 | 26.78 | 25.96 | 27.89 | 26.48 | 25.91 | 26.72 |
| PACS01-FLE-BR029 | 26.84 | 26.93 | 25.83 | 26.83 | 26.85 | 26.86 | 25.90 | 27.89 |
| PACS01-FLE-BR030 | 26.75 | 26.84 | 25.45 | 26.77 | 26.78 | 26.70 | 25.81 | 27.87 |
| PACS01-FLE-BR031 | 27.42 | 28.03 | 27.48 | 26.82 | 27.37 | 27.78 | 25.87 | 26.73 |
| PACS01-FLE-BR032 | 26.88 | 27.20 | 26.91 | 26.66 | 26.94 | 27.89 | 25.69 | 26.85 |
| PACS01-FLE-BR033 | 27.65 | 27.84 | 26.79 | 26.83 | 26.72 | 27.01 | 25.38 | 26.77 |
| PACS01-FLE-BR034 | 27.90 | 27.74 | 26.76 | 26.66 | 26.92 | 27.53 | 25.88 | 26.91 |
| PACS01-FLE-BR035 | 26.93 | 27.82 | 25.84 | 26.91 | 27.80 | 26.38 | 25.88 | 26.91 |

TABLE 3-continued

Ct values in tumor and normal tissues for each DNA polymerase gene, as derived from Q-PCR analysis

| | | | | | | | | |
|---|---|---|---|---|---|---|---|---|
| PACS01-FLE-BR036 | 26.95 | 26.94 | 26.13 | 26.72 | 26.70 | 26.90 | 25.80 | 26.64 |
| PACS01-FLE-BR037 | 25.97 | 24.68 | 24.95 | 26.28 | 25.81 | 27.71 | 25.75 | 25.91 |
| PACS01-FLE-BR038 | 26.96 | 26.92 | 25.38 | 26.95 | 26.78 | 27.05 | 25.79 | 27.80 |
| PACS01-HBE-BR045 | 26.91 | 26.77 | 24.92 | 26.84 | 26.10 | 26.87 | 25.90 | 26.84 |
| PACS01-IPC-BR018 | 27.68 | 27.82 | 26.89 | 26.70 | 26.79 | 27.85 | 25.84 | 26.86 |
| PACS01-IPC-BR021 | 26.97 | 26.90 | 26.24 | 26.83 | 26.87 | 27.69 | 25.44 | 25.96 |
| PACS01-IPC-BR022 | 27.19 | 27.96 | 26.89 | 26.85 | 27.55 | 27.92 | 25.95 | 26.47 |
| PACS01-JGO-BR012 | 27.50 | 26.83 | 25.86 | 27.71 | 26.00 | 27.36 | 25.88 | 26.86 |
| PACS01-JGO-BR014 | 27.92 | 27.10 | 26.82 | 27.97 | 25.91 | 27.88 | 25.93 | 26.99 |
| PACS01-JGO-BR016 | 26.93 | 27.81 | 26.40 | 26.74 | 26.89 | 27.91 | 25.43 | 26.83 |
| PACS01-OLA-BR041 | 25.95 | 26.68 | 25.83 | 26.91 | 25.99 | 26.90 | 24.37 | 26.71 |
| PACS01-OLA-BR042 | 26.93 | 26.84 | 26.81 | 27.61 | 26.88 | 27.78 | 26.03 | 27.95 |
| PACS01-OLA-BR043 | 26.97 | 27.03 | 26.40 | 26.98 | 26.84 | 27.30 | 25.79 | 26.77 |
| PACS01-OLA-BR044 | 27.95 | 27.37 | 26.92 | 28.24 | 27.81 | 28.07 | 28.90 | 27.76 |
| PACS01-PPA-BR047 | 27.10 | 25.88 | 25.93 | 27.51 | 27.93 | 28.97 | 26.89 | 26.04 |
| PACS01-PPA-BR048 | 28.03 | 27.88 | 26.50 | 26.94 | 27.54 | 27.04 | 26.31 | 26.76 |
| PACS01-PPA-BR049 | 27.33 | 27.91 | 27.71 | 26.89 | 27.30 | 27.91 | 25.93 | 26.24 |
| PACS01-PPA-BR050 | 27.00 | 27.07 | 26.91 | 26.78 | 25.89 | 28.83 | 26.65 | 26.88 |
| PACS01-PPA-BR053 | 26.90 | 27.72 | 26.57 | 26.79 | 26.79 | 27.59 | 26.84 | 26.56 |
| PACS01-PPA-BR057 | 27.77 | 27.89 | 26.94 | 26.98 | 27.02 | 27.87 | 26.83 | 26.91 |
| PACS01-PPA-BR058 | 26.95 | 26.92 | 26.72 | 26.80 | 27.00 | 26.67 | 26.29 | 26.38 |
| PACS01-RGA-BR061 | 26.73 | 26.90 | 25.95 | 25.89 | 26.39 | 26.86 | 24.93 | 25.88 |
| PACS01-RGA-BR062 | 27.07 | 27.78 | 27.73 | 26.95 | 26.95 | 26.90 | 25.93 | 26.91 |
| PACS01-RGA-BR063 | 26.96 | 27.87 | 26.90 | 26.76 | 27.10 | 27.04 | 26.36 | 26.46 |
| PACS01-RGA-BR065 | 27.91 | 27.95 | 26.93 | 27.02 | 27.61 | 27.95 | 25.95 | 27.70 |

TABLE 3-continued

Ct values in tumor and normal tissues for each DNA polymerase gene, as derived from Q-PCR analysis

| | | | | | | | | |
|---|---|---|---|---|---|---|---|---|
| PACS01-RGA-BR066 | 27.89 | 27.69 | 26.76 | 26.32 | 27.84 | 27.82 | 25.72 | 26.96 |
| PACS01-RGA-BR067 | 27.99 | 28.93 | 27.56 | 27.79 | 28.85 | 27.93 | 26.55 | 27.82 |
| PACS01-RGA-BR069 | 27.41 | 28.89 | 26.90 | 26.44 | 27.73 | 26.75 | 25.91 | 26.84 |
| PACS01-RGA-BR070 | 27.24 | 27.24 | 26.71 | 26.89 | 26.86 | 26.92 | 25.87 | 26.90 |
| PACS01-RGA-BR071 | 26.22 | 26.35 | 25.81 | 26.64 | 25.92 | 26.92 | 24.53 | 25.75 |
| PACS01-RGA-BR072 | 26.91 | 27.03 | 26.83 | 26.91 | 26.79 | 27.87 | 25.89 | 26.99 |
| PACS01-RGA-BR073 | 28.96 | 28.71 | 28.54 | 27.70 | 28.53 | 28.80 | 28.59 | 29.95 |
| PACS01-RGA-BR074 | 26.85 | 27.85 | 26.84 | 25.91 | 26.83 | 27.44 | 25.90 | 27.35 |
| PACS01-RGA-BR075 | 26.66 | 26.93 | 25.61 | 25.74 | 26.40 | 26.26 | 24.93 | 25.93 |
| PACS01-RGA-BR076 | 26.82 | 27.77 | 26.86 | 27.81 | 26.85 | 27.87 | 26.62 | 27.93 |
| PACS01-RGA-BR077 | 26.95 | 27.93 | 26.22 | 26.85 | 27.01 | 27.83 | 25.91 | 26.67 |
| PACS01-RGA-BR078 | 26.97 | 26.94 | 27.80 | 28.17 | 26.92 | 28.80 | 26.62 | 27.92 |
| PACS01-RGA-BR079 | 27.56 | 27.80 | 26.89 | 27.07 | 27.66 | 27.95 | 26.07 | 27.47 |
| PACS01-RGA-BR080 | 26.75 | 26.95 | 25.79 | 26.64 | 26.54 | 26.69 | 24.80 | 26.72 |
| PACS01-RGA-BR081 | 26.90 | 26.32 | 25.63 | 26.94 | 25.87 | 26.92 | 25.02 | 26.89 |
| PACS01T-AVA-BR167 | 27.95 | 27.64 | 26.90 | 26.97 | 26.93 | 27.12 | 25.52 | 26.64 |
| PACS01T-AVA-BR168 | 27.57 | 27.04 | 26.97 | 27.26 | 27.02 | 27.60 | 25.93 | 27.92 |
| PACS01T-AVA-BR170 | 27.62 | 26.96 | 26.56 | 26.85 | 27.57 | 27.89 | 25.95 | 26.88 |
| PACS01T-AVA-BR172 | 29.90 | 28.39 | 28.80 | 28.24 | 28.84 | 28.87 | 27.41 | 28.78 |
| PACS01T-AVA-BR173 | 27.50 | 26.87 | 26.02 | 27.61 | 26.91 | 27.93 | 26.34 | 27.88 |
| PACS01T-CJP-BR156 | 27.61 | 27.96 | 26.31 | 26.69 | 26.87 | 27.58 | 26.36 | 26.82 |
| PACS01T-CJP-BR159 | 27.63 | 27.40 | 26.85 | 26.91 | 27.03 | 27.92 | 26.23 | 26.93 |
| PACS01T-CJP-BR160 | 27.91 | 27.84 | 26.78 | 26.80 | 26.78 | 27.73 | 25.92 | 26.44 |
| PACS01T-CJP-BR164 | 27.43 | 27.69 | 26.94 | 27.23 | 27.86 | 27.87 | 26.85 | 27.91 |
| PACS01T-CJP-BR166 | 27.99 | 27.91 | 26.46 | 26.99 | 27.57 | 27.18 | 26.80 | 27.87 |

TABLE 3-continued

Ct values in tumor and normal tissues for each DNA polymerase gene, as derived from Q-PCR analysis

| | | | | | | | | |
|---|---|---|---|---|---|---|---|---|
| PACS01T-FBA-BR187 | 26.92 | 27.38 | 25.92 | 26.85 | 26.64 | 27.29 | 25.79 | 26.76 |
| PACS01T-FBA-BR188 | 27.81 | 27.95 | 26.79 | 27.49 | 27.81 | 27.89 | 26.73 | 27.94 |
| PACS01T-FBA-BR189 | 27.98 | 27.63 | 26.76 | 26.97 | 27.75 | 27.26 | 26.80 | 27.83 |
| PACS01T-FBA-BR190 | 28.60 | 27.80 | 27.88 | 27.42 | 27.84 | 27.96 | 26.82 | 27.85 |
| PACS01T-FBA-BR192 | 27.34 | 27.55 | 25.88 | 26.88 | 26.93 | 27.29 | 25.64 | 27.92 |
| PACS01T-FBA-BR193 | 26.91 | 26.95 | 25.90 | 26.34 | 26.40 | 27.05 | 25.85 | 26.88 |
| PACS01T-FBA-BR194 | 27.42 | 27.60 | 26.85 | 27.38 | 26.96 | 26.87 | 25.87 | 28.69 |
| PACS01T-FBA-BR195 | 24.94 | 26.90 | 25.74 | 24.92 | 25.59 | 25.84 | 24.39 | 25.93 |
| PACS01T-FBA-BR197 | 27.88 | 27.75 | 26.90 | 26.85 | 27.13 | 28.04 | 26.59 | 26.90 |
| PACS01T-FBA-BR198 | 27.52 | 26.91 | 26.72 | 27.25 | 26.77 | 27.40 | 26.92 | 27.14 |
| PACS01T-FBA-BR199 | 26.89 | 27.10 | 26.81 | 27.08 | 27.51 | 27.35 | 25.88 | 26.92 |
| PACS01T-FBA-BR200 | 28.97 | 27.86 | 26.90 | 27.99 | 27.86 | 28.80 | 28.00 | 28.54 |
| PACS01T-FBA-BR201 | 27.32 | 27.85 | 25.89 | 27.16 | 27.75 | 26.97 | 26.40 | 26.91 |
| PACS01T-FBA-BR202 | 26.91 | 26.69 | 25.64 | 26.16 | 26.92 | 26.26 | 25.87 | 25.92 |
| PACS01T-FBA-BR203 | 27.92 | 27.91 | 26.14 | 27.53 | 26.41 | 27.88 | 26.81 | 27.64 |
| PACS01T-FBA-BR204 | 27.78 | 26.52 | 25.78 | 27.93 | 26.83 | 27.87 | 26.60 | 26.93 |
| PACS01T-FBA-BR205 | 27.53 | 26.27 | 26.66 | 27.73 | 26.70 | 27.92 | 26.80 | 27.39 |
| PACS01T-FBA-BR206 | 27.87 | 27.91 | 26.89 | 27.97 | 27.80 | 27.81 | 27.56 | 27.90 |
| PACS01T-FBA-BR207 | 27.81 | 27.32 | 27.75 | 27.77 | 27.85 | 27.55 | 26.33 | 27.88 |
| PACS01T-FBA-BR208 | 26.93 | 26.88 | 26.66 | 26.88 | 26.62 | 26.92 | 25.80 | 26.85 |
| PACS01T-FLE-BR174 | 27.95 | 27.89 | 27.38 | 27.91 | 27.52 | 28.73 | 26.93 | 27.53 |
| PACS01T-FLE-BR179 | 27.89 | 27.60 | 27.80 | 27.81 | 27.92 | 27.75 | 26.96 | 26.84 |
| PACS01T-FLE-BR180 | 28.04 | 28.04 | 27.72 | 27.40 | 27.79 | 28.83 | 26.56 | 27.96 |
| PACS01T-FLE-BR181 | 27.21 | 27.77 | 26.99 | 26.89 | 26.90 | 27.59 | 25.94 | 27.54 |
| PACS01T-FLE-BR184 | 26.88 | 27.86 | 25.78 | 26.51 | 26.74 | 26.96 | 25.69 | 26.94 |

TABLE 3-continued

Ct values in tumor and normal tissues for each DNA polymerase gene, as derived from Q-PCR analysis

| | | | | | | | | |
|---|---|---|---|---|---|---|---|---|
| PACS01T-FLE-BR185 | 26.64 | 26.64 | 26.89 | 26.93 | 27.91 | 24.95 | 26.89 | 27.00 |
| PACS01T-FLE-BR186 | 27.93 | 27.81 | 26.84 | 27.16 | 27.85 | 27.89 | 26.69 | 27.37 |
| PACS01T-JGO-BR231 | 26.56 | 26.89 | 26.42 | 26.94 | 26.38 | 26.95 | 25.80 | 26.90 |
| PACS01T-JGO-BR234 | 26.92 | 27.73 | 25.88 | 26.88 | 25.88 | 26.49 | 25.89 | 26.87 |
| PACS01T-PPA-BR235 | 26.94 | 26.96 | 25.94 | 26.89 | 26.49 | 27.08 | 25.91 | 26.91 |
| PACS01T-PPA-BR236 | 26.66 | 26.82 | 25.28 | 26.86 | 26.81 | 27.85 | 26.84 | 27.42 |
| PACS01T-RGA-BR209 | 27.95 | 27.33 | 26.71 | 26.97 | 26.85 | 26.97 | 25.75 | 27.70 |
| PACS01T-RGA-BR211 | 28.84 | 27.98 | 27.89 | 27.72 | 27.79 | 28.23 | 26.94 | 27.85 |
| PACS01T-RGA-BR212 | 25.80 | 25.12 | 24.80 | 25.72 | 27.13 | 26.83 | 25.81 | 25.51 |
| PACS01T-RGA-BR214 | 27.93 | 26.93 | 26.60 | 26.64 | 26.88 | 27.05 | 25.92 | 26.94 |
| PACS01T-RGA-BR215 | 27.81 | 26.99 | 26.91 | 27.91 | 27.71 | 27.93 | 26.84 | 27.88 |
| PACS01T-RGA-BR219 | 27.65 | 27.76 | 26.85 | 27.47 | 27.27 | 27.90 | 26.84 | 27.25 |
| PACS01T-RGA-BR220 | 26.95 | 27.00 | 26.74 | 26.96 | 26.87 | 26.89 | 25.79 | 26.92 |
| Normal tissues | | | | | | | | |
| C51 | 26.89 | 27.65 | 26.92 | 25.80 | 27.93 | 27.96 | 24.74 | 25.91 |
| PORL1 | 29.11 | 29.57 | 29.35 | 27.78 | 28.83 | 29.82 | 27.24 | 28.14 |
| GAR2 | 29.75 | 30.87 | 29.94 | 28.37 | 29.63 | 30.28 | 27.78 | 28.69 |
| MISL3 | 28.92 | 28.92 | 28.78 | 26.94 | 28.78 | 29.32 | 26.44 | 27.90 |
| FAV6 | 29.88 | 30.89 | 29.82 | 28.87 | 29.48 | 30.59 | 27.94 | 29.00 |
| ROV3 | 29.74 | 29.46 | 29.77 | 27.87 | 29.74 | 29.98 | 26.94 | 28.84 |
| ZIT5 | 29.31 | 29.75 | 29.46 | 28.77 | 28.88 | 29.67 | 27.61 | 28.92 |

| | SET2 | POLL | POLB | POLN | POLI | POLQ | IPO8 | HMBS |
|---|---|---|---|---|---|---|---|---|
| | Tumors | | | | | | | |
| PACS01-AVA-BR007 | | 28.51 | 27.82 | 28.70 | 28.66 | 30.93 | 26.75 | 28.93 |
| PACS01-AVA-BR008 | | 28.17 | 27.45 | 30.61 | 28.95 | 29.72 | 26.24 | 28.72 |
| PACS01-FBA-BR085 | | 27.92 | 26.89 | 29.75 | 28.79 | 28.75 | 25.88 | 28.54 |
| PACS01-FBA-BR087 | | 27.48 | 28.30 | 29.85 | 28.83 | 33.07 | 26.08 | 27.88 |
| PACS01-FBA-BR089 | | 27.88 | 27.46 | 29.04 | 27.91 | 33.24 | 26.51 | 29.30 |
| PACS01-FBA-BR091 | | 28.13 | 25.91 | 30.93 | 28.47 | 29.93 | 25.87 | 27.89 |
| PACS01-FLE-BR024 | | 27.87 | 26.86 | 28.90 | 28.34 | 31.95 | 26.82 | 28.87 |

TABLE 3-continued

Ct values in tumor and normal tissues for each DNA polymerase gene, as derived from Q-PCR analysis

| | | | | | | | |
|---|---|---|---|---|---|---|---|
| PACS01-FLE-BR025 | 27.93 | 27.03 | 28.60 | 27.94 | 30.86 | 25.75 | 27.36 |
| PACS01-FLE-BR027 | 27.88 | 26.52 | 29.79 | 27.81 | 29.35 | 24.99 | 27.55 |
| PACS01-FLE-BR028 | 27.98 | 27.87 | 28.91 | 28.59 | 29.86 | 25.55 | 26.91 |
| PACS01-FLE-BR029 | 27.83 | 27.85 | 28.78 | 27.59 | 29.54 | 25.82 | 27.57 |
| PACS01-FLE-BR030 | 27.29 | 26.23 | 28.78 | 27.87 | 29.84 | 25.19 | 27.96 |
| PACS01-FLE-BR031 | 27.73 | 27.76 | 29.96 | 27.82 | 31.74 | 25.93 | 28.83 |
| PACS01-FLE-BR032 | 26.95 | 26.83 | 29.82 | 28.92 | 29.94 | 25.78 | 28.58 |
| PACS01-FLE-BR033 | 27.86 | 27.84 | 28.87 | 27.71 | 29.76 | 26.04 | 28.64 |
| PACS01-FLE-BR034 | 28.24 | 28.36 | 29.57 | 27.94 | 30.72 | 25.86 | 27.97 |
| PACS01-FLE-BR035 | 27.88 | 27.81 | 29.98 | 27.50 | 31.36 | 25.80 | 28.61 |
| PACS01-FLE-BR036 | 27.85 | 26.88 | 29.71 | 27.94 | 30.21 | 25.36 | 28.86 |
| PACS01-FLE-BR037 | 28.06 | 26.95 | 30.20 | 28.12 | 27.54 | 25.30 | 27.48 |
| PACS01-FLE-BR038 | 27.57 | 27.68 | 29.92 | 27.94 | 29.95 | 25.80 | 27.89 |
| PACS01-HBE-BR045 | 27.88 | 26.38 | 28.40 | 27.38 | 27.64 | 25.94 | 26.85 |
| PACS01-IPC-BR018 | 27.86 | 28.86 | 28.91 | 27.79 | | 25.93 | 28.82 |
| PACS01-IPC-BR021 | 27.78 | 28.93 | 29.95 | 27.72 | 30.00 | 25.47 | 27.94 |
| PACS01-IPC-BR022 | 27.83 | 27.84 | 30.85 | 27.81 | 33.40 | 25.95 | 28.33 |
| PACS01-JGO-BR012 | 27.85 | 26.86 | 29.45 | 27.66 | 28.92 | 26.66 | 27.88 |
| PACS01-JGO-BR014 | 28.92 | 27.69 | 30.70 | 28.92 | 29.83 | 25.86 | 27.80 |
| PACS01-JGO-BR016 | 27.69 | 26.47 | 29.90 | 27.89 | 29.94 | 25.82 | 28.71 |
| PACS01-OLA-BR041 | 27.43 | 25.43 | 28.87 | 27.50 | 28.52 | 25.19 | 26.91 |
| PACS01-OLA-BR042 | 28.04 | 25.92 | 30.64 | 27.95 | 29.91 | 25.93 | 27.86 |
| PACS01-OLA-BR043 | 26.86 | 27.47 | 29.25 | 27.49 | 30.92 | 25.84 | 27.89 |
| PACS01-OLA-BR044 | 27.48 | 27.76 | 30.96 | 27.90 | 30.73 | 26.02 | 26.87 |
| PACS01-PPA-BR047 | 28.83 | 26.83 | 31.75 | 27.64 | 29.04 | 25.79 | 27.30 |

TABLE 3-continued

Ct values in tumor and normal tissues for each DNA polymerase gene, as derived from Q-PCR analysis

| | | | | | | | |
|---|---|---|---|---|---|---|---|
| PACS01-PPA-BR048 | 28.67 | 26.93 | 31.80 | 27.89 | 29.31 | 26.41 | 28.08 |
| PACS01-PPA-BR049 | 27.16 | 27.82 | 29.10 | 27.49 | 32.49 | 25.86 | 27.69 |
| PACS01-PPA-BR050 | 28.86 | 26.12 | 32.58 | 27.95 | 29.89 | 26.02 | 26.90 |
| PACS01-PPA-BR053 | 27.90 | 27.94 | 30.85 | 26.95 | 29.86 | 26.92 | 27.46 |
| PACS01-PPA-BR057 | 28.90 | 27.19 | 29.82 | 27.59 | 30.97 | 26.35 | 28.89 |
| PACS01-PPA-BR058 | 27.90 | 26.81 | 29.88 | 27.82 | 31.02 | 25.77 | 27.99 |
| PACS01-RGA-BR061 | 26.87 | 26.90 | 28.74 | 26.92 | 30.96 | 24.74 | 26.95 |
| PACS01-RGA-BR062 | 27.46 | 27.63 | 29.51 | 27.57 | 31.11 | 25.93 | 28.80 |
| PACS01-RGA-BR063 | 27.84 | 25.95 | 30.92 | 27.94 | 28.89 | 26.17 | 28.90 |
| PACS01-RGA-BR065 | 27.90 | 27.74 | 29.20 | 28.38 | 30.07 | 26.17 | 28.78 |
| PACS01-RGA-BR066 | 27.81 | 27.82 | 28.93 | 27.93 | 31.77 | 25.88 | 27.88 |
| PACS01-RGA-BR067 | 28.72 | 28.94 | 29.81 | 29.36 | 31.54 | 26.75 | 29.27 |
| PACS01-RGA-BR069 | 27.90 | 27.58 | 29.91 | 28.87 | 33.89 | 25.90 | 28.89 |
| PACS01-RGA-BR070 | 27.84 | 27.88 | 27.55 | 27.51 | 30.50 | 25.91 | 27.80 |
| PACS01-RGA-BR071 | 26.78 | 26.07 | 28.30 | 26.22 | 29.95 | 24.90 | 26.50 |
| PACS01-RGA-BR072 | 26.99 | 26.90 | 29.01 | 26.90 | 30.79 | 25.54 | 26.92 |
| PACS01-RGA-BR073 | 28.44 | 28.93 | 31.69 | 29.81 | | 27.94 | 29.86 |
| PACS01-RGA-BR074 | 26.86 | 26.61 | 29.01 | 27.96 | 32.05 | 25.62 | 27.87 |
| PACS01-RGA-BR075 | 26.96 | 26.96 | 28.44 | 27.64 | 28.85 | 25.66 | 27.53 |
| PACS01-RGA-BR076 | 27.94 | 28.89 | 30.73 | 28.55 | 29.85 | 26.40 | 27.44 |
| PACS01-RGA-BR077 | 27.20 | 27.54 | 29.30 | 26.98 | 32.50 | 25.96 | 28.06 |
| PACS01-RGA-BR078 | 29.08 | 27.51 | 31.93 | 29.33 | 29.62 | 26.92 | 27.82 |
| PACS01-RGA-BR079 | 27.56 | 26.95 | 29.67 | 27.91 | 31.19 | 26.77 | 28.64 |
| PACS01-RGA-BR080 | 27.17 | 27.00 | 28.89 | 26.96 | 30.45 | 25.93 | 28.77 |
| PACS01-RGA-BR081 | 27.88 | 27.78 | 29.53 | 28.73 | 29.06 | 25.82 | 27.91 |

TABLE 3-continued

Ct values in tumor and normal tissues for each DNA polymerase gene, as derived from Q-PCR analysis

| | | | | | | | |
|---|---|---|---|---|---|---|---|
| PACS01T-AVA-BR167 | 27.87 | 27.96 | 28.61 | 27.98 | 33.00 | 25.76 | 28.70 |
| PACS01T-AVA-BR168 | 28.64 | 26.91 | 30.84 | 27.93 | 30.96 | 25.92 | 27.82 |
| PACS01T-AVA-BR170 | 27.95 | 27.91 | 29.80 | 27.69 | 30.32 | 26.90 | 28.80 |
| PACS01T-AVA-BR172 | 28.64 | 28.82 | 32.89 | 28.85 | 33.08 | 27.90 | 28.89 |
| PACS01T-AVA-BR173 | 28.40 | 27.84 | 29.92 | 28.90 | 29.26 | 25.86 | 28.47 |
| PACS01T-CJP-BR156 | 27.76 | 27.88 | 27.93 | 27.90 | 30.78 | 26.46 | 29.04 |
| PACS01T-CJP-BR159 | 28.33 | 27.92 | 29.89 | 28.65 | 30.81 | 26.06 | 28.64 |
| PACS01T-CJP-BR160 | 27.82 | 27.72 | 29.80 | 27.95 | 32.67 | 25.90 | 28.90 |
| PACS01T-CJP-BR164 | 28.15 | 27.99 | 30.88 | 28.73 | 30.28 | 26.74 | 28.67 |
| PACS01T-CJP-BR166 | 27.95 | 27.75 | 28.78 | 27.97 | 32.97 | 25.95 | 27.90 |
| PACS01T-FBA-BR187 | 27.30 | 25.75 | 28.55 | 26.99 | 29.92 | 25.77 | 28.23 |
| PACS01T-FBA-BR188 | 27.89 | 27.90 | 29.75 | 28.15 | 33.85 | 26.94 | 28.96 |
| PACS01T-FBA-BR189 | 28.86 | 27.94 | 30.99 | 28.66 | 30.71 | 25.98 | 27.11 |
| PACS01T-FBA-BR190 | 28.88 | 27.53 | 30.74 | 27.96 | 32.88 | 26.43 | 27.99 |
| PACS01T-FBA-BR192 | 27.51 | 28.92 | 29.45 | 27.30 | 31.19 | 25.94 | 28.73 |
| PACS01T-FBA-BR193 | 26.91 | 26.57 | 28.91 | 27.93 | 28.88 | 25.54 | 26.91 |
| PACS01T-FBA-BR194 | 27.37 | 28.78 | 31.09 | 26.09 | 31.23 | 25.94 | 26.91 |
| PACS01T-FBA-BR195 | 26.01 | 26.83 | 29.17 | 27.01 | 29.71 | 23.91 | 27.22 |
| PACS01T-FBA-BR197 | 28.66 | 27.76 | 29.98 | 28.88 | 32.03 | 26.84 | 28.91 |
| PACS01T-FBA-BR198 | 27.60 | 27.70 | 30.28 | 26.92 | 30.85 | 25.95 | 26.29 |
| PACS01T-FBA-BR199 | 28.62 | 25.05 | 28.80 | 27.66 | 31.76 | 26.55 | 28.40 |
| PACS01T-FBA-BR200 | 29.79 | 28.85 | 31.84 | 28.89 | 30.92 | 26.87 | 27.92 |
| PACS01T-FBA-BR201 | 27.81 | 27.89 | 28.97 | 27.92 | 29.96 | 25.94 | 27.27 |
| PACS01T-FBA-BR202 | 27.92 | 28.21 | 28.94 | 27.81 | 29.69 | 25.31 | 26.87 |
| PACS01T-FBA-BR203 | 27.83 | 26.96 | 30.73 | 27.96 | 30.96 | 26.95 | 27.93 |

TABLE 3-continued

Ct values in tumor and normal tissues for each DNA polymerase gene, as derived from Q-PCR analysis

| | | | | | | | |
|---|---|---|---|---|---|---|---|
| PACS01T-FBA-BR204 | 27.94 | 26.93 | 31.24 | 28.15 | 30.57 | 24.94 | 26.12 |
| PACS01T-FBA-BR205 | 28.70 | 26.89 | 29.58 | 28.15 | 28.52 | 26.92 | 27.60 |
| PACS01T-FBA-BR206 | 28.93 | 28.78 | 30.93 | 29.90 | 33.01 | 27.61 | 28.78 |
| PACS01T-FBA-BR207 | 27.62 | 27.00 | 31.00 | 27.00 | 31.10 | 25.88 | 28.56 |
| PACS01T-FBA-BR208 | 27.92 | 25.88 | 30.83 | 27.97 | 29.87 | 25.55 | 27.87 |
| PACS01T-FLE-BR174 | 28.92 | 28.84 | 30.88 | 29.67 | 30.87 | 26.44 | 28.90 |
| PACS01T-FLE-BR179 | 28.76 | 27.39 | 30.28 | 28.19 | 31.45 | 26.63 | 28.74 |
| PACS01T-FLE-BR180 | 28.91 | 27.88 | 30.00 | 28.83 | 32.85 | 26.90 | 28.90 |
| PACS01T-FLE-BR181 | 27.86 | 27.89 | 30.31 | 27.43 | 30.50 | 26.86 | 28.54 |
| PACS01T-FLE-BR184 | 27.22 | 27.94 | 28.91 | 27.90 | 32.87 | 26.60 | 28.88 |
| PACS01T-FLE-BR185 | 27.93 | 26.88 | 28.74 | 26.97 | 30.02 | 25.86 | 29.15 |
| PACS01T-FLE-BR186 | 28.69 | 27.76 | 30.82 | 28.97 | 30.72 | 26.20 | 27.98 |
| PACS01T-JGO-BR231 | 27.90 | 27.57 | 28.39 | 27.57 | 29.85 | 25.89 | 27.15 |
| PACS01T-JGO-BR234 | 27.87 | 26.90 | 27.81 | 27.93 | 30.85 | 25.93 | 28.02 |
| PACS01T-PPA-BR235 | 27.52 | 28.41 | 29.37 | 27.90 | 29.64 | 25.83 | 28.51 |
| PACS01T-PPA-BR236 | 27.96 | 26.92 | 30.86 | 28.44 | 28.86 | 25.94 | 27.91 |
| PACS01T-RGA-BR209 | 27.53 | 27.56 | 30.13 | 27.09 | 32.79 | 25.89 | 27.95 |
| PACS01T-RGA-BR211 | 28.96 | 29.86 | 29.82 | 28.91 | 31.96 | 26.72 | 28.85 |
| PACS01T-RGA-BR212 | 27.15 | 26.99 | 27.68 | 27.81 | 27.88 | 25.61 | 26.44 |
| PACS01T-RGA-BR214 | 27.89 | 27.47 | 30.90 | 27.86 | 32.63 | 25.93 | 27.91 |
| PACS01T-RGA-BR215 | 28.80 | 27.60 | 29.73 | 28.82 | 30.79 | 26.95 | 27.68 |
| PACS01T-RGA-BR219 | 28.76 | 27.94 | 29.86 | 28.85 | 30.97 | 26.52 | 28.26 |
| PACS01T-RGA-BR220 | 27.87 | 27.34 | 29.86 | 27.60 | 30.98 | 25.82 | 27.86 |
| Normal tissues | | | | | | | |
| C51 | 27.25 | 27.76 | 29.04 | 27.92 | 32.83 | 25.92 | 27.78 |
| PORL1 | 29.20 | 28.80 | 32.45 | 29.14 | 33.24 | 27.31 | 28.89 |
| GAR2 | 29.75 | 29.91 | 32.84 | 29.78 | 33.87 | 28.08 | 30.77 |
| MISL3 | 28.95 | 27.84 | 31.75 | 28.66 | 33.89 | 26.91 | 28.91 |

TABLE 3-continued

Ct values in tumor and normal tissues for each DNA polymerase gene, as derived from Q-PCR analysis

| FAV6 | 29.93 | 28.89 | 32.55 | 29.81 | 35.94 | 27.92 | 29.86 |
| ROV3 | 29.85 | 28.62 | 32.11 | 28.88 | 34.71 | 27.89 | 29.88 |
| ZIT5 | 29.88 | 27.99 | 31.95 | 28.78 |  | 27.67 | 29.64 |

Interestingly, the most recently discovered DNA polymerase POLN, which is the most closely related to POLQ (Marini et al. *J Biol Chem* 278: 32014-32019, 2003), was also significantly over-expressed in tumors. We also noticed a significant under-expression of tumor transcripts for the specialized DNA polymerase POLB gene (FIG. 1). Very similar data were found when an independent genotyping analysis (i.e. using an independent batch of Low Density Arrays) was performed in a second set of tumors (n=105, Table 1 and FIG. 2), except that in addition to POLB, REV1 and POLK T/N ratios were mostly lower than 1 in this series. By using a non parametric Spearman's correlation graphical display, we found that in the first tumor set (n=101), expression defects of genes encoding the specialized polymerases POLN, POLM, POLK, POLL and POLI were significantly correlated (FIG. 3), all Spearman>0.5). In contrast, the specific expression profile that we found for POLQ was not clustered in this pattern, showing that POLQ gene upregulation in tumors was independent from the regulation of other specialized polymerases.

2.1.2. Intra-Tumoral Up-Regulation of POLQ is Associated with a Poor Clinical Outcome To investigate whether the expression levels of DNA polymerases in tumors could be related to patient survival, a log-rank test was carried out (FIG. 4). For the French cohort, high expression of the POLQ gene was significantly associated with poor survival (p=0.0001) (FIG. 4A), strongly suggesting that POLQ gene up-regulation is associated with worse survival in breast cancer patients.

Lymph node metastasis is associated with poor survival in breast cancer, as confirmed in both our cohorts (data not shown). Results from the French cohort (FIG. 4B) indicate that patients with high number of positive lymph nodes (2 or more nodes involved with metastatic breast cancer) but low POLQ expression had a significantly better survival rate than patients with a high expression of POLQ and a high number of lymph nodes (pair wise comparison, French cohort, p=0.0001). It should be highlighted that patients with a high number of lymph nodes and a low level of POLQ expression had a survival rate comparable to patients with low number of lymph nodes and high level of POLQ expression (pair wise comparison, French cohort, p=0.793). Only the group of patients with a high number of positive lymph nodes and a high level of POLQ expression had a poor survival.

A significant statistical association was shown between POLQ expression and the number of positive lymph nodes (p=0.0172), histological grade III (p<0.0001), tumor size (Spearman 0.1611, p=0.0237), estrogen receptor (ER) status (p<0.0001), progesterone receptor (PgR) status (p=0.0034), Ki67 expression (p<0.0001) and HER2 status (p=0.0032) (Table 4). Interestingly, the patients displaying "triple-negative" tumors (i.e., ER negative, PgR negative, HER2 negative) showed higher levels of POLQ expression (p=0.0422). A multivariate analysis was conducted including the number of lymph nodes involved, histological grade, hormone receptors, vascular invasion and POLQ expression. (Table 5). Very interestingly the final models contain lymph node involvement (HR=2.78, CI95%=[1.29;6.01]) and POLQ expression (HR=3.33, Ci95%=[1.56;7.12]).

TABLE 4

Correlation between POLQ expression and clinical status

|  | Pol Q Low (N = 138) | | Pol Q High (N = 65) | | |
| --- | --- | --- | --- | --- | --- |
|  | n | % | n | % | p |
| Age (cl) |  |  |  |  | p = 0.5589 (chi – 2) |
| <50 | 64 | (46.4) | 33 | (50.8) |  |
| ≥50 | 74 | (53.6) | 32 | (49.2) |  |
| Positive nodes |  |  |  |  | p = 0.0172 (chi – 2) |
| 1-3 | 94 | (68.1) | 33 | (50.8) |  |
| ≥3 | 44 | (31.9) | 32 | (49.2) |  |
| Histological type |  |  |  |  | p = 0.0003 (chi – 2) |
| Ductal carcinoma | 97 | (70.3) | 62 | (95.4) |  |
| Lobular carcinoma | 21 | (15.2) | 2 | (3.1) |  |
| Other | 20 | (14.5) | 1 | (1.5) |  |
| Histological grade |  |  |  |  | p < 0.0001 (chi – 2) |
| I-II | 89 | (67.4) | 12 | (18.5) |  |
| III | 43 | (32.6) | 53 | (81.5) |  |
| Missing | 6 |  | 0 |  |  |
| Tumor size |  |  |  |  | p = 0.0432 (chi – 2) |
| <2 cm | 40 | (29.6) | 10 | (16.1) |  |
| ≥2 cm | 95 | (70.4) | 52 | (83.9) |  |
| Missing | 3 |  | 3 |  |  |
| Estrogen receptor |  |  |  |  | p < 0.0001 (chi – 2) |
| Negative | 28 | (20.9) | 31 | (48.4) |  |
| Positive | 106 | (79.1) | 33 | (51.6) |  |
| Missing | 4 |  | 1 |  |  |
| Progesterone receptor |  |  |  |  | p = 0.0034 (chi – 2) |
| Negative | 69 | (51.5) | 47 | (73.4) |  |
| Positive | 65 | (48.5) | 17 | (26.6) |  |
| Missing | 4 |  | 1 |  |  |
| Ki 67 |  |  |  |  | p < 0.0001 (chi – 2) |
| <20% | 72 | (66.1) | 19 | (33.9) |  |
| ≥20% | 37 | (33.9) | 37 | (66.1) |  |
| Missing | 29 |  | 9 |  |  |
| HER2 status |  |  |  |  | p = 0.0032 (chi – 2) |
| Negative | 109 | (89.3) | 41 | (71.9) |  |
| Positive | 13 | (10.7) | 16 | (28.1) |  |
| Missing | 16 |  | 8 |  |  |
| Molecular sub-type |  |  |  |  | p = 0.0422 (chi – 2) |
| Triple negative | 15 | (12.7) | 14 | (25.0) |  |
| Others | 103 | (87.3) | 42 | (75.0) |  |
| Missing | 20 |  | 9 |  |  |

TABLE 5

Multivariate analysis - cancer specific survival (n = 192)

| | Initial model[a] | | | Final model[b] | | |
|---|---|---|---|---|---|---|
| | HR | CI95% | p (Wald) | HR | CI95% | p (Wald) |
| Nb lymph node involved | | | | | | |
| 1-3 | 1 | | | 1 | | |
| >3 | 2.80 | [1.29; 6.07] | 0.009 | 2.78 | [1.29; 6.01] | 0.009 |
| Histological grade | | | | | | |
| I-II | 1 | | | | | |
| III | 2.33 | [0.91; 6.01] | 0.079 | NS[c] | | |
| Hormone receptors | | | | | | |
| Negative | 1.54 | [0.71; 3.36] | 0.274 | NS | | |
| Positive | 1 | | | | | |
| Vascular invasion | | | | | | |
| Absence | 1 | | | | | |
| presence | 1.71 | [0.81; 3.63] | 0.161 | NS | | |
| POLQ expression | | | | | | |
| Low | 1 | | | | | |
| High | 1.99 | [0.86; 4.61] | 0.109 | 3.33 | [1.56; 7.12] | 0.002 |

[a]Initial model: including all variables with p < 0.05 in univariate analysis.
[b]Final model: same model after backward stepwise algorithm.
[c]NS, not significant after stepwise algorithm.
HR, hazard ratio;
CI confidence interval.

2.1.3. Ectopic Expression of POLQ Affects Cell Cycle and Proliferation

The data suggest that either POLQ is only a bystander prognosis marker or that it could actively contribute to tumor progression. To evaluate the specific impact of POLQ over-expression on genetic stability and cell proliferation we generated three recombinant POLQ clones (Q1, Q2 and Q3) which stably over-express increasing amounts of POLQ protein compared to the endogenous levels displayed by isogenic controls (FIG. 5A). The over-expression of POLQ transcripts in these clones (ranging from 10 to 15-fold) was comparable to that observed in tumors (data not shown). Quantitative FACS analysis after DNA staining (FIG. 5 B) revealed that Q1, Q2 and to a larger extent Q3, significantly accumulated in S phase compared to controls. We also observed a significant accumulation of Q3 cells, which expressed the highest amount of POLQ, in G2/M phase. Consistent with retardation in S phase and G2/M transition, we found that the Q3 cells proliferated more slowly in exponential culture, with an increased doubling time (25.2 h) compared to control cells (22.5 h for CTL1 and 20.2 h for CTL2) or to the other POLQ expressing clones (20.0 h for Q1 and 22.7 h for Q2) (data not shown). Taken together, these results indicate that up-regulation of POLQ in human cells affects cell-cycle progression in the absence of external stress.

2.1.4. Ectopic POLQ Expression Induces DNA Break-Mediated Damage Signaling

To investigate the impact of POLQ over-expression on genomic stability, we next performed immunofluorescence assays to detect γ-H2AX, the phosphorylated form of histone H2AX that accumulates at DSB. We observed that the POLQ over-expressing cells clearly showed a significant 2 to 3 fold increase in γ-H2AX foci formation compared to isogenic controls (FIG. 6A, Q1 p<0.002; Q2, p<0.001; Q3 p<0.003). Immunoblotting analysis with -H2AX antibodies (FIG. 7) confirmed these data. The level of activation of two central transducer kinases in DNA damage signaling, CHK1 and CHK2, was then determined. The level of phosphorylated CHK1 remained unchanged in the presence of high level of POLQ (data not shown). In contrast, immunodetection experiments analyzing foci formation of the phosphorylated form of CHK2 revealed a significant activation of the CHK2 kinase in all three cell lines (Q1 p<0.0018; Q2, p<0.002; Q3 p<0.01) compared to isogenic control cells (FIG. 6B). This data was confirmed by immunoblotting (data not shown). Interestingly, confocal analysis indicated that most of PT68-CHK2 foci in all the POLQ over-expressor cell lines colocalized with γ-H2AX foci (FIG. 6C), showing that activated CHK2 kinase was localized to sites of DNA damage. This suggests that over-expression of POLQ induces the activation of the γH2AX-ATM-CHK2 DNA damage checkpoint.

2.1.5. POLQ Over-Expressing Cells Displayed Spontaneous Chromosome Abnormalities To further investigate the consequences of POLQ over-expression on chromosomal stability, we analyzed metaphase spreads from the Q1, Q2, Q3 clones and isogenic controls. POLQ over-expression resulted in a significant increase in the frequency of cells displaying quadriradials, end-to-end fusions and chromatid breaks (25% of aberrant metaphases were detected in POLQ cells versus 15% in controls; FIG. 8). These data indicate that spontaneous chromosome instability occurs in POLQ over-expressing cells, which may be the consequences of the increased DNA breakage observed.

2.1.6. Replication Dynamics is Perturbed in POLQ-Overexpressing Cells

A proposed role of POLQ in BER could be that over-expressed POLQ interferes with the BER pathway and leads to an accumulation of endogenous DNA damage (including damage generated by reactive oxygen species). To test this hypothesis, we measured the sensitivity of the POLQ over-expressing cells to methyl-methanesulfonate (MMS) and Nitroso-N-methylurea (MNU) (FIG. 9), both of which induce DNA damage repaired by BER. We found that POLQ over-expression did not significantly affect survival to MMS and MNU treatments, suggesting that defective cell cycle progression, genetic instability as well as activation of the DNA damage checkpoint do not result from a defective BER of endogenous DNA damage in the POLQ over-expressing cells.

The results presented above led us to examine replication dynamics in POLQ overexpressing cells. To assess whether POLQ over-expression affected the rate of replication fork progression, dynamic molecular combing was performed. This method allowed us to determine the polarity of replication forks in vivo at the level of individual replicating DNA molecules as well as the distribution of fork velocities (FIG. 10). The median velocity measured in control cells was 1.699 kb/min (n=144) whereas Q2 and Q3 cells displayed a lower velocity of 1.403 kb/min (n=113) and 1.402 kb/min (n=200), respectively. In conclusion, POLQ over-expressing cells displayed a substantial reduction in the overall replication speed, demonstrating that excess POLQ constitutes a potent inducer of replicative stress in human cells. A similar over-expression of either POLB or POLK is sufficient to impede replication fork progression (Chirgwin et al. *Biochemistry* 18: 5294-5299, 1979).

2.1.7. POLQ-Overexpressing Cells are Hypersensitive to a Chk2 Inhibitor

MDA-MB231 and MCF7 breast cancer cells (ATCC) were grown in RPMI 1640+ glutamax medium. A 13.8 mM Chk2 inhibitor II Hydrate (Sigma RefC3742) stock solution was prepared by diluting the agent in DMSO (Sigma) and stored at −20° C. This solution was diluted in culture medium to give as indicated the final drug concentration. Cells were exposed to different concentrations ranging from 1 µM to 150 µM during 16 hours. Cells were washed with PBS buffer, fresh medium was added and cells were incubated for seven more days. Cells were fixed with NaCl 0.9% and stained with crystal violet (Sigma C3886). Clones containing more than 20 cells were counted. For the clonogenic assay 400 cells were seeded in six-well plates and incubated overnight. The POLQ expression was measured by real-time PCR as described above.

Cells overexpressing POLQ accumulate DNA damage. Said damages trigger the ATM-dependent DNA damage checkpoint through activation of the Chk2 protein kinase, eventually leading to cell-cycle arrest. This suggested to us that POLQ-overexpressing cells would be hypersensitive to inhibitors of DNA damage signaling. In order to test this hypothesis, the viability of the MCF7 and MDA-MB231 cells was determined in the presence of increasing amounts of a Chk2 inhibitor. In parallel, POLQ expression was assayed in each cell line.

As shown on FIG. 12, MCF7 which express more than twice as much POLQ RNA than MDA-MB231 are hypersensitive to the CHK2 inhibitor. There is thus a correlation between the expression of POLQ and the sensitivity to the inhibition of the DNA damage signaling pathway.

2.2. Lung Cancer
2.2.1. Most of DNA Replication Genes are Deregulated in Coupled Lung Tumours.

Gene expression profiles of 93 coupled primary lung adenocarcinomas at different stages of progression (Table 1) were generated from a selection of more than 80 genes known as playing a role in initiation/licensing of DNA replication, translesional (TLS) or conventional DNA elongation, DNA damage response (DDR), DNA fork protection or repair of replication-induced double-stranded breaks.

In particular, POLQ was shown by this real-time PCR analysis to be highly expressed in most of the 93 patients. Indeed, POLQ is up-regulated in tumor tissues (T) compared to adjacent control tissues (N). of the said patients (Table 6).

TABLE 6

Differential expression of POLQ s in coupled NSCLC tumours

| Replication gene | DNA transaction | N° coupled tumors | Over-expression ($\Delta Ct > 1$) | Under-expression ($\Delta Ct < 1$) | P value |
|---|---|---|---|---|---|
| PolQ | TLA DNA replication | 93 | 75 | 19 | 0.00000004 |

As shown in Table 7, we observed that the POLQ gene was more than 2-fold (T/N>2) over-regulated.

TABLE 7 exact binomial tests (P values <0.05)

| Replication gene | DNA transaction | T/N overexpression ratio | | | |
|---|---|---|---|---|---|
| | | >5 | >4 | >3 | >2 |
| POLQ | TLS DNA replication | | | $P < 6\,10^{-5}$ | $P < 1\,10^{-10}$ |

2.2.2. Deregulated 3R Expression is Associated with Poor Prognosis

A log-rank test for equality of survivor functions indicated that up-regulation of the POLQ (p<0.0033) DNA polymerase gene was associated with disease-free survival. When relapse-free survival of patients was investigated, overexpression of this gene was again significantly related to the outcome of patients (p<0.05). Finally we analyzed the disease-free survival criteria and found that POLQ (p<0.0008) was associated with a higher morbidity when overall survival was measured (FIG. 13).

TABLE 8

Multivariate analysis - cancer specific survival (n = 93)

| Gene | Terciles | Log rank Test | | | Khi2 or Fisher's exact Tests | |
|---|---|---|---|---|---|---|
| | | pvalue ≤ 0.05 → significant effect of gene expression on survival (OS, PFS, TTP) pvalue > 0.05 → non significant effect of gene expression on survival (OS, PFS, TTP) | | | pvalue ≤ 0.05 → significant association between treatment or stade N and gene expression pvalue > 0.05 → non significant association between treatment or stade N and gene expression. | |
| | | Overall survival (OS) | Progression-free survival (PFS) | Relapse-free survival (RFS) | Treatment | Stade N |
| | | Evt = death | Evt = death or relapse | Evt = relapse | Untreated patients (n = 46) Patients | N0 (n = 61) N1 (n = 11) |

TABLE 8-continued

| Multivariate analysis - cancer specific survival (n = 93) | | | | | |
|---|---|---|---|---|---|
| | | | | treated by chemo + radio (n = 11) Patients treated by chemo only (n = 36) | N2 + N3 (n = 21) |
| PolQ [−0.508, 1.75] | P = 0.0008*** | P = 0.0033** | P = 0.0359* | 0.348 | 0.7193 |

*significance with p < 0.05
**significance with p < 0.01
***significance with p < 0.001

Overexpression of POLQ is therefore associated with survival whatever the criteria used to assess survival Importantly, this association is independent of the tumor stage and of the treatment.

2.2.3. Overexpression of POLQ Leads to Genetic Abnormalities

To investigate the impact of POLQ over-expression on genomic stability, MRC5 cells were transfected with either a POLQ-carrying plasmid or the corresponding empty plasmid. Metaphase spreads from the transfected clones (Q1, Q2, Q3) and isogenic controls were analysed. POLQ overexpression resulted in a significant increase in the frequency of cells displaying quadriradials, end-to-end fusions and chromatid breaks (25% of aberrant metaphases were detected in POLQ cells versus 13% in controls; Table 9). These data indicate that spontaneous chromosome instability occurs in POLQ overexpressing cells, which may be the consequences of increased DNA breakage.

TABLE 9

| Chromosomal aberrations in POLQ-overexpressing MRC5 cells | | | | | |
|---|---|---|---|---|---|
| Chromosomal aberrations | CTL2 | CTL9 | Q1 | Q2 | Q3 |
| N° of Metaphases | 292 | 290 | 305 | 320 | 301 |
| N° of chromatid breaks | 36 | 28 | 72 | 85 | 57 |
| N° of end-to-end fusions | 12 | 10 | 32 | 24 | 32 |
| N° of dicentric chromosomes | 16 | 10 | 34 | 17 | 15 |
| Other abnormalities | 3 | 7 | 9 | 14 | 7 |
| Total N° of abnormalities | 67 | 55 | 147 | 140 | 111 |
| | | | p = 0.03 | p = 0.003 | p = 0.009 |
| % Cells with abnormalities | 10.5 | 13.8 | 24.6 | 26.6 | 25.6 |
| N° of abnormalities per cell | 0.23 | 0.19 | 0.48 | 0.44 | 0.37 |

2.2.4. POLQ-Overexpressing Cells Show Higher Sensitivity to DNA-Repair Inhibitors A proposed role of POLQ in Base Excision Repair (BER) or alternative Non Homologous End Joining (NHEJ) could be that overexpressed POLQ interferes with the BER and/or B-NHEJ pathways and leads to an accumulation of endogenous DNA damage (including damage generated by reactive oxygen species).

To test this hypothesis, POLQ-overexpressing MRC5 cells (Q14) were either treated with a sub-efficient dose of a PARP inhibitor or left untreated. As shown in FIG. 2, the proliferation of MRC5 cells overexpressing POLQ was significantly affected when these cells were treated with the said PARP inhibitor, consistent with a delayed repair of the. Likewise, Q14 cells showed significant delay in cell proliferation after irradiation at a sub-lethal dose. By contrast, MRC5 cells which did not overexpress POLQ were not affected by either treatment with the PARP inhibitor or mild irradiation.

2.2.5. POLQ Biological Role is Linked to Entry into S Phase

The role of POLQ in replication was investigated by transfecting POLQ-specific siRNA into MRC5 cells and monitoring the cell-cycle status of POLQ-depleted cells. It was immediately clear that the number of cells in S phase was lower in POLQ siRNA-expressing cells than in control cells, indicating a perturbation of the S-phase progression. This interpretation was confirmed by immunostaining of the PCNA protein, a marker of S cells, in both control and transfected cells: a significant increase in cells displaying a staining consistent with the beginning of the DNA replication was observed in the POLQ siRNA transfected cell population, but not in the control.

This perturbation of S phase could be due to an effect on replication initiation, on replication elongation, or on both. In order to assess the effect of the inhibition POLQ in DNA replication initiation, cyclin E mRNA (CCNE1, Genbank ID: NM_001238; and CCNE2, Genbank ID: NM_057749) was evaluated by Northern blotting in POLQ-depleted cells as well as in control cells. When normalized to actin transcript levels, cyclin E transcript levels were clearly more elevated in POLQ siRNA-expressing cells. Since cyclin E is required for the onset of S phase, POLQ depletion leads to an increased replication initiation activity. It is already known that POLQ affects fork velocities (see example 2.1.6. above). Deregulation of POLQ expression thus interferes with the licensing for replication, triggering a replicative stress and the genetic instability in the tumors of the study.

The invention claimed is:

1. A method for diagnosing aggressiveness of a cancer in a patient from a cancer sample of said patient, comprising:
measuring in vitro the expression level of the POLQ gene and/or its isoforms arising from alternative splicing, and the expression level of a control gene in said patient cancer sample,
calculating for said POLQ gene and/or isoform an expression level ratio of the expression level of POLQ and/or one or several of its isoforms to the expression of the said control gene in said patient cancer sample,
comparing said gene expression level ratio to a corresponding threshold value,
diagnosing cancer aggressiveness if the said ratio is superior to its corresponding threshold value,
wherein the threshold value is 15.8,
wherein an expression level ratio lower than the threshold value indicates less aggressiveness of the cancer and a better diagnosis or chance of survival as compared to a patient whose cancer sample yields an expression level ratio higher than the threshold value,
wherein the control gene is IPO8, and
wherein the expression level of POLQ and IPO8 is determined by detecting POLQ and IPO8 mRNA.

2. The method of claim 1, wherein the patient has a high number of metastatic lymph nodes.

3. The method of claim 1, wherein said cancer is breast cancer, and wherein the breast cancer expresses a wild-type p53 cDNA.

4. The method of claim 1, wherein the said cancer is lung cancer or breast cancer.

5. The method of claim 1, wherein said expression level is measured using quantitative PCR or microarray technology.

6. A method for diagnosing genetic instability in a cancer in a patient from a cancer sample of said patient, comprising:
measuring in vitro the expression level of the POLQ gene and/or its isoforms arising from alternative splicing, and the expression level of a control gene in said patient cancer sample,
calculating for said POLQ gene and/or isoform an expression level ratio of the expression level of POLQ and/or one or several of its isoforms to the expression of the said control gene in said patient cancer sample,
comparing said gene expression level ratio to a corresponding threshold value,
diagnosing cancer genetic instability if the said ratio is superior to its corresponding threshold value,
wherein the threshold value is 15.8,
wherein an expression level ratio lower than the threshold value indicates less genetic instability of the cancer and a better diagnosis or chance of survival as compared to a patient whose cancer sample yields an expression level ratio higher than the threshold value,
wherein the control gene is IPO8,
and wherein the expression level of POLQ and IPO8 is determined by detecting POLQ and IPO8 mRNA.

7. The method of claim 6, wherein the patient has a high number of metastatic lymph nodes.

8. The method of claim 6, wherein the cancer is breast cancer, and wherein the breast cancer expresses a wild-type p53 cDNA.

9. The method of claim 6, wherein the said cancer is lung cancer or breast cancer.

10. The method of claim 6, wherein said expression level is measured using quantitative PCR or microarray technology.

* * * * *